US011643655B2

(12) United States Patent
Castanotto et al.

(10) Patent No.: US 11,643,655 B2
(45) Date of Patent: May 9, 2023

(54) METHODS FOR INTRACELLULAR DELIVERY AND ENHANCED GENE TARGETING

(71) Applicant: CITY OF HOPE, Duarte, CA (US)

(72) Inventors: Daniela Castanotto, Altadena, CA (US); Cy Stein, La Canada Flintridge, CA (US); Xiaowei Zhang, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 16/349,968

(22) PCT Filed: Nov. 15, 2017

(86) PCT No.: PCT/US2017/061831
§ 371 (c)(1),
(2) Date: May 14, 2019

(87) PCT Pub. No.: WO2018/093919
PCT Pub. Date: May 24, 2018

(65) Prior Publication Data
US 2019/0330628 A1 Oct. 31, 2019

Related U.S. Application Data

(60) Provisional application No. 62/422,057, filed on Nov. 15, 2016.

(51) Int. Cl.
| | |
|---|---|
| C12N 15/11 | (2006.01) |
| C12N 15/113 | (2010.01) |
| A61K 31/13 | (2006.01) |
| A61K 31/137 | (2006.01) |
| A61K 31/194 | (2006.01) |
| A61K 31/201 | (2006.01) |
| A61K 31/713 | (2006.01) |
| A61K 33/36 | (2006.01) |
| A61K 33/40 | (2006.01) |

(52) U.S. Cl.
CPC .......... *C12N 15/113* (2013.01); *A61K 31/13* (2013.01); *A61K 31/137* (2013.01); *A61K 31/194* (2013.01); *A61K 31/201* (2013.01); *A61K 31/713* (2013.01); *A61K 33/36* (2013.01); *A61K 33/40* (2013.01); *C12N 2310/11* (2013.01); *C12N 2310/315* (2013.01); *C12N 2320/31* (2013.01)

(58) Field of Classification Search
CPC .............. C12N 15/113; C12N 2310/11; C12N 2310/315; C12N 2320/31; A61K 31/713
See application file for complete search history.

(56) References Cited

U.S. PATENT DOCUMENTS

| | | | |
|---|---|---|---|
| 2013/0324592 A1* | 12/2013 | Rodriguez Gascon | ................... A61K 48/0075 514/44 R |
| 2014/0302142 A1 | 10/2014 | Klimova | |
| 2015/0071906 A1 | 3/2015 | Liu et al. | |
| 2015/0284708 A1 | 10/2015 | Tabatadze et al. | |

FOREIGN PATENT DOCUMENTS

| | | | | |
|---|---|---|---|---|
| WO | WO-2005110477 A2 * | 11/2005 | ........... | A61K 31/282 |
| WO | WO-2008132234 A2 * | 11/2008 | ............... | A61P 31/00 |
| WO | WO-2009068033 A2 * | 6/2009 | ................ | A61P 3/00 |
| WO | WO-2013117713 A1 * | 8/2013 | ......... | C12N 15/1135 |
| WO | 2016/118697 A9 | 7/2016 | | |

OTHER PUBLICATIONS

Cao et al., SIRT1 confers protection against UVB- and H202-induced cell death via modulation of p53 and JNK in cultured skin keratinocytes, J.Cell.Mol.Med., 2009, vol. 13, 9B: 3632-3643 (Year: 2009).*
Belyaeva et al., Mitochondria as an important target in heavy metal toxicity in rat hepatoma AS-30D cells, Toxicology and Applied Pharmacology, 2008, 231: 34-42 (Year: 2008).*
Yezhelyev et al, Proton-Sponge Coated Quantum Dots for siRNA Delivery and Intracellular Imaging, JACS, 2008, 130: 9006-9012 (Year: 2008).*
Swaney et al., The effect of cationic liposome pretreatment and centrifugation on retrovirus-mediated gene transfer, Gene Therapy, 1997, 4: 1379-1386 (Year: 1997).*
Lee etal, Inhibition of androgen receptor and β-catenin activity in prostate cancer, PNAS, 2013, vol. 110, No. 39: 15710-15715 (Year: 2013).*
Ghosh et al, Nature of linkage between the cationic headgroup and cholesteryl skeleton controls gene transfection efficiency, FEBS Letters, 2000, 473, issue 3, pp. 341-344 (Year: 2000).*
Bartoli, K. M., et al., "Kinesin molecular motor Eg5 functions during polypeptide synthesis," Mol. Biol. Cell 22:3420-3430 (2011).
Bates, P. J., et al., "Antiproliferative activity of G-rich oligonucleotides correlates with protein binding," J. Biol. Chem. 274(37):26369-26377 (1999).

(Continued)

*Primary Examiner* — Ekaterina Poliakova-Georgantas
(74) *Attorney, Agent, or Firm* — Perkins Coie LLP; Lara J. Dueppen; Mengke X. McCullough

(57) ABSTRACT

Disclosed herein are methods and compositions for enhancing gene targeting. The method entails co-administrating to a cell a targeting molecule and a means of enhancing the function of the targeting molecule upon delivery to the cell. The means of enhancing the function of the targeting molecule including one or more of a stressor that induces cellular stress, a proton sponge molecule, and an endosome or lysosome inhibitor. Compositions disclosed include a targeting molecule and one or more of a stressor that induces cellular stress, a proton sponge molecule, and an endosome or lysosome inhibitor.

13 Claims, 50 Drawing Sheets
Specification includes a Sequence Listing.

(56) References Cited

OTHER PUBLICATIONS

Bergstrom, R., et al., "Transforming growth factor β promotes complexes between Smad proteins and the CCCTC-binding factor on the H19 imprinting control region chromatin," J. Biol. Chem. 285(26):19727-19737 (2010).
Blenkiron, C., et al., "Links between the oncoprotein YB-1 and small non-coding RNAs in breast cancer," PLoS One 8(11):e80171 (2013).
Buchan, J. R., et al., "Eukaryotic stress granules: The ins and out of translation," Mol. Cell. 36(6):932 (2009).
Burdick, A. D., et al., "Sequence motifs associated with hepatotoxicity of Tocked nucleic acid—modified antisense oligonucleotides," Nucl. Acids Res. 42(8):4882-4891 (2014).
Castanotto, D., et al., "CRM1 mediates nuclear-cytoplasmic shuttling of mature microRNAs," PNAS 106(51):21655-21659 (2009).
Castanotto, D., et al., "A cytoplasmic pathway for gapmer antisense oligonucleotide-mediated gene silencing in mammalian cells," Nucl. Acids Res. 43(19):9350-9361 (2015).
Castanotto, D., et al., "Protein kinase C-α is a critical protein for antisense oligonucleotide-mediated silencing in mammalian cells," Mol. Ther. 24(6):1117-1125 (2016).
Catalanotto, C., et al., "MicroRNA in control of gene expression: An overview of nuclear functions," Int. J. Mol. Sci. 17:1712 (2016).
Chen, S.J., et al., "From an old remedy to a magic bullet: molecular mechanisms underlying the therapeutic effects of arsenic in fighting leukemia," Blood 117(24): 6425-6437 (2011).
Chernukhin, I. V., et al., "Physical and functional interaction between two pluripotent proteins, the Y-box DNA/RNA-binding factor, YB-1, and the multivalent zinc finger factor, CTCF," J. Biol. Chem. 275(38):29915-29921 (2000).
Chou, T.C., et al., "Quantitative analysis of dose-effect relationships: The combined effects of multiple drugs or enzyme inhibitors," Adv. Enzyme Reg. 22:27-55 (1984).
Christensen, N. K., et al., "A novel class of oligonucleotide analogues containing 2'-O,3'-C-Linked [3.2.0]bicycloarabinonucleoside monomers: Synthesis, thermal affinity studies, and molecular modeling," J. Am. Chem. Soc. 120:5458-5463 (1998).
Dean, R. T., et al., "Effects of exogenous amines on mammalian cells, with particular reference to membrane flow," Biochem. J. 217:27-40 (1984).
Detzer, A., et al., "Cell stress is related to re-localization of Argonaute 2 and to decreased RNA interference in human cells," Nucl. Acids Res. 39(7):2727-2741 (2011).
Disterer, P., et al., "Development of therapeutic splice-switching oligonucleotides," Hum. Gene Ther. 25:587-598 (2014).
Dormann, D., et al., "ALS-associated fused in sarcoma (FUS) mutations disrupt Transportin-mediated nuclear import," EMBO J. 29:2841-2857 (2010).
Drugbank, Ambroxol, Accession No. DB06742, https://www.drugbank.ca/drugs/DB06742, retrieved Oct. 10, 2019.
Eliseeva, I. A., et al., "Y-box-binding protein 1 (YB-1) and its functions," Biochem. (Moscow) 76(13): 1402-1433 (2011).
Emde, A., et al., "miRNAs at the interface of cellular stress and disease," EMBO J. 33:1428-1437 (2014).
Fredriksson, S., et al., "Protein detection using proximity-dependent DNA Tigation assays," Nat. Biotechnol. 20:473-477 (2002).
Gagnon, K. T., et al., "RNAi factors are present and active in human cell nuclei," Cell Rep. 6(1):211-221 (2014).
Gama-Carvalho, M., et al., "The rules and roles of nucleocytoplasmic shuttling proteins," FEBS Letters 498:157-163 (2001).
Glaxosmithkline, Prosensa regains rights to drisapersen from GSK and retains rights to all other programmes for the treatment of Duchenne muscular dystrophy (DMD), Press Release, Jan. 13, 2014.
Graumann, P. L., et al., "A superfamily of proteins that contain the cold-shock domain," Trends Biochem. Sci. 23:286 (1998).

Hache, M., et al., "Intrathecal injections in children with spinal muscular atrophy: Nusinersen clinical trial experience," J. Child Neurol. 31(7):899-906 (2016).
Hansen, H. A., et al., "Influence of ammonium of growth, metabolism, and productivity of a continuous suspension Chinese hamster ovary cell culture," Biotechnol. Prog. 10:121-124 (1994).
Hansen, T. B., et al., "miRNA-dependent gene silencing involving Ago2-mediated cleavage of a circular antisense RNA," EMBO J. 30:4414-4422 (2011).
Hansen, T. B., et al., "Natural RNA circles function as efficient microRNA sponges," Nature 495:384-388 (2013).
Higashi, K., et al., "Interferon-γ interferes with transforming growth factor-β signaling through direct interaction of YB-1 with Smad3," J. Biol. Chem. 278(44):43470-43479 (2003).
Hu, J., et al., "Long-term efficacy and safety of all-trans retinoic acid/arsenic trioxide-based therapy in newly diagnosed acute promyelocytic leukemia," PNAS 106(9):3342-3347 (2009).
Huotari, J., et al., "Endosome maturation," EMBO J. 30:3481-3500 (2011).
Jeanne, M., et al., "PML/RARA oxidation and arsenic binding initiate the antileukemia response of $AS_2O_3$," Cancer Cell 18:88-98 (2010).
Jiang, B., et al., "Nucleolin/C23 mediates the antiapoptotic effect of heat shock protein 70 during oxidative stress," FEBS J. 277:642-652 (2010).
Juliano, R., et al., "Mechanisms and strategies for effective delivery of antisense and siRNA oligonucleotides," Nucl. Acids Res. 36(12):4158-4171 (2008).
Juliano, R. L., et al., "Cellular uptake and intracellular trafficking of oligonucleotides," Adv. Drug Deliv. Rev. 87:35-45 (2015).
Ka, Appendix G, Acid Dissociation Constants, W.H. Freeman, AP11-19 (2010), www.csun.edu/~hcchm003/321/Ka.pdf.
Kedersha, N., et al., "Stress granules and processing bodies are dynamically linked sites of mRNP remodeling," J. Cell. Biol. 169(6):871-884 (2005).
Kendall, G. C., et al., "Dantrolene enhances antisense-mediated exon skipping in human and muse models of Duchenne muscular dystrophy," Sci. Transl. Med. 4(164):164ra160 (2012).
Kole, R., et al., "RNA therapeutics: Beyond RNA interference and antisense oligonucleotides," Nat. Rev. Drug Discov. 11(2):125-140 (2016).
Koller, E., et al., "Mechanisms of single-stranded phosphorothioate modified antisense oligonucleotide accumulation in hepatocytes," Nucl. Acids Res. 39(11):4795-4807 (2011).
Kurreck, J., "Antisense technologies: Improvement through novel chemical modifications," Eur. J. Biochem. 270:1628-1644 (2003).
Lantz, R. C., et al., "Role of oxidative stress in arsenic-induced toxicity," Drug. Metab. Rev. 38(4):791-804 (2006).
Leucci, E., et al., "microRNA-9 targets the long non-coding RNA MALAT1 for degradation in the nucleus," Sci. Rpt. 3:2535 (2013).
Leuchowius, K.J., et al., "In situ proximity ligation assay for microscopy and flow cytometry," Curr. Protoc. Cytometry Ch. 9, Unit 9, 36 (2011).
Leung, A. K., et al., "MicroRNA functions in stress responses," Mol. Cell. 40(2):205-215 (2010).
Liang, X.H., et al., "TCP1 complex proteins interact with phosphorothioate oligonucleotides and can co-localize in oligonucleotide-induced nuclear bodies in mammalian cells," Nucl. Acids Res. 42(12):7819-7832 (2014).
Matsumoto, K., et al., "Gene regulation by Y-box proteins: coupling control of transcription and translation," Trends Cell Biol. 8:318-323 (1998).
Memczak, S., et al., "Circular RNAs are a large class of animal RNAs with regulatory potency," Nature 495:333 (2013).
Mendell, J. R., et al., "Longitudinal effect of Eteplirsen versus historical control on ambulation in Duchenne muscular dystrophy," Ann. Neurol. 79:257-271 (2016).
Ming, X., et al., "The small molecule Retro-1 enhances the pharmacological actions of antisense and splice switching oligonucleotides," Nucl. Acids Res. 41(6):3673-3687 (2013).
Misinzo, G., et al., "Inhibition of endosome-lysosome system acidification enhances porcine circovirus 2 infection of porcine epithelial cells," J. Virol. 82(3): 1128-1135 (2008).

(56) References Cited

OTHER PUBLICATIONS

Morlando, M., et al., "FUS stimulates microRNA biogenesis by facilitating co-transcriptional Drosha recruitment," EMBO J. 31:4502-4510 (2012).
Muller-Mcnicoll, M., et al., "SR proteins are NXF1 adaptors that link alternative RNA processing to mRNA export," Genes Dev. 30:553-566 (2016).
Nishi, K., et al., "Human TNRC6A is an Argonaute-navigator protein for microRNA-mediated gene silencing in the nucleus," RNA 19:17-35 (2013).
Pickering, B. F., et al., "Nucleolin protein interacts with microprocessor complex to affect biogenesis of MicroRNAs 15a and 16," J. Biol. Chem. 286(51):44095-44103 (2011).
Reyes-Reyes, E. M., et al., "A new paradigm for aptamer therapeutic AS1411 action: Uptake by macropinocytosis and its stimulation by a nucleolin-dependent mechanism," Cancer Res. 70(21):8617-8629 (2010).
Roberts, J., et al., "Efficient and persistent splice switching by systemically delivered LNA oligonucleotides in mice," Mol. Ther. 14(4):471-475 (2006).
Sasikumar, A. N., et al., "The many roles of the eukaryotic elongation factor 1 complex," Wiley Interdiscip. Rev. RNA 3(4):543-555 (2012).
Sazani, P., et al., "Nuclear antisense effects of neutral, anionic and cationic oligonucleotide analogs," Nucl. Acids Res. 29(19):3965-3974 (2001).
Sazani, P., et al., "Systemically delivered antisense oligomers upregulate gene expression in mouse tissues," Nat. Biotechnol. 20:1228-1233 (2002).
Schindler, J. F., et al., "Effects of ammonia, chloroquine, and monensin on the vacuolar apparatus of an absorptive epithelium," Cell Tissue Res. 259:283-292 (1990).
Schmierer, B., et al., "TGFβ—SMAD signal transduction: molecular specificity and functional flexibility," Nat. Rev. Mol. Cell. Biol. 8:970-982 (2007).
Schmitter, D., et al., "Effects of dicer and argonaute down-regulation on mRNA levels in human HEK293 cells," Nucl. Acids Res. 34(17):4801-4815 (2006).
Schneider, M., et al., "The importance of ammonia in mammalian cell culture," J. Biotechnol. 46:161-185 (1996).
Siomi, H., et al., "RISC hitches onto endosome trafficking," Nat. Cell. Biol. 11:1049-1051 (2009).
Soifer, H. S., et al., "Silencing of gene expression by gymnotic delivery of antisense oligonucleotides," Methods Mol. Biol. 815:333-346 (2012).
Sorokin, A. V., et al., "Proteasome-mediated cleavage of the Y-box-binding protein 1 is linked to DNA-damage stress response," EMBO J. 24:3602-3612 (2005).
Souleimanian, N., et al., "Antisense 2'-deoxy, 2'-fluoroarabino nucleic acid (2'F-ANA) oligonucleotides: In vitro gymnotic silencers of gene expression whose potency is enhanced by fatty acids," Mol. Ther. Nucl. Acids 1:e43 (2012).
Stein, C. A., et al., "Efficient gene silencing by delivery of locked nucleic acid antisense oligonucleotides, unassisted by transfection reagents," Nucl. Acids Res. 38(1):e3 (2010).
Stein, C. A., et al., "FDA-approved oligonucleotide therapies in 2017," Mol. Ther. 25(5):1069-1075 (2017).
Straarup, E. M., et al., "Short locked nucleic acid antisense oligonucleotides potently reduce apolipoprotein B mRNA and serum cholesterol in mice and non-human primates," Nucl. Acids Res. 38(20):7100-7111 (2010).
Tanaka, T., et al., "Roles of YB-1 under arsenite-induced stress: Translational activation of HSP70 mRNA and control of the number of stress granules," Biochim. Biophys. Acta 1840:985-992 (2014).
Thomas, X., et al., "Arsenic: a beneficial therapeutic poison—a historical overview," Adler Museum Bulletin 35(1):3-13 (2009).
Upadhyay, U., et al., "Ablation of RNA interference and retrotransposons accompany acquisition and evolution of transposases to heterochromatin protein CENPB," Mol. Biol. Cell 28:1132-1146 (2017).
United States Patent and Trademark Office, International Search Report and Written Opinion dated Jan. 25, 2018 for PCT/US17/61831.
Van Weert, A. W., et al., "Transport from late endosomes to lysosomes, but not sorting of integral membrane proteins in endosomes, depends on the vacuolar proton pump," J. Cell Biol. 130(4):821-834 (1995).
Wahlestedt, C., et al., "Potent and nontoxic antisense oligonucleotides containing locked nucleic acids," PNAS 97(10):5633-5638 (2000).
Weidner, D. A., et al., "Phosphorothioate oligonucleotides bind in a non sequence-specific manner to the nucleolar protein C23/nucleolin," FEBS Letters 366:146-150 (1995).
Weisz, O. A., "Acidification and protein traffic," Int. Rev. Cytol. 226:259-319 (2003).
Wilczynska, A., et al., "The translational regulator CPEB1 provides a link between dcp1 bodies and stress granules," J. Cell Sci. 118(5):981-992 (2005).
Xiao, Z., et al., "Nucleocytoplasmic shuttling of Smad1 conferred by its nuclear localization and nuclear export signals," J. Biol. Chem. 276(42):39404-39410 (2001).
Yakubov, L. A., et al., "Mechanism of oligonucleotide uptake by cells Involvement of specific receptors?" PNAS 86:6454-6458 (1989).
Yang, B., et al., "High-throughput screening identifies small molecules that enhance the pharmacological effects of oligonucleotides," Nucl. Acids Res. 43(4):1987-1996 (2015).
Zhang, X.W., et al., "Arsenic trioxide controls the fate of the PML-RARα oncoprotein by directly binding PML," Science 328:240-243 (2010).

\* cited by examiner

*\* No change in ASO uptake measured by flow cytometry analysis*

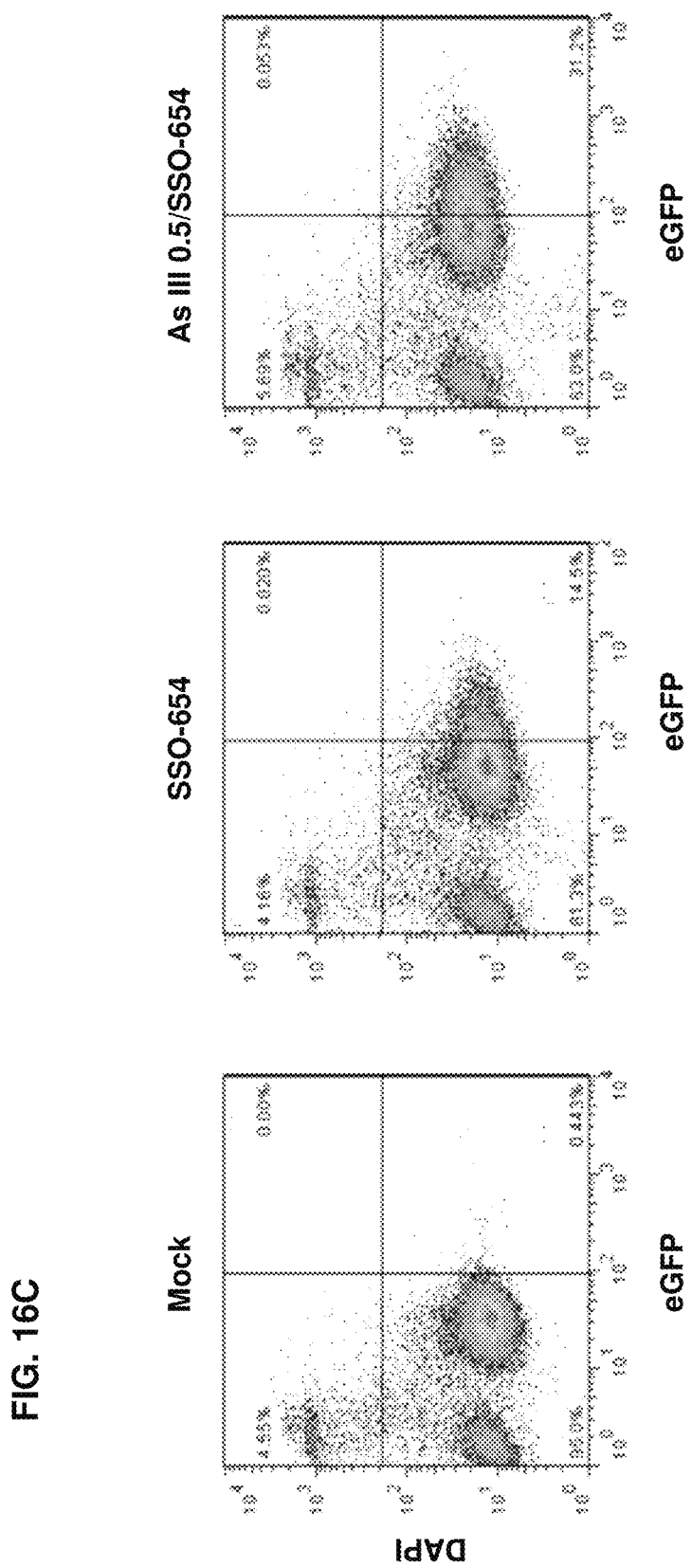

FIG. 23A
FIG. 23B
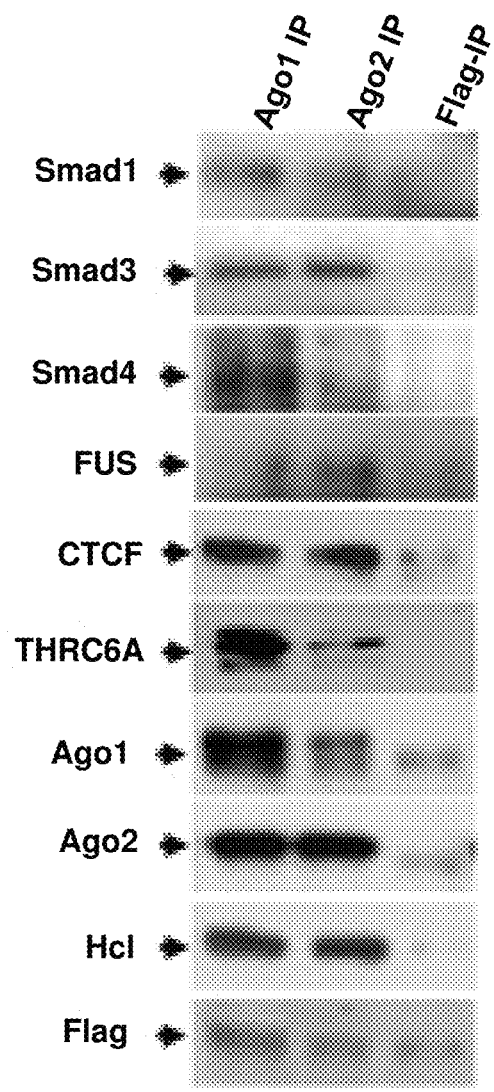
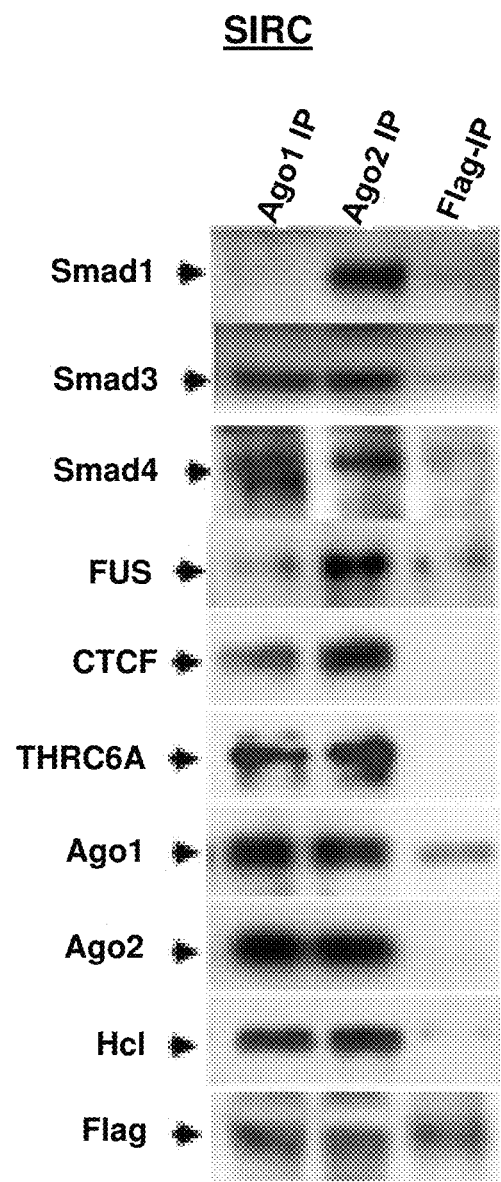

A

B

METHODS FOR INTRACELLULAR DELIVERY AND ENHANCED GENE TARGETING

PRIORITY CLAIM

This application claims priority to U.S. Provisional Application No. 62/422,057, entitled "Methods for Intracellular Delivery of Oligonucleotides," filed Nov. 15, 2016, which is incorporated herein by reference in its entirety, as if fully set forth herein.

This application contains a Sequence Listing, which was submitted in ASCII format via EFS-Web, and is hereby incorporated by reference in its entirety. The ASCII copy, created on Apr. 20, 2022, is named 8154US02_SequenceListing.txt and is 3 KB in size.

BACKGROUND

It is well established that oligonucleotides (ONs) are highly potent in the cell nucleus. MiRNAs, siRNAs and chemically modified oligonucleotides have been employed for decades for research and therapeutic purposes (1). MiRNAs, which may control the expression of more than half of all human genes, are active predominantly in the cytoplasm, but they also form complexes in the cell nuclei with components of the RNAi machinery (2). Various regulatory nuclear functions have been attributed to miRNAs and other non-coding RNA (ncRNAs), including the still-debated transcriptional gene silencing (3). Similarly, oligonucleotides delivered by gymnosis are active in the cytoplasm, but can also be transported to and are effective in the nucleus (4). As used herein, the term "gymnosis" refers to oligonucleotide delivery to cells that produces function in the absence of any carriers or conjugations. It is unclear why and how the oligonucleotides translocate to the cell nucleus since they can effectively function in the cytoplasm (4). Though several candidate proteins have been reported to bind oligonucleotides (4-6), the mechanism that determines whether an miRNA or an oligonucleotide exerts its function in the cytoplasm, or shuttles to the nucleus and acts at an earlier step in the gene regulation pathway, is unknown.

The recent FDA approval for the marketing of eteplirsen, a phosphoromorpholidate antisense oligonucleotide (ASO) (50,51), for the treatment of Duchenne's muscular dystrophy, has propelled the clinical development of splice-switching oligonucleotides (SSOs) (52). At the same time, drisapersen, a phosphorothioate (PS) SSO, which like eteplirsen was designed to produce exon skipping in the dystrophin mRNA, did not fare as well, missing its primary endpoint (the 6 minute walking test) (53). Though the use of SSOs as therapeutic molecules is promising and has shown to be well tolerated, including after multiple intrathecal administrations as in the case of nusinersen (54), their potential, as for any therapeutic antisense oligonucleotide, is hampered by substandard delivery to their targeted cells. Attempts to improve efficacy by escalating oligonucleotide doses frequently lead to unacceptable toxicity. Chemical modifications, such as locked nucleic acid (LNA) have proven to increase oligonucleotide efficacy in vivo, but the required concentrations for some therapeutic applications, depending on the oligonucleotide sequence, may also produce toxicity (55,56).

Intracellular delivery of therapeutic agents such as antisense oligonucleotides, siRNA, shRNA, miRNA, splice-switching oligonucleotides, or other small molecules is not well understood. Thus, methods and compositions for improving the efficacy of gene targeting would be desired.

SUMMARY

In certain embodiments, methods of enhancing gene targeting is provided. In one aspect such methods may include steps of administering a targeting molecule to a cell, wherein the targeting molecule binds a target molecule in the cell; and administering a stressor to the cell, wherein the stressor induces a cellular stress response; wherein co-administration of the stressor with the targeting molecule enhances the function of the targeting molecule. The method may also include a step of administering a proton sponge molecule or an endosome or lysosome inhibitor to the target cell, wherein co-administration of the proton sponge molecule or the endosome or lysosome inhibitor with the targeting molecule and the stressor further enhances the function of the targeting molecule.

In another aspect, the method may include steps of administering a targeting molecule to a cell, wherein the targeting molecule binds a target molecule in the cell; and administering a proton sponge molecule or an endosome or lysosome inhibitor to the cell, wherein co-administration of the proton sponge or the endosome or lysosome inhibitor with the targeting molecule enhances the function of the targeting molecule. The method may also include a step of administering a stressor to the target cell, wherein the stressor induces a cellular stress response, and wherein co-administration of the stressor with the targeting molecule and the proton sponge molecule or the endosome or lysosome inhibitor further enhances the function of the targeting molecule.

In some embodiments, disclosed herein are compositions that include (i) a targeting molecule, and (ii) a stressor, a proton sponge molecule or an endosome or lysosome inhibitor, both of a stressor and a proton sponge molecule, or both of a stressor and an endosome or lysosome inhibitor.

In the embodiments described herein, the targeting molecule includes an oligonucleotide, for example, an antisense oligonucleotide (ASO), an siRNA, an shRNA, or an miRNA. In certain embodiments, the antisense oligonucleotide includes a splice-switching oligonucleotide (SSO). In certain embodiments, the oligonucleotide includes a phosphorothioate oligonucleotide. In certain embodiments, the oligonucleotide includes a locked nucleic acid (LNA).

In the embodiments described herein, the stressor is capable of inducing a cellular stress, including for example, arsenic trioxide (As III or ATO), H2O2, glutathione, LIPOFECTAMINE®, or heat shock.

In the embodiments described herein, the proton sponge molecule includes an ammonium compound, such as ammonium chloride ($NH_4Cl$), ammonium hydroxide ($NH_4OH$), ammonium sulfate ($NH_4SO_4$), ammonium nitrate ($NH_4NO_3$), ammonium acetate ($NH_4CH_4CO_2$), or ammonium bicarbonate ($NH_4HCO_3$).

In the embodiments described herein, an endosome or lysosome inhibitor includes Ambroxol (Amb), Cyclohexylamine (CHA) or oleic acid (OA).

The embodiments described herein can be used to treat or research an indication that requires the targeting molecule to be delivered to the nucleus, the nucleolus, or the cytoplasm of a cell. As such, the methods described herein may include in vitro, in vivo, or ex vivo administration of (i) a targeting molecule, and (ii) a stressor, a proton sponge molecule or an endosome or lysosome inhibitor, both of a stressor and a proton sponge molecule, or both of a stressor and an endosome or lysosome inhibitor.

BRIEF DESCRIPTION OF THE DRAWINGS

FIG. 2a illustrates the procedure of immunoprecipitation (IP) and Mass Spec Analyses. FIG. 2b shows a Northern analysis of RNA extracted from the Ago1-Ago4 Immuno-Precipitates. FIG. 2c shows that Western analyses reveal the presence of nucleolin in the Ago1-Ago4 immuno-precipitates. FIG. 2d shows that Western analyses of the Ago1-Ago4 precipitates demonstrate the presence of YB-1 in the argonaute complexes.

FIG. 3a shows that the eGFP produced by the SSO when cells were previously transfected with an anti-nucleolin siRNA (si-Nd) was reduced when compared to cells transfected with a control siRNA (si-CNTR). FIG. 3b shows that this reduction in oligonucleotide function was approximately 30%. FIG. 3c shows that an anti-Ncl siRNA effectively reduces nucleolin expression also when increasing amounts of oligonucleotide are delivered to the cells, demonstrating no competition between siRNA and oligonucleotide function. FIGS. 3d and 3e show that silencing of nucleolin results in decreasing Bcl-2 targeting by a gymnotically delivered oligonucleotide.

FIG. 4a shows that a control oligonucleotide was delivered to HEK-293 cells via gymnosis. FIG. 4b shows that without doxycycline (−Dox) the LNA-ASO was localized mostly in the nuclear and peri-nuclear compartments; and in the presence of doxycyclin (+Dox), the LNA-ASO demonstrated a decreased nuclear localization and an increased cytoplasmic localization.

FIGS. 6A and 6B show immunoprecipitation with Ago-1 and Ago-2 using a YB1 antibody in the absence of any oligonucleotide (FIG. 6A) and in the presence of an oligonucleotide (LNA-ASO) (FIG. 6B). In the presence of an oligonucleotide the Ago-2/YB1 association increases (FIG. 6B).

FIG. 7a shows that the fluorescence signal detected in the sample treated with the Ago-2- and YB1-specific mixed probes but not in the controls (Flag and Lamin). FIG. 7b shows the enlargement of two panels in FIG. 7a (Ago-2/YB1 and siCntr Ago-2/YB1). FIG. 7c shows the results of a PLA assay performed with Smad-1- and Ago-2-specific mixed probes. FIG. 7c shows fluorescence signal detected in the sample treated with the Ago-2- and Smad1-specific mixed probes but not in the control (Lamin).

FIG. 11a shows the input lysates used for these experiments. FIG. 11b shows Western blot analysis shows that the immuno-precipitated YB-1 was in a complex with Ago-2 (Mock YB-1ab) and this association increased with stress caused by lipofection (Cntr-Tx YB-1ab).

FIG. 14a shows that SSO-654 was delivered by gymnosis to HeLa-EGFP-654 cells with or without As III prior to fluorescent microscopy. When As III was added ON splicing switch nuclear function was increased as shown by the increased fluorescence (compare SSO-654 to SSO-654+ As III). FIG. 14b shows Western blot analysis of HeLa-EGFP-654 treated with SSO-654 and increasing concentrations of As III, demonstrating a correlation between the increased concentration of As III and the eGFP protein produced by the SSO-654. FIG. 14c shows that an anti-eGFP ON (+ON-eGFP) was delivered by gymnosis to HeLa (top) and 293-T (bottom) cells prior to the transfection of eGFP mRNA. In this experiment the ON silenced eGFP expression in the cytoplasm (+ON-eGFP). The last panel shows As III (+ON-eGFP+ As III) treated cells and demonstrate that the ON, which partly moved to the nucleus because of the As III-induced stress signal, was less active in the cytoplasm. FIG. 14d shows that SSsi-654 was transfected to HeLa-EGFP-654 cells with or without As III (+As III) prior to fluorescent microscopy. A control non-targeting siRNA (siRNA-Cntr) is shown. Similar to ONs, splicing switch siRNA activity in the nucleus was increased by As III treatment. FIG. 14e is the graph representing the combined analysis of three different splicing switch siRNA experiments (as shown in FIG. 14d) including three technical replicates. The fluorescent signal was quantified over the entire surface of wells containing equivalent number of cells with Image Pro Premier 9.2. FIGS. 14f and 14g show that 293-T (top) and HT-1080 (bottom) cells were transfected with an anti-eGFP siRNA (siRNA-eGFP) or a non-targeting control (siRNA-Cntr). The last column shows As III treated cells (eGFP-mRNA+As III) and demonstrates that the cytoplasmic silencing function of the siRNA was decreased by As III treatment.

FIG. 15b shows Western analysis of HeLa-EGFP-654 cells treated 1 μM control ON (Cntr ON, +) or 1 μM or 2 μM SSO-654 without (−) or with (+) 1 μM As III treatment, demonstrating dose response for ON function. FIG. 15d shows eGFP intensity of cells treated as in FIG. 15b. The graph represents three biological replicates. The eGFP intensity was measured with a microplate reader (Tecan Infinite 200 PRO; Tecan Group).

FIGS. 16A-16D show that no significant changes in oligonucleotide uptake or cell viability were detected when cells were treated with oligonucleotides in combination with As III. As III does not affect the uptake of Cy5-ONs in HeLa-EGFP-654 cells (FIG. 16A) or in LNCaP cells (FIG. 16B). Cy5-ON was delivered by gymnosis to HeLa-EGFP-654 cells (FIG. 16A) or LNCaP cells (FIG. 16B) with or without As III for 12 hr prior to flow cytometry assay. FIGS. 16C and 16D show that 1 µM SSO-654 was delivered by gymnosis to HeLa EGFP-654 cells with or without As III at the indicated concentrations for 2 days. The cells were stained with DAPI prior to flow cytometric assay (FIG. 16C) or assayed by SRB staining (FIG. 16D). The data obtained from these assays was normalized to non-treated controls as 100%. Data are represented as the mean±SD, n=3. *p<0.05, **p<0.001, Students t-test.

FIG. 19c shows Northern analysis of RNA and ON extracted from YB1 Immuno-precipitated samples (YB1 IP) that were harvested from lysates of untreated (Mock) or treated (+ON) HeLa cells, demonstrating that miRNAs (miR-16 and miR-29b) were present in the YB1 IP complex and their association increased in the presence of an ON (or stress); compare+ON to Mock. The starting input for the IPs is shown. $\gamma$-$^{32}$P labeled probes were used to detect ON, miR29b and miR16 as indicated. FIG. 19e shows RT PCR detection of the reduction of miR671- and miR9-regulated nuclear RNA targets (CDR1 and Malat-1 respectively) levels in 293-T cells treated with different concentrations of 0.5 µM, 1 µM and 1.5 µM of As III, demonstrating that As III was able to direct endogenous miRNAs to the nucleus and increase their silencing function against nuclear RNA targets. Amplification of a miRNA-regulated cytoplasmic target (HDAC) was used as control and showed little change after As III treatment. FIG. 19f shows RT PCR detection of CDR1 and Malat-1 expression levels in 293-T cells treated with As III 1.5 µM and either an miR9 or an miR671 specific miRNA antagomirs demonstrating that the antagomirs were able to revert the effects of the As III proving the specificity of the mechanism. FIG. 19g shows RT PCR detection of the expression levels of the miR7 cellular targets PAX6 and CCND1 in 293-T cells treated with increasing concentrations of 0.5 µM, 1 µM and 1.5 µM of As III, demonstrating that the expression of downstream genes was also manipulated by directing the targeting miRNA to specific cellular compartment and/or by targeting miRNA sponges and releasing the miRNA of interest. Graphs represent three technical replicates. Three biological replicates were performed in triplicates for each treatment. Consistent results were obtained.

FIG. 21A shows immunofluorescence (IF) assay of HeLa-EGFP-654 cells treated with 1 µM SSO-654 spiked with 50 nM Cy5-labeled ON, with or without 1 µM As III treatment. Cells were fixed prior to Ago-2 antibody staining and Confocal Z-section imaging. Treatments are indicated in the left column. The right column in all rows shows the merged images. The top row shows Ago-2 (green) cellular distribution in absence of ON. The middle row shows Ago-2 (green) and the ON (magenta) with mostly perinuclear co-localization. This appears as a pink/white color in the merged image. The bottom column shows strong nuclear co-localization in cells in which the ON delivered by gymnosis was combined with As III treatment. Cell nuclei were stained by DAPI. The images were taken 24 hours after ON delivery. FIG. 21B shows the perinuclear localization of the ON overlaps with G3BP, a stress granule marker. The top row shows few stress granules (green) in untreated HT1080 cells (G3BP-Cntr). The second row shows mostly perinuclear co-localization of 1 µM ON (magenta) with G3BP (green). The third row shows increased co-localization and when 2 µM ON was delivered to the cells. The fourth column shows the greatest ON-G3BP perinuclear and nuclear co-localization (pink/white) following As III treatment. The right column (Merged-Z) for all rows shows a zoomed section of the merged images. All micrographs are confocal Z-section images.

FIGS. 23A and 23B demonstrates that additional proteins (such as transcription and splicing regulators YB1, CTCF, FUS and Smad1, 3 and 4) are present in the Stress Induced Response Complex (SIRC).

FIG. 26a is a schematic representation of the HeLa EGFP cell expression system used to monitor SSO-654 activity. FIG. 26b shows photomicrographs of HeLa EGPF-654 treated with non-targeting control oligonucleotide (Con-ASO), SSO-654, $NH_4^+$, a combination of Con-ASO/$NH_4^+$ or SSO-654/$NH_4^+$, as indicated. Scale Bar=100 µM. FIG. 26c shows representative Western blot assays of SSO-654-mediated GFP protein expression in HeLa EGFP-654 cells treated with SSO-654 in the presence of $NH_4^+$ at the indicated concentrations. FIGS. 26d-26f show flow cytometry assays of SSO-654-mediated EGFP expression in HeLa EGFP-654 cells. FIG. 26d shows the profiles typical of three independent experiments. FIG. 26e shows the percentage of EGFP-positive HeLa EGFP-654 cells. FIG. 26f shows the graph representing the median fluorescence of intensity (MFI) of the HeLa EGFP-654 cells shown in FIG. 26d. Data in FIGS. 26e and 26f are represented as the mean±SD, n=3. **p<0.001, Students t-test.

FIG. 28a shows that $NH_4^+$ alone at the lower concentrations of 1 mM-2 mM did not affect the growth of the HeLa EGFP-654 cells and at a higher concentration of 5 mM, $NH_4^+$ inhibited cell growth by about 15%. FIG. 28b shows that the combination of $NH_4^+$ and SSO-654 did not increase growth inhibition compared with $NH_4^+$ alone (p=0.45). Data are represented as the mean±SD, n=3. **p<0.01, Students t-test. FIG. 28c shows that the viability of HeLa EGFP-654 cells treated with SSO-654 with or without $NH_4^+$. The combination of $NH_4^+$ and SSO-654 increased the percentage of EGFP positive cells (51.2% vs 14.5% for the SSO-654 alone, lower right quadrants), but the percentage of DAPI-stained dead cells (upper left quadrants) were comparable to the single treatments or the control (3.87% vs. 4.16% for the SSO-654 alone, or 4.55% for the non-treated control).

FIGS. 29A-29B show that treatment with $NH_4^+$ facilitated ASO silencing of targeted gene protein expression in LNCaP cells. FIG. 29C shows that $NH_4^+$ facilitated ASO silencing of targeted mRNA. LNCaP cells were treated with 1 µM AR-ASO with or without 5 mM $NH_4^+$ for 24 hr; total RNA was then harvested for AR mRNA RT-PCR. Values were normalized to GAPDH mRNA expression and expressed as the mean±SD, n=3. **p<0.01, Students t-test. FIG. 29D shows the titration of AR-ASO from 0.1 JAM to 1 µM, in the presence of 5 mM $NH_4^+$ (lanes 3-6) in LNCaP cells. Lane 2 is AR-ASO at 1 µM without $NH_4^+$. FIGS. 29E and 29F show that $NH_4^+$ enhanced the efficacy of a β-Cat-ASO in the colon cancer cell lines HCT 116 (FIG. 29E) and SW 480 (FIG. 29F). HCT116 cells were treated with 1 µM β-Cat-ASO with or without 5 mM $NH_4^+$ for 2 days; SW 480 cells were treated with 0.25 µM β-Cat-ASO with or without 2 mM $NH_4^+$ for 2 days. α-Tubulin was used as control.

FIG. 30A shows that the treatment with NH4+ increased the efficacy of aBCL2-ASO in transfection-resistant Jurkat T cells. Cells were transfected with 50 nM or 100 nM BCL-2-ASO complexed with LIPOFECTAMINE®3000 (lane 2 and 3), or treated with 1 µM or 2 µM BCL2-ASO (as indicated) with or without 5 mM NH4+(lane 4-7) for 2 days, prior to being harvested for Western blots. α-Tubulin was used as control. FIG. 30B shows that the treatment with NH4+ increased BCL2-ASO efficacy in CEM T cells. The cells were treated with the indicated concentrations of the BCL2-ASO with or without 5 mM NH4+ for 2 days, prior to Western blotting. α-Tubulin was used as control.

FIG. 31a shows that $NH_4^+$ simultaneously facilitated both BCL2-ASO-mediated BCL2 silencing and SSO-654-mediated EGFP expression in HeLa EGFP-654 cells (compare lane 8 to lane 5 (GFP) and 6 (BCL2)). FIG. 31b shows the effect of SSO-654 titration (1 µM, 2 µM, and 5 µM) on BCL2-ASO activity in the presence of 5 mM $NH_4$. FIG. 31c shows the effects of increasing concentrations of BCL2-ASO at 1 µM, 2 µM and 5 µM (BCL2-1, BCL2-2, and BCL2-5, as indicated) on SSO-654 activity in the presence of 5 mM $NH_4^+$ in HeLa EGFP-654 cells. The upper profiles and graph represent the combined flow cytometric analyses of three independent experiments. The y axis of the graph indicates the MFI of the cells. Data are expressed as the mean±SD, n=3. *p<0.05, p<0.01, p<0.001, Students t-test. FIG. 31d shows that $NH_4^+$ simultaneously facilitates both f-Cat- and BCL2-ASO mediated 3-catenin and BCL2 silencing, respectively, in HCT116 cells.

FIG. 34a shows that $NH_4^+$ did not affect the uptake of a Cy5-labed ASO (Cy5-ASO) in LNCaP cells. The graph represents the Cy5 MFI from three independent experiments; data are expressed as the mean±SD. P=0.98, Student's t-test. FIG. 34b shows that $NH_4^+$ did not affect the activity of lipofected SSO-654 (Lipo-SSO-654) in HeLa EGFP-654 cells. The graph represents the EGFP MFI of HeLa EGFP-654 cells from 3 independent experiments; data are expressed as the mean±SD. P=0.87; Students t-test. FIG. 34c shows that the endosome maturation and fusion inhibitors Ambroxol (Amb), Cyclohexylamine (CHA) and oleic acid (OA) had similar effects on facilitating SSO-654 activity as $NH_4$. The graph represents the MFIs of the EGFP. Data are expressed as the mean±SD,n=3. p<0.01, *p<0.001, Student's t-test.

FIGS. 36a-36b show that the HeLa EGFP-654 cells were treated with 1 µM SSO-654 and 100 µM Amb (FIG. 36a), or 200 µM OA, alone or in combination with As III for 2 days (FIG. 36b) prior to flow cytometry. Profiles and graphs shown are typical of three independent experiments. Data are expressed as the mean±SD, n=3. **p<0.001, Student's t-test.

FIGS. 37a and 37b show microscopy (FIG. 37a) and Western blotting assays (FIG. 37b) of the cells treated with 1 µM SSO-654, and 0.5 µM As III, 5 mM $NH_4$, or both as indicated for two days prior to microscopy and Western blotting. Scale bar=100 µM. FIGS. 37c and 37d are representative experiment showing the analysis of flow cytometric data obtained from HeLa EGFP-654 cells treated as in FIGS. 37a and 37b. The profiles shown in FIG. 37c are typical of three independent experiments. The y axis of the graph in FIG. 37d represents EGFP MFIs. Data are represented as the mean±SD, n=3. **p<0.001; Students t-test. FIG. 37e shows the synergistic effect of a fixed molar ratio As III/$NH_4^+$ combination on SSO-654-mediated EGFP expression in HeLa EGFP-654 cells. CI=0.34 at the 50% effect (Fa 0.5=0.34); CI=0.20 at the 75% effect (Fa 0.5=0.20).

Figure 38:
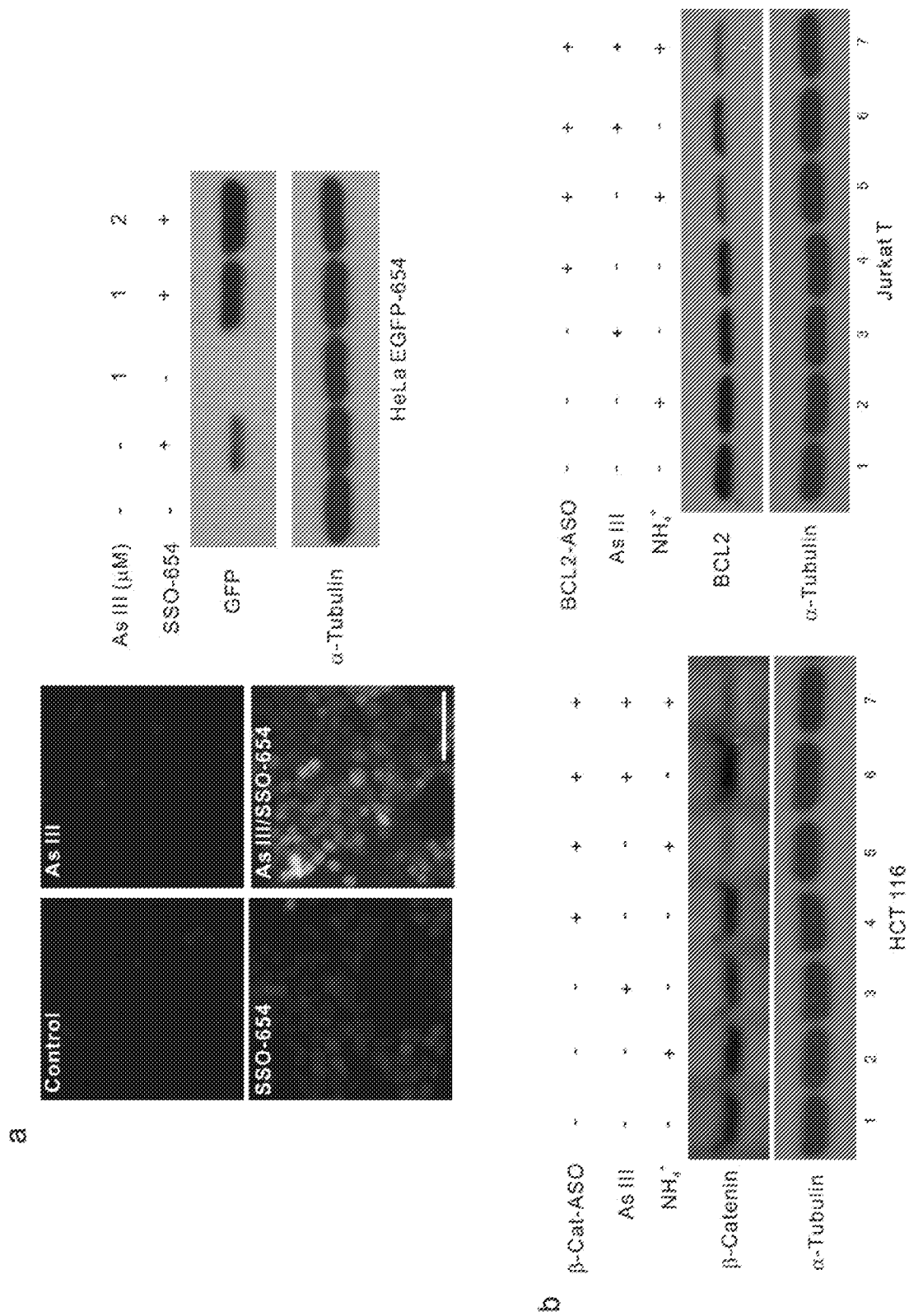

FIGS. 38a-38b show that $NH_4^+$ and As III seem to augment oligonucleotide activity by different mechanisms. FIG. 38a shows that As III, like $NH_4^+$, enhanced SSO-654 activity in HeLa EGFP-654 cells. Scale Bar, 100 μM. FIG. 38b shows that unlike $NH_4^+$, As III did not enhance the activity of ASOs in HCT116 or Jurkat T cells.

Figure 39:
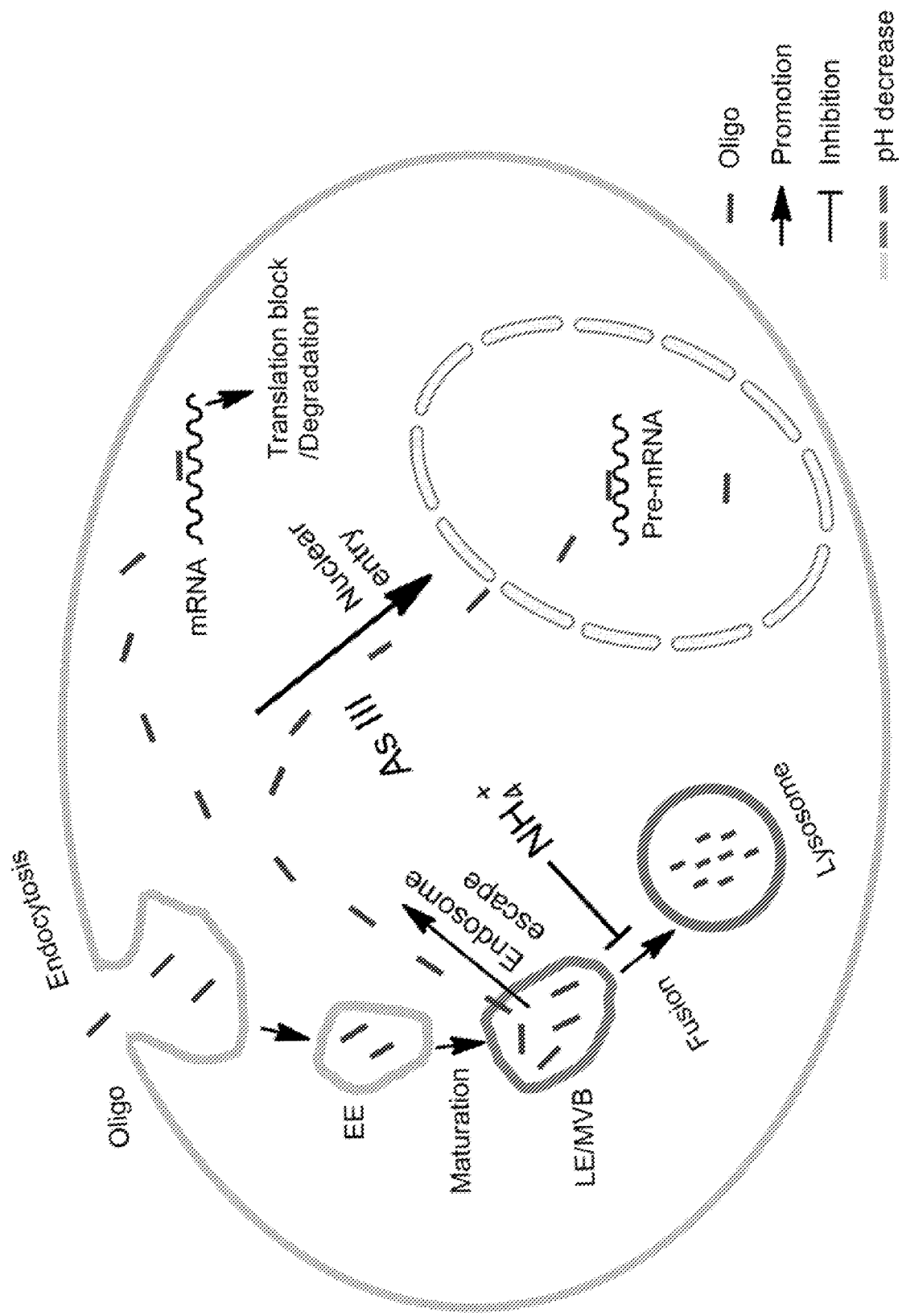

FIG. 39 illustrates a schematic model of the mechanisms leading to synergistic $NH_4^+$ and As III enhancement of oligonucleotide function.

DETAILED DESCRIPTION

Methods and compositions for intracellular delivery and enhanced gene targeting are provided herein. The methods and compositions relate to delivery of two or more molecules that, when co-administered to a cell, enhance cellular delivery and/or enhance the efficacy of one of the molecules.

In certain embodiments, a composition is provided. The composition may include two or more molecules that, when co-administered to a cell, enhance cellular delivery and/or enhance the efficacy of one of the molecules.

In one embodiment, the composition includes a targeting molecule. The targeting molecule binds a target molecule in the cell. In certain aspects, the targeting molecule suppresses the transcription or translation of the target molecule. For example, the targeting molecule may bind an mRNA molecule to suppress expression of a protein in the cytoplasm of the cell. Targeting molecules that can be used in accordance with the embodiments described herein include, but are not limited to, an antisense oligonucleotide (ASO) molecule, a splicing switch oligonucleotide (SSO) molecule, an siRNA molecule, an miRNA molecule, an shRNA molecule, or any other charged or modified small molecules. Those targeting molecules can target any molecule in the cell-in the nucleus or the cytoplasm-including, but not limited to, an mRNA molecule, an ncRNA molecule, a piRNA molecule, an miRNA molecule, a viral RNA molecule, or a promoter sequence.

The composition may also include a stressor. The stressor may include any suitable molecule that induces a cellular stress response including, but not limited to, a metabolic stressor (e.g., arsenite), a redox stressor of cells (e.g., hydrogen peroxide ($H_2O_2$) or glutathione), or other stressor (e.g., 6BIO, LIPOFECTAMINE®). In one embodiment, the stressor molecule may be arsenic (also referred to herein as arsenite or arsenic trioxide or As III or "ATO"). In some embodiments, the stressor is a heat shock. As shown in the working examples below, the combination of a targeting molecule and a stressor such as arsenic enhances delivery of the targeting molecule to the nucleus and also enhances its nuclear function.

The composition may also include a proton sponge molecule or an endosome or lysosome inhibitor. The proton sponge molecule may include any suitable proton sponge molecule including, but not limited to, ammonium ($NH_4^+$). Any suitable ammonium compound can be used, such as ammonium chloride ($NH_4Cl$), ammonium hydroxide ($NH_4OH$), ammonium sulfate ($NH_4SO_4$), ammonium nitrate ($NH_4NO_3$), ammonium acetate ($NH_4CH_4CO_2$), or ammonium bicarbonate ($NH_4HCO_3$). In some embodiments, the endosome or lysosome inhibitor includes Ambroxol (Amb), Cyclohexylamine (CHA) or oleic acid (OA).

In certain embodiments, the two or more molecules that, when co-administered to a cell, enhance cellular delivery and/or enhance the efficacy of one of the molecules, are co-administered individually instead as part of a composition. In some embodiments, a targeting molecule can be co-administered in combination with a stressor. In some embodiments, a targeting molecule can be co-administered in combination with a proton sponge molecule or an endosome or lysosome inhibitor. In some embodiments, a targeting molecule can be co-administered in combination with a stressor and a proton sponge molecule. In some embodiments, a targeting molecule can be co-administered in combination with a stressor and an endosome or lysosome inhibitor. Co-administration of these combinations can occur simultaneously, or may be spared out at a predetermined time interval.

In some embodiments, the compositions and combinations described herein may be used in research studies to treat cells in vitro. In that case, the compositions or combinations may be administered using a pipet or any other suitable method for treating cultured cells. The cells may be any suitable cultured cell, including primary cultured cells, cell lines, immortal cell lines, stem cells.

In other embodiments, the compositions and combinations described herein may be used an in vivo or ex vivo method for use in clinical research studies, animal research studies, or for treatment of a therapeutic indication. In that case, the compositions or combinations may be administered to a cell that is part of population of cells that make up an organ or tissue. For in vivo methods, the compositions and combinations may be administered to a subject (e.g., a human or an animal) orally, via injection, absorption, inhalation, or any other suitable administration method. For ex vivo methods, the cell may be found in a subject's circulation.

Also provided herein are methods for using the compositions and combinations described herein. In certain embodiments, a method of enhancing gene targeting is provided. In one aspect the method may include steps of administering a targeting molecule to a cell, wherein the targeting molecule binds a target molecule in the cell; and administering a stressor to the cell, wherein the stressor molecule induces a cellular stress response; wherein co-administration of the stressor molecule with the targeting molecule enhances the function of the targeting molecule. The method may also include a step of administering a proton sponge molecule or an endosome or lysosome inhibitor to the target cell, wherein co-administration of the proton sponge molecule or the endosome or lysosome inhibitor with the targeting molecule and the stressor further enhances the function of the targeting molecule.

In another aspect, the method may include steps of administering a targeting molecule to a cell, wherein the targeting molecule binds a target molecule in the cell; and administering a proton sponge molecule or an endosome or lysosome inhibitor to the cell, wherein co-administration of the proton sponge molecule or the endosome or lysosome inhibitor with the targeting molecule enhances the function of the targeting molecule. The method may also include a step of administering a stressor to the target cell, wherein the stressor induces a cellular stress response, and wherein co-administration of the stressor with the targeting molecule and the proton sponge molecule or the endosome or lysosome inhibitor further enhances the function of the targeting molecule.

In certain aspects, this disclosure relates to a mechanism of directing the oligonucleotides such as siRNAs and miRNAs into the nucleus. The cellular localization of the oligonucleotides, siRNAs (FIGS. 14d-14g) and endogenous miRNAs (FIGS. 19e-19g) is altered by using a cellular stress signal (e.g., As III), thereby to manipulate gene expression. For example, endogenous miRNAs can be directed to target miRNA sponges as shown in FIG. 19, resulting in the "release" of specific miRNAs of interest to allow the manipulation of downstream genes. siRNA can be directed to perform splice switching as shown in FIG. 19. Thus, in certain embodiments, this disclosure relates to a method of controlling the localization of siRNAs or endogenous miRNAs by administering a stressor, a proton sponge, or both to the cell such that the siRNAs or endogenous miRNAs translocate from the cytoplasm to the nucleus, thereby increasing their functions against their nuclear RNA targets.

This disclosure relates to compositions and methods for nuclear transport of small molecules such as oligonucleotides, siRNAs and miRNAs by induced cellular stress and the presence of proton sponges such as ammonium ($NH_4+$). Also disclosed is a stress-induced response complex (SIRC) including one or more of following proteins, e.g., Ago-1, Ago-2, and transcription and splicing regulators such as YB1, CTCF, FUS, Smad1, Smad3, and Smad4. The SIRC is capable of transporting the small molecules (e.g., oligonucleotides, siRNAs, and miRNAs) to the nucleus. The induced cellular stress can significantly increase oligonucleotide- or siRNA-directed splicing switch events and the miRNA targeting of nuclear RNAs.

Because of their charge and their ensuing ability to bind heparin-binding cellular proteins, phosphorothioate oligonucleotides (e.g., phosphorothioate, locked nucleic acid oligonucleotides) can enter cells and hijack endogenous miRNA pathways (4). MiRNAs also shuttle to and function in the nuclear compartment (3, 44). A small miRNA subset has been proven to participate in the cellular stress response (45).

As demonstrated in the working examples, the translocation of these small nucleic acids into the nucleus results from a general response to cell stress, which triggers the formation of a stress-induced response complex, the SIRC. This complex contains both shuttling and gene expression modulator proteins. An interaction between Ago-2 and YB-1 increases as a response to cell stress and leads to the translocation of the SIRC into the nucleus. The SIRC can include miRNAs and oligonucleotides; a surge in nuclear shuttling corresponds to a proportional rise in the nuclear function of oligonucleotides, siRNAs and miRNAs. The cytoplasmic function of oligonucleotides and siRNAs decline concomitantly. The loss of cytoplasmic miRNA potency is consistent with the previously observed nuclear re-localization of Ago-2 and decreased cytoplasmic RNAi linked to cell stress (46). The results demonstrated in the working examples also support the initial formation of the SIRC, including the binding to oligonucleotides and possibly to miRNAs, to be occurring in cytoplasmic stress granules (SG). The data disclosed herein helps explaining why the intracellular localization of oligonucleotides appears to be different based on the mode of delivery. Gymnosis (which by itself at lower oligonucleotide concentrations and shorter treatment times is not a significant stressor) results in predominantly perinuclear localization of the oligonucleotides. This is in contrast to LIPOFECTAMINE®, which is a potent cell stressor, and directs the oligonucleotides to the nucleus (4).

Figure 25:
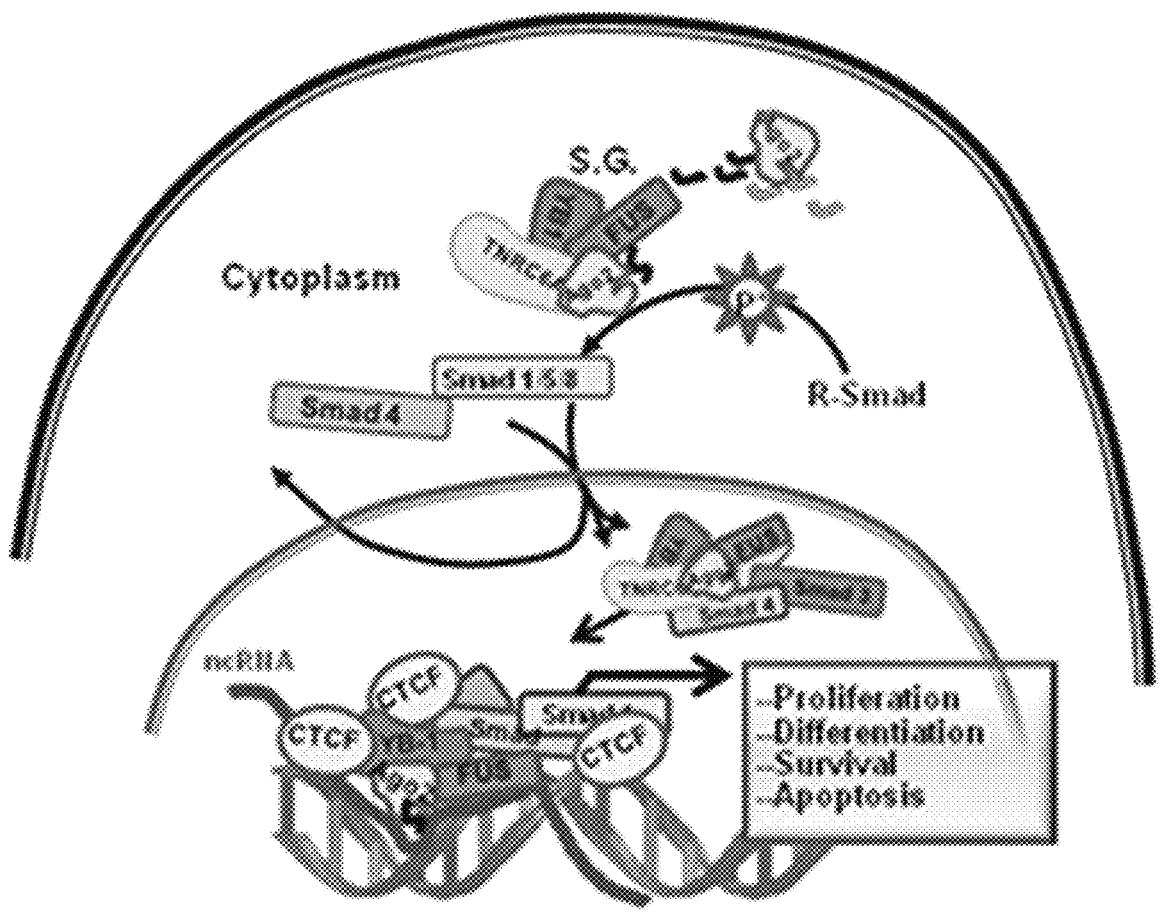
FIG. 25 shows a model in which cell stress induced by oligonucleotides and/or As III treatment leads to the formation of SG, where the interaction between the oligonucleotides, siRNAs or miRNAs with Ago-2, YB1, FUS and TNRC6A first occurs. This leads to the nuclear shuttling of the SIRC and activation (or suppression) of gene expression.

As illustrated in FIG. 25, cell stress induced by oligonucleotides (ON) and/or arsenic trioxide (As III or ATO) treatment leads to the formation of SG, where the interaction between the oligonucleotides, siRNAs or miRNAs with Ago-2, YB1, FUS and TNRC6A first occurs. Consistent with this model is the observation that the binding of FUS and TNRC6A to Ago-2 increases upon cell stress (FIG. 23). Notably, TNRC6A has been proposed to mediate miRNA-directed nuclear silencing by transporting Ago-2 to the nucleus (43) and its return to the cytoplasm via a CRM1 (ExportinI) interaction (43). It was previously reported that mature, shuttling miRNAs also return to the cytoplasm via CRM1(44). At certain concentrations and extended time point ONs will trigger stress. By adding ONs in combination with As III the concentration required to trigger stress is lowered due to the use of two agents.

Cell stress leads to phosphorylation of the R-Smads (Smad 1/5/8) and their binding to Smad-4 (28) and the SIRC, followed by the nuclear re-localization of this complex (FIG. 25). Smad-1 has also been shown to interact with CRM1 (47). Once in the nucleus, Smad-4 binds Smad-3, normally found predominantly in the nucleus. Subsequent to this binding, Smad-4 is retained in this compartment (28) together with the SIRC (FIG. 25).

Smad-1 and Smad-4 are important transcription regulators that can induce or repress a number of transcripts. These proteins together with CTCF, a master regulator of transcription, would allow the cell to have a wide-ranging stress response, which may include chromatin remodeling. The TNRC6 family contains homologies to domains of the *S. pombe* Tas3 and Chp1 proteins, which are part of the RNA-Induced Transcriptional Silencing (RITS) complex (48).

MiRNAs play crucial roles in modulating gene expression. Their deregulation has been shown to be hallmark of cancer and other diseases. As III at low concentrations is an FDA-approved anti-leukemia drug (31, 49). As disclosed herein, small, clinically relevant concentrations of As III can induce SIRC formation and can shuttle siRNAs, miRNAs and other oligonucleotides delivered by gymnosis to the cell nucleus. The potency of nuclear targeting is significantly increased by the As III treatment in consequence. Thus, this disclosure relates to a combinatorial strategy employing small nucleic acids and As III in therapeutic applications.

It was previously demonstrated that oligonucleotides delivered by gymnosis are bound by Argonaute proteins 1-4 (4), and may hijack multiple endogenous mechanisms employed by cellular miRNAs. Ago-2 binding augments oligonucleotide function, which may due to Ago-2 facilitation of oligonucleotide transport (4). Thus, Ago-2 could be part of a transport complex that differed from RISC.

To test the hypothesis that oligonucleotides were bound to an Ago-2 transport complex and to identify additional proteins belonging to this complex, immuno-precipitations (IPs) of Ago-1 or Ago-2 were performed using cell lysates harvested from HEK 293 cells that were 1) untreated; 2) treated with a control oligonucleotide delivered by gymnosis; or 3) transfected with a control siRNA. All the oligonucleotides used in the studies were phosphorothioate, locked nucleic acid oligonucleotides (PS-LNA-ONs) (7, 8), which increase stability and cellular uptake by gymnosis.

A mass spectrometric analysis of the precipitates was performed and only those proteins that were common in both lysates of cells treated with the control siRNA and lysates treated with the oligonucleotides, but were absent in all other samples and controls were analyzed. Under the experimental conditions, apart from ribosomal proteins, tubulin, and immuno-precipitated Argonautes, nudeolin, the SRSF1 and 7 splicing factors, YB-1, DbpA, PABP1, HSP-70, KIF11 and elongation factor 1 a were found. Nucleolin is a shuttling protein (9) that has been previously reported to bind oligonucleotides (5). SRSF1 and SRSF7 are members of the SR protein family, which has been shown to act on nuclear export factor 1 (NXF1) (10). The heat shock protein HSP-70 is a chaperon, stress-response protein which, among other functions, increases the stability of nucleolin during oxidative stress (11) and it is known to associate with YB-1 during stress (12). YB-1 is involved in a myriad of cellular functions; it is also a chaperon and a key player in the cellular stress response, which leads to its translocation into the nucleus (13). YB-1 is also involved in stress granule (SG) formation where it localizes (12). DbpA (YBX3) is also a Y-box binding protein (14, 15) while PABP1 binds to the mRNA poly(A) tail and is important in mRNA translation and non-sense mediated decay. PABP1 also concentrates in stress granules (16). KIF11 is a kinesin-related protein that plays a role in cell division and enhances the efficiency of mRNA translation (17). Elongation factor 1□ also plays a role in translation and, in addition, a central role in the nuclear export of proteins (18). Therefore, nearly all of the proteins identified are involved in transport and in the cellular stress response.

As demonstrated in the working examples, nucleolin and YB1 are of importance. Nucleolin is known to bind oligonucleotides (5), but has not been previously shown to bind siRNAs. However, it has been reported to interact with the microprocessor complex and to affect the processing of specific miRNAs (19).

Figure 1:
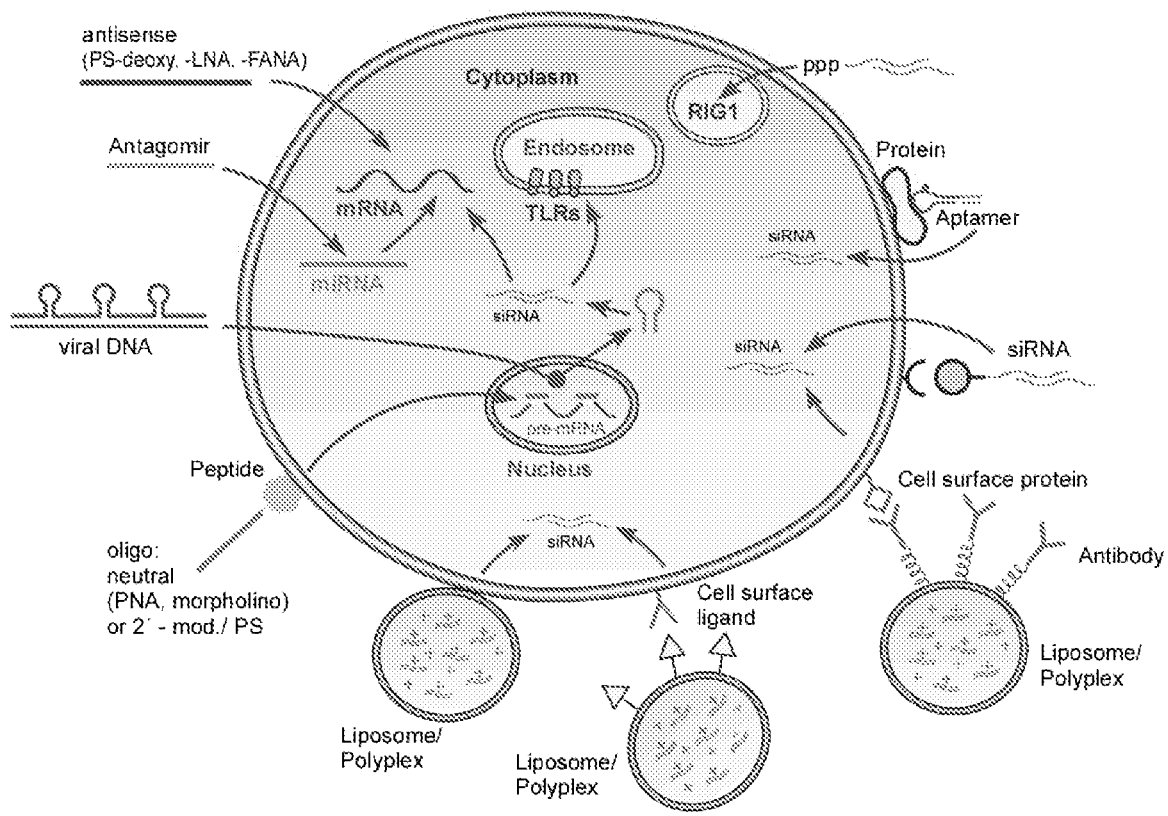
FIG. 1 is a diagram illustrating mechanisms for cellular delivery of oligonucleotides. This Figure was generously provided by Dr. F. Eckstein.
Figure 2:
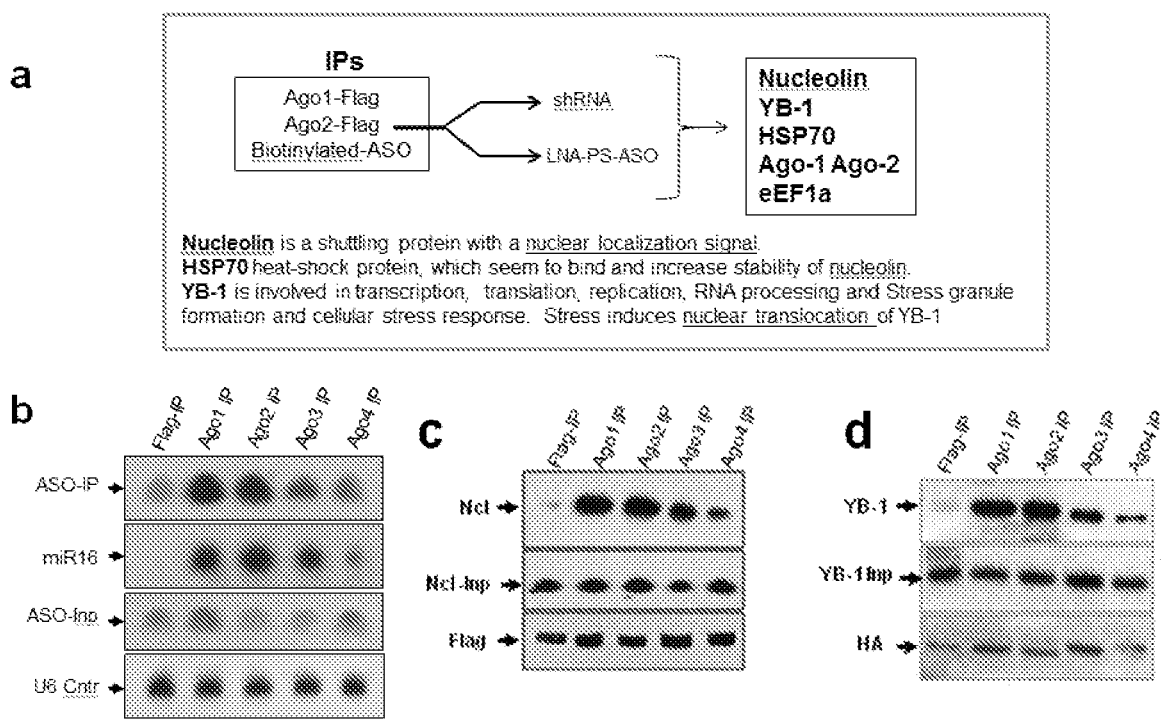
FIGS. 2a-2d show the results of Flag-immunoprecipitation protein recovery for Mass Spec Analyses.
Figure 5:
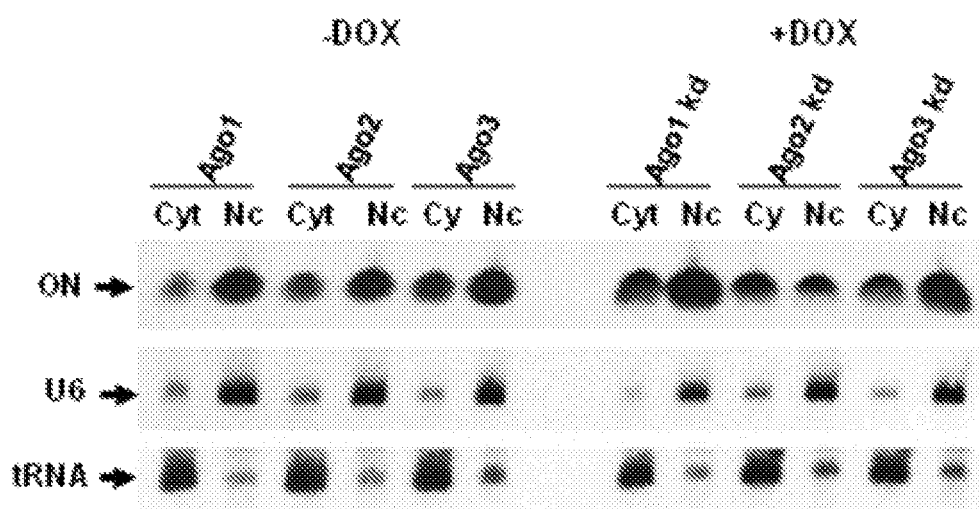
FIG. 5 shows that down-regulation of Ago-2 but not Ago-1 or Ago-3 results in oligonucleotide localization that favors the cytoplasmic compartment.

As shown in FIGS. 2c and 2d, the binding of nucleolin and YB1 to the Argonautes was confirmed by immuno-precipitation and immuno-blotting with specific antibodies. As most of the factors identified in the mass spectrometric assay, including Ago-1 and Ago-2, are known to shuttle from the cytoplasm to the nucleus (3), tetracycline (Tet) inducible stable cell lines expressing anti-Ago-shRNAs (20) were employed to study the effect of Argonaute (Ago-1, Ago-2 or Ago-3) depletion on oligonucleotide cellular localization (FIG. 5). The nuclear to cytoplasmic RNA ratio can be compared, after loading the samples, either by volume or by weight (the latter is shown in this experiment). However, it is inevitable that some of perinuclear cytoplasmic components will be precipitated with the nuclear fraction. Therefore, the nuclear and cytoplasmic fractionations shown in the working example were analyzed based on changes in the relative ratio between the two fractions, rather than on the absolute amount of signal detected in each fraction.

Down-regulation of Ago-2, but not Ago-1 or Ago-3 resulted in oligonucleotide localization that favors the cytoplasmic compartment, as shown in FIG. 5, comparing Ago2 (Dox−) with Ago2 knock-down (Ago2 kd) (Dox+), versus Ago1 or Ago3 (Dox−) with Ago1 kd or Ago3 kd (Dox+), respectively. Downregulation of the Argonautes following Tet induction in these cell lines has been previously validated (20).

Some reports have indicated an active role for nucleolin in the binding of oligonucleotides (21), but others have not been able to find a functional role for it in oligonucleotide activity (6). It is possible that nucleolin either has a redundant function, or that its contribution to ON function is measurable only in certain cell systems and under specific experimental conditions (22). Subsequent to down-regulating nucleolin expression by an siRNA approach, and consistent with these observations, only a marginal effect (up to 30%) on oligonucleotide function was detected and then only if the oligonucleotides were delivered by gymnosis rather than lipofection. Therefore the working examples focused on the role of YB1, which was also found in the Ago-ON immuno-precipitated complexes. As demonstrated below, delivery of oligonucleotides by gymnosis results in increased Ago-2/YB-1 complex formation. Moreover, Ago-2/YB-1 directly interact as a consequence of cellular stress and co-localize in the same cellular compartments.

YB1, Ago-2 and the miRNA machinery are involved in the cellular stress response (25, 26). Furthermore, YB1 has been shown to be important in the regulation of the Smad-signaling pathway (27). Smad transcription factors are a critical piece of one of the most multifaceted cytokine signaling pathways, the transforming growth factor-β pathway (28). Once activated by phosphorylation, these proteins translocate to the nucleus where they regulate gene expression (28). Therefore, they also can be potential partners of the stress-induced YB1/Ago-2 complex. As demonstrated in the working examples, Ago-2 also directly or indirectly interacts with the Smad complex.

Further, as disclosed herein, $NH_4^+$ potentiates oligonucleotide activity via a different mechanism than As II. Because two separate pathways of oligonucleotide activation seem to exist, combining both compounds (As III and $NH_4^+$), resulted in a potent synergistic increase in oligonucleotide function.

Oligonucleotide concentrations employed for therapeutic applications vary widely, but in general are high enough to raise significant concerns for off target effects and cellular toxicity. However, lowering oligonucleotide concentrations reduces the chances of a therapeutic response, since typically only relatively small amounts of oligonucleotides are taken up by targeted cells. It is therefore imperative to identify new strategies to improve the concentration dependence of oligonucleotide function.

As disclosed herein, ammonium ion ($NH_4^+$) can be used as a non-toxic potent enhancer of oligonucleotide activity in the nucleus and cytoplasm following delivery by gymnosis. Enhancement of function can be found in attached and suspension cells, including difficult-to-transfect Jurkat and CEM T cells. The working examples also demonstrate that $NH_4^+$ can synergistically interact with arsenic trioxide to further promote oligonucleotide function without yielding any apparent increased cellular toxicity. These small, inexpensive, widely distributed molecules can be used not only in laboratory experiments but potentially in therapeutic oligonucleotide-based combinatorial strategy for clinical applications.

The locked nucleic acid (LNA) modification was first synthesized by the Wengel laboratory approximately 20 years ago (57,58). Phosphorothioated (PS) oligonucleotides containing LNA moieties are not only highly resistant to nucleases, but each LNA can increase the $T_m$ of an RNA/PS LNA oligonucleotide duplex by up to 2-6° C. per residue (58,59). PS LNA oligonucleotides are active splice-switching oligonucleotides, having been shown to induce exon skipping in vivo as well as in vitro, especially in the colon, small intestine and liver (60). However, for therapeutic applications it is critically important to develop strategies that take advantage of these characteristics at low oligonucleotide doses so that the potential for off target effects are reduced.

The PS LNA SSO disclosed herein (SSO-654) is a 16mer. The LNA moieties are interspersed in the oligonucleotide chain. This substitution promotes nuclease stability and increases the stability of the oligonucleotide hybrid with the nuclear pre-mRNA. At the same time, LNA substitution blocks the induction of RNAse H activity, which would cleave the pre-mRNA and terminate exon skipping. To monitor oligonucleotide efficacy, a splice-switching model was used, in which HeLa cells have been engineered to express the enhanced green fluorescent protein (EGFP; HeLa EGFP-654) (61,62). In this model, a mutated β-globin intron has been inserted into the EGFP coding sequence to create an internal additional exon, which prevents canonical splicing and EGFP translation. Treatment of these cells with an SSO targeted to one of the internal splice sites causes exon skipping and the reconstitution of the EGFP correct reading frame (62).

The general principle that PS LNA oligonucleotides and other highly stabilized oligonucleotides such as 2'F-arabinose nucleic acids (16) can enter cells in the absence of any transfection vehicles and can also silence gene expression was previously reported (63-65). This process is called gymnosis from the Greek word for naked, and is different from the process of "free uptake" which only refers to the absence of transfection reagents (66), and has never been associated with silencing of gene expression. The process of gymnosis in tissue culture more resembles in vivo oligonucleotide uptake in saline formulations than does the process of transfection (63), and is often used for both ASO and SSO experiments.

The concentrations of oligonucleotide in the media for an optimal gymnosis experiment are often in the 250 nM-5 μM range. However, while gymnotic delivery of oligonucleotides generally results in excellent oligonucleotide function, it still can be associated with inherent potential toxicity and with sub-optimal in vivo delivery. Thus, disclosed herein are methods of improving the activity of oligonucleotides such as PS LNA oligonucleotides after gymnosis in order to improve the concentration dependence of oligonucleotide function.

It is desirable to identify small molecules that are capable of enhancing oligonucleotide functions at a low cost and that are non-toxic at the concentrations employed. However, there are very few such small molecules currently available. For example, a small molecule known as Retro-1, which reduces the toxicity of plant and bacterial compounds (67) emerged from a high throughput screen. Retro-1 enhanced both SSO and ASO efficacy when the oligonucleotides were delivered by gymnosis. However, the optimal concentration of Retro-1 was approximately 50-100 μM, and the compound is also poorly water-soluble. In a subsequent high throughput screen of >100,000 compounds, a series of 3-deazapteridine analogues were discovered (68) that at a concentration of 10 μM substantially increased SSO activity. Dantrolene (25-50 μM), a drug used clinically in the treatment of malignant hyperthermia, and other small molecules that target the ryanodine receptor have been demonstrated to promote SSO modulated exon skipping in myotubes in vitro and in mdx mice (69).

Ammonium, also approved for clinical use, considerably increases the oligonucleotides function, likely by acting as a proton sponge and aiding their endosomal release into the cytoplasm. This greatly enhances cytoplasmic gene targeting and function of the delivered molecules. Moreover, by increasing the cytoplasmic concentration of these molecules, the amount that translocates into the nucleus increases. Therefore ammonium can also increase nuclear function, although to a lesser extent when compared to As III.

As disclosed herein and demonstrated in the working examples, the ammonium ion ($NH_4^+$) can facilitate SSO activity in the HeLa EGFP-654 model in vitro, in the absence of toxicity. $NH_4^+$ also improves in vitro ASO activity both in attached suspension cells, including in Jurkat and CEM T cells, in which gene silencing has historically been difficult. Moreover, $NH_4^+$ can interact synergistically with arsenic trioxide (As III or ATO, arsenite in solution) to significantly promote oligonucleotide function in cells.

As described herein, the effects of $NH_4^+$ on the activity of oligonucleotides are studied because of the previous results (79), which highlighted the importance of endosomal maturation for oligonucleotide activity and because it has previously been shown that $NH_4^+$ affects the maturation and outcomes of late endosomes (73,74,80). After cell surface adsorption, or through fluid phase endocytosis, oligonucleotides become localized inside the cell in early endosomes. The maturation of early to late endosomes (LEs)/multivesicular bodies (MVBs) is at least in part under the control of PKC-α. Blocking PKC-α expression by a variety methods leads to a marked diminution of ASO gene silencing, suggesting that oligonucleotides, at least in part, exit the endosomal pathway at the level of the LE/MVBs. In this context, it is of interest that Ago-2, one of the proteins that interacts with oligonucleotides (81) and shuttles the oligonucleotides to the cell nucleus, can physically interact with the LE (82).

LEs/MVBs can also fuse with lysosomes; and SSO accumulation in lysosomes, a process deemed to be non-productive with respect to oligonucleotide activity, was reported (81,83). The ability of $NH_4^+$ to block or slow the fusion of LEs/MLVs with lysosomes (73,74,80) might allow the endosomal cargo to be retained for longer times in the LE/MVB, increasing its ability to exit the endosomal pathway. The exit of oligonucleotides from the endosome might also be aided by the ability of $NH_4^+$ and of other lysosomotropic weak bases, to also cause endosomal swelling (84, 85). The way that endosomal swelling is produced by $NH_4^+$ is complex, but cannot be due to proton sponge effects, as the pKa of $NH_4'$=9.26 (78), two orders of magnitude higher than the intracellular pH. The endosomal swelling effects of $NH_4^+$ may mimic those of the so-called cell penetrating peptide-oligonucleotides, in which the peptide moieties are usually short (9-30 amino acids) polypeptides that are often replete with arginines and lysines (86), both of which are organic amines.

However, the mechanism of action of $NH_4^+$, regardless of how it enhances oligonucleotides (e.g., ASO and SSO) function, appears to be different than that of As III (a mechanistic model is depicted in FIG. 39). As illustrated in FIG. 39, gymnotically delivered oligonucleotides are taken up into cells via the process of endocytosis, and are initially localized in early endosomes (EE). During the process of vesicular acidification (73-75), these EEs matures into the late endosomes/multivescicular bodies (LEs/MVBs), which will fuse with nuclease-rich lysosomes where oligonucleotides are sequestered/degraded. $NH_4^+$ inhibits endosomal acidification, causes endosomal swelling, and inhibits fusion of LEs with lysosomes. Prolonging maturation of the endosomes in addition to inhibiting fusion between later endosomes and lysosomes may facilitate the oligonucleotides escape from endosomes into the cytosol. As III, which does not appear to affect the release of oligonucleotides from the endosomal compartment, facilitates the entry of cytoplasmic oligonucleotides into the nuclear compartment via inducing a cellular stress response. Through these mechanisms, the combination of $NH_4^+$ and As III are synergistic with respect to the nuclear function of a SSO-654.

As III enhances oligonucleotide function in the nucleus but not in the cytoplasm, while $NH_4^+$ enhances function in both cellular compartments possibly by increasing the total amount of oligonucleotides released into the cytoplasm. This is in accord with the observations that As III, through induction of cellular stress, facilitates shuttling of oligonucleotides from the cytoplasm to the nucleus. In contrast to As III, under the conditions of the experiments described below, $NH_4^+$ at 5 mM, does not appear to induce a cellular stress response and thus the formation of an oligonucleotide-binding stress-induced response complex (SIRC), which consists of Ago-2, nucleolin, and Yb-1, in addition to other proteins. Furthermore, the working examples demonstrating that the higher concentrations of $NH_4^+$/As III are synergistic, as defined by the combination index (CI) method of Chou and Talalay, also suggest that these small molecules augment oligonucleotide activity by different mechanisms. The possibility that the positively charged $NH_4^+$ augments binding of an oligonucleotide to its mRNA target by charge masking may be discounted, as experiments examining the $T_m$ of DNA/RNA duplexes in the presence or absence of 5 mM $NH_4^+$ demonstrated no difference.

The combination of As III, which has previously been shown to be a potential anti-leukemia drug (87-90), and/or $NH_4^+$ (or other organic amines such as Amb., CHA and OA that act on the endosomal maturation pathway) is an easy, inexpensive, non-toxic and effective way to improve oligonucleotides, including SSO and ASO, activities after their delivery by gymnosis, even in non-attached difficult to transfect cells. Most likely, a synergistic increase in function is produced because these agents appear to be active by two different mechanisms: $NH_4^+$ seems to be acting at the level of the endosomes, while As III induces a cellular stress reaction that promotes cytoplasmic-nuclear oligonucleotide shuttling. These compounds and the mechanisms disclosed herein can be used to enhance oligonucleotide activity for therapeutic uses.

The following examples are intended to illustrate various embodiments of the invention. As such, the specific embodiments discussed are not to be construed as limitations on the scope of the invention. For example. the methods described in the working examples below may be used to enhance the efficacy of any nuclear targeting strategy, including si-RNA directed promoter methylation or activation. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

As discussed in the examples below, this work may be broadly applicable for clinical applications for the intracellular delivery of therapeutic molecules, and may also have application for the enhanced efficacy of any cellular targeting strategy, including siRNA directed promoter methylation or activation.

From the foregoing, it will be appreciated that specific embodiments of the invention have been described herein for purposes of illustration, but that various modifications may be made without deviating from the scope of the invention. Accordingly, the invention is not limited except as by the appended claims.

EXAMPLES

Materials and Methods

Cell Culture:

HeLa EGFP-654, HCT116 and SW480 cells were cultured in DMEM medium supplemented with 10% fetal bovine serum (FBS) and 2 mM L-glutamine. LNCaP cells and the Jurkat and CEM T lymphocyte cell lines were maintained in RPMI 1640 medium supplemented with 10% FBS and 2 mM L-glutamine. Cultures of all cell lines were maintained at 37° C. in a humidified 5% $CO_2$ incubator.

Reagents and Antibodies:

Ammonium chloride ($NH_4Cl$), arsenic trioxide ($As_2O_3$) and oleic acid (OA) were purchased from Sigma-Aldrich (Milwaukee, Wis.); Ambroxol hydrochloride and cyclohexylamine were from Santa Cruz Biotechnology (Santa Cruz, Calif.), as were the AR (N-20) and GFP (sc-9996) antibodies. The β-catenin antibody (4270) was purchased from Cell Signaling Technology (Danvers, Mass.) and the anti-α-tubulin antibody from Sigma-Aldrich; the anti-BCL2 antibody (clone 124) was from Dako (Santa Clara, Calif.). An arsenite solution was prepared by dissolving $As_2O_3$ in minimal volumes of 1 N sodium hydroxide (NaOH). The arsenite solution was then diluted with phosphate buffered saline to a concentration of 10 mM as a stock solution. Other compound solutions were prepared as per the manufacturer's recommendation.

Antisense Oligonucleotides:

The sequences of oligonucleotides used herein are listed in Table 1. All are phosphorothioates, with DNA given in lower case letters and LNA modifications in upper case letters. "m"=5-methylcytosine.

TABLE 1

Antisense Oligonucleotides

| Oligonucleotide Names | Target | Sequences |
|---|---|---|
| SSO-654 | Mutant β-globin | 5'-GcTaTtAcCtTaAcCc-3' (SEQ ID NO: 1) |
| Control ASO (SPC 3046) | Non Targeting | 5'-$^m$CG$^m$CAgattataaA$^m$C$^m$Ct-3' (SEQ ID NO: 2) |
| BCL2-ASO (SPC2996) | BCL-2 | 5'-$^m$CTcccagcgtgcg$^m$C$^m$Ca-3' (SEQ ID NO: 3) |
| Cy5-ASO | BCL-2 | 5'-Cy5-$^m$CTcccagcgtgcg$^m$C$^m$Ca-3' (SEQ ID NO: 4) |
| β-Cat-ASO (EZN-3889) | β-catenin | 5'-CCAtcttgtgatcCAT-3' (SEQ ID NO: 5) |
| AR-ASO (EZN-4176) | Androgen Receptor | 5'-ACCaagtttcttcAGC-3' (SEQ ID NO: 6) | m = methyl
Capital letters = LNA
All oligonucleotides are all-phosphorothioate

Western Blot:

Cells were harvested with trypsin digestion and washed once with PBS. Cell pellets were lysed in cold RIPA buffer containing protease inhibitors. Cellular RIPA lysates were sonicated for 2 seconds and then rested on ice for 5 min. Cell debris was removed by centrifugation at 12,000×g for 10 min at 4° C. Protein concentrations were determined using the Pierces BCA Protein Assay kit (Thermo Fisher Scientific, Waltham, Mass.). Aliquots of cell extracts containing 30-40 µg of protein were resolved by SDS-PAGE gel electrophoresis, and then transferred to PVDF membranes. After treatment with the appropriate primary and secondary antibodies, enhanced chemiluminescence was performed. Protein signals on the blot were quantified with the Image J program and protein expression was normalized to control=100%.

Quantitative RT-PCR:

RNA was extracted from cells using RNA-STAT 60 (AMS Biotechnology, Abingdon, UK) as recommended by the manufacturer. First-strand cDNA was synthesized with the Super-Script® III First-Strand Synthesis System Kit (Invitrogen, Carlsbad, Calif.). PCR was performed with Power SYBR GREEN PCR Master Mix (Thermo Fisher Scientific, Waltham, Mass.).

Flow Cytometry:

Cells were harvested by trypsin digestion and re-suspended in culture media or PBS buffer prior to flow cytometry. Flow cytometry data were collected by a CyAn Flow Cytometer (Beckman Coulter, Brea, Calif.), and were analyzed by the FlowJo program (Tree Star, Inc., Ashland, Oreg.) to determine fluorescence intensity vs. cell number. For cell viability assays, harvested cells were re-suspended in PBS containing 1 µg/ml DAPI (Molecular Probes, Eugene, Oreg.).

Cell Growth Assays:

Cell growth and proliferation were assayed by staining with sulforhodamine B (SRB). Briefly, cells were fixed by adding an equal volume of 10% cold trichloroacetic acid to each well. After one hour incubation at 4° C., cells were stained with 0.06% SRB for 30 min at room temperature in the dark. Cell-bound SRB was then solubilized in 10 mM Tris buffer (pH 10) and its absorbance determined at 510 nm by a microplate reader.

Statistical Analysis:

Quantifying the interaction between the oligonucleotide and ammonium and As III treatments was performed by a combination index (CI) plot using the Chou-Talalay method (70). All data are expressed as mean±standard deviation (s. d.); data from three or more independent experiments were analyzed with a two-tailed, unpaired Students t-test. $p<0.05$ was considered statistically significant.

Example 1: Stressor Molecules can Enhance the Delivery of Oligonucleotides

In this example it was determined that arsenite (a metabolic stressor), heat shock, hydrogen peroxide (a redox stressor of cells), or glutathione (a redox stressor), causes translocation of a splice switching synthetic oligonucleotide (e.g., mixer oligonucleotide, siRNA, or antisense oligonucleotide) from the cytoplasm to the nucleus. This, in the case of the splice-switching oligo, results in the increased frequency of splice switching in human tumor cell lines.

Figure 33:
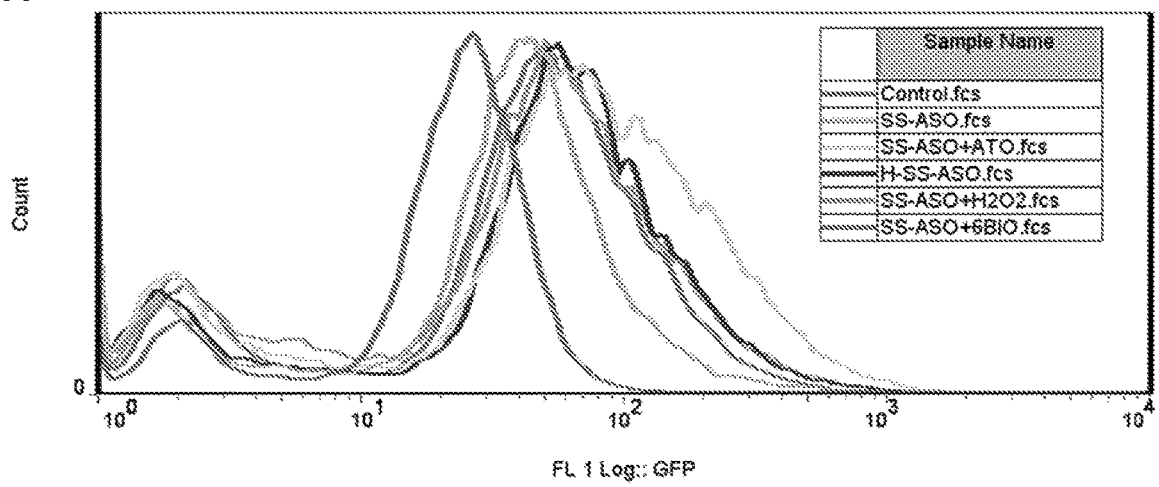
FIG. 33A is a flow-cytometry graph showing the effect of a splice switcher oligonucleotide (SS-ASO) delivered in combination with arsenite (ATO), hydrogen peroxide ($H_2O_2$), or heat shock (H) on the splice switching activity HeLa-eGFP-654 cells.
FIG. 33B shows Hela-eGFP-654 cells treated with a splice switcher oligonucleotide (SS-ASO) alone or in combination with arsenite, As III (ATO).
Figure 33:
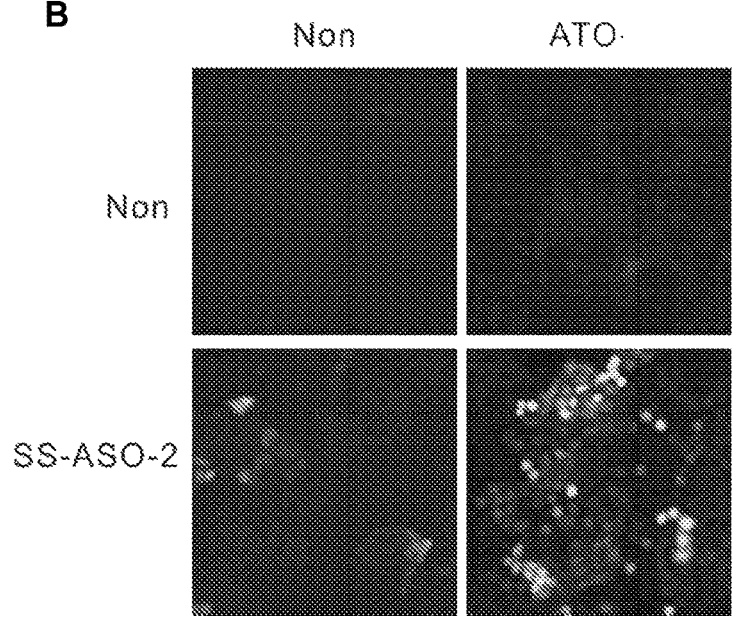

As shown in FIGS. 33A-33B, flow-cytometry analysis shows that a splice switcher oligonucleotide (SS-ASO) increased activity when delivered to cells in combination with arsenite (ATO), hydrogen peroxide ($H_2O_2$), or heat shock (H). 6BIO, a molecule that was previously found in a functional screen to strongly increase ASO activity, was used as a positive control. In this experiment, HeLa-EGFP-654 cells were treated with SS-ASO (2 µM) in the presence of 1 µM ATO, 100 µM $H_2O_2$(once), 42° C. heat shock (twice, 24 hr apart) and 2 µM 6BIO for two days. ASO activity was measured by the correctly spliced eGFP expression. All agents increased frequency of splice switching in treated cells. The extent of the increased frequency depended on the type of stressor molecule that was employed, with the most effective being arsenite, a clinical treatment for a form of human leukemia (FIGS. 33A-33B).

Example 2: Identification of the Components of a Stress Induced Shuttling Complex (SISC) that Transports Molecules into the Nucleus A Stress Induced Shuttling Complex (SISC) was identified by the studies described in this Example. The SISC can transport oligonucleotides, siRNAs, microRNAs, and other small molecules into the nucleus.

First, an LNA-PS-oligo or an siRNA was gymnotically delivered or transfected to stable cell lines expressing Ago1-Flag or Ago2-Flag and performed immuno-precipitation with the anti-Flag antibodies (FIG. 2a). The proteins recovered from the precipitates were sent for Mass Spec analyses together with proteins recovered from the parental cells transfected with a biotinylated oligonucleotide, which was then immuno-precipitated using the streptomycin beads (FIG. 2a). Only the proteins abundantly present and common for the samples containing the oligo or the siRNA, but absent in all other controls, were taken into consideration. Those are listed in the box on the right (FIG. 2a). Some ribosomal proteins, which are not pertinent to this study were also found, but are not listed. The presence of the oligo in the complex and the binding of the argonautes to some of the proteins identified in FIG. 2a was confirmed by immuno-precipitation and Northern or Western Blot analyses. FIG. 2b shows a Northern analysis of RNA extracted from the Ago1-Ago4 Immuno-Precipitates. The presence of the anti-sense oligo (ASO) was detected in the argonautes complex. The detection of miR16 was used as control for the immuno-precipitation. U6 was the control for loading and integrity of the samples. Western analyses reveal the presence of Nucleolin in the Ago1-Ago4 immuno-precipitates (FIG. 2c). The detection of Flag was used as the immuno-precipitation and loading control. Western analyses of the Ago1-Ago4 precipitates show the presence of YB-1 in the argonautes complex (FIG. 2d). HA was the immuno-precipitation and loading control.

Figure 3A:
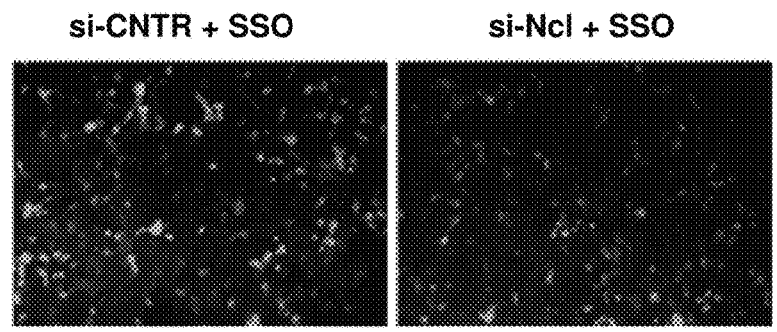
FIGS. 3a-3e show silencing of nucleolin decreases silencing of a targeted (Bcl-2) gene.
Figure 3B:
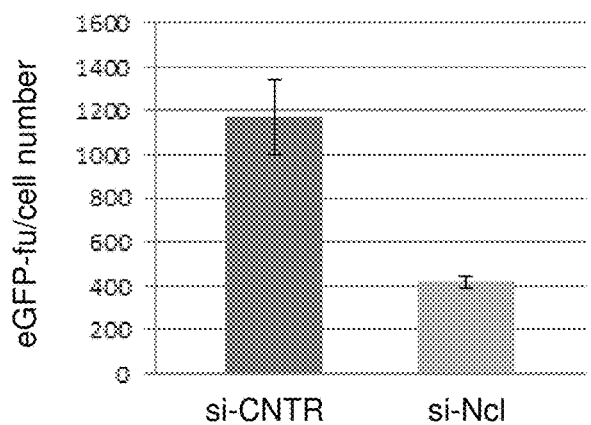
Figure 3C:
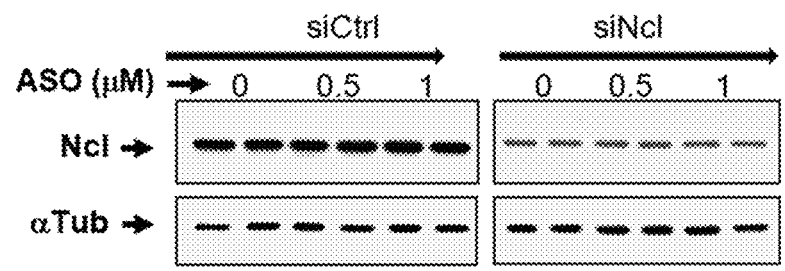
Figure 3D:
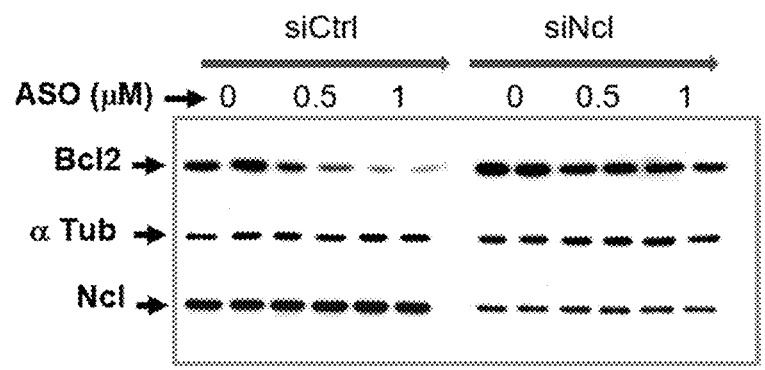
Figure 3E:
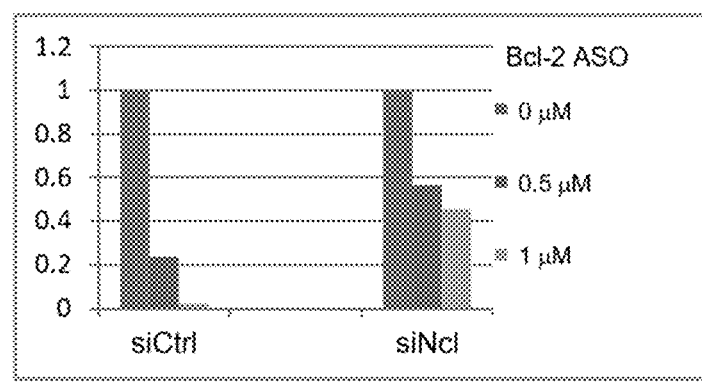

Next, it was determined that silencing of Nucleolin results in decreased oligo function. The Hela 654 eGFP used in these experiments is a stable cell line with an integrated eGFP gene whose coding sequence is interrupted by an internal exon. Therefore the eGFP protein is not expressed unless the splicing pattern is altered to exclude the internal exon and reconstitute the eGFP reading frame. The splicing switch oligo (SSO) may be used for this purpose, the amount of eGFP produced will be directly proportional to the SSO function. The eGFP produced by the SSO when cells were previously transfected with an anti-Nucleolin siRNA (si-Ncl) was reduced when compared to cells transfected with a control siRNA (si-CNTR) (FIG. 3a). This reduction in oligo function was approximately 30% (FIG. 3b). An anti-Ncl siRNA effectively reduces nudeolin expression also when increasing amounts of oligo are delivered to the cells (demonstrating no competition between siRNA and oligo function) (FIG. 3c). Silencing of nucleolin results in decrease Bcl-2 targeting by a gymnotically delivered oligo (FIGS. 3d-3e).

Figure 4:
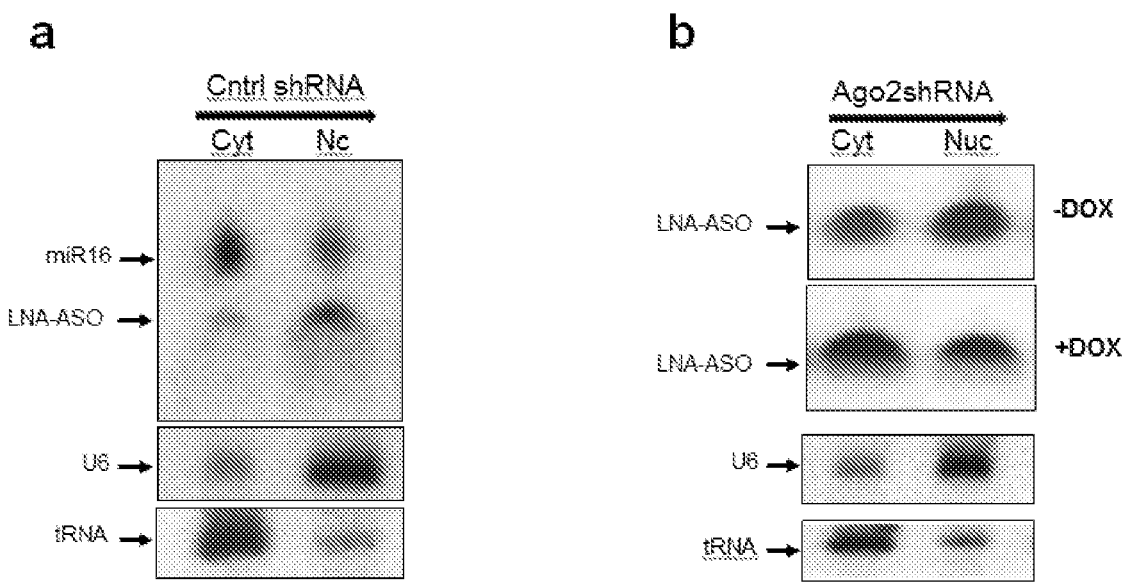
FIGS. 4a-4b demonstrate that Ago-2 is part of the nuclear LNA-ASO transport complex.

Because both Nd and YBX-1 are shuttling proteins it was investigated whether this argonaute-associated complex was involved in transporting the oligo into the nucleus. First, a control oligo was delivered to HEK-293 cells via gymnosis as shown in FIG. 4a. RNA was extracted from the nuclear and cytoplasmic fractions and gel analyzed. The oligo (LNA-ASO) shows to be mostly nuclear and perinuclear localized. miR16 was used as localization control. The U6snRNA (U6) and tRNA were used to assess the purity of the fractions. In FIG. 4b, HCT116 cells expressing a Dox-inducible Ago2 shRNA were used to analyze the role of Ago2 in the localization of the oligo. Without Doxycydine (−Dox) the LNA-ASO shows to be localized mostly in the nuclear and perinuclear compartments. However, in presence of Doxycydin (+Dox), which results in the downregulation of Ago2, the LNA-ASO shows an increased cytoplasmic localization.

Next, inducible HCT-116 cell lines expressing anti Ago1-shRNA, anti Ago2-shRNA or anti Ago3-shRNA were used to assess if other argonautes had a similar phenotype as Ago2 (FIG. 5). This fractionation in presence or absence of Dox shows that silencing of Ago1 or Ago3 does not affect the overall localization of the oligo, which remains mostly nuclear and perinuclear.

Example 3: Aao-2/YB-1 Complex Formation and Co-Localization

Figure 6:
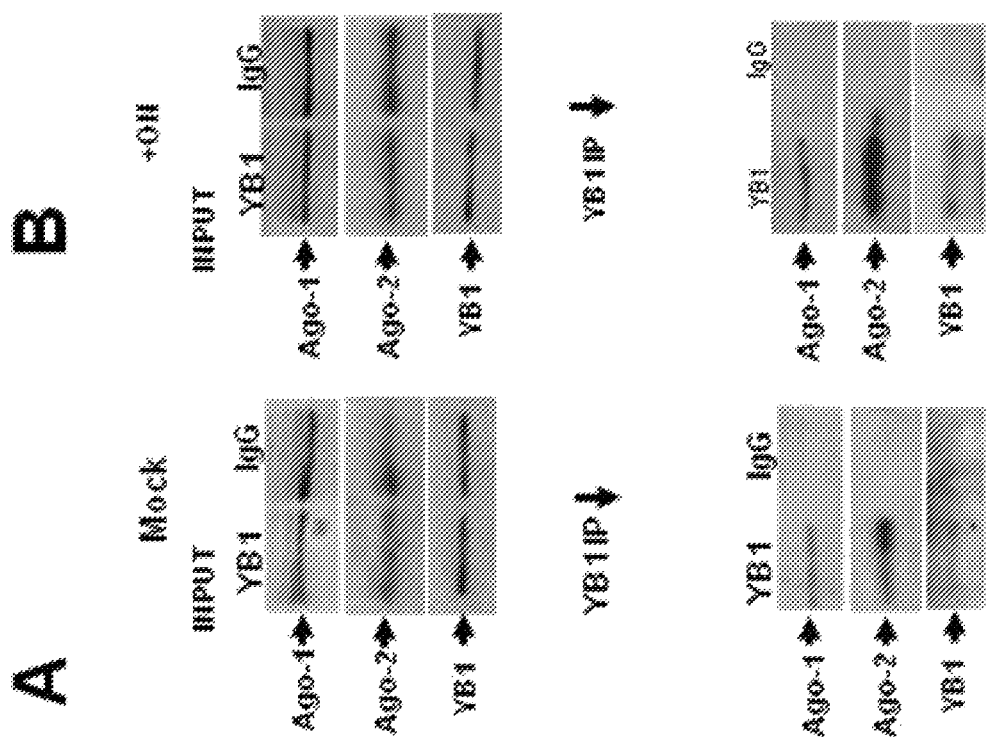
FIGS. 6A-6B demonstrate Ago-2/YB-1 complex formation.

Next, it was determined why the oligo induces formation of the SISC. Additional immuno-precipitation experiments that complemented the original Ago-IPs were performed by using HEK 293 cell lysates and a YB1 antibody to confirm 1) the interaction of YB1 with Ago-1 and/or Ago-2 (FIG. 6A); and 2) the dependence of this interaction on the presence of the oligonucleotide (FIG. 6B). Both Ago-1 and Ago-2 proteins IP$_{ed}$ with the anti-YB1 specific antibody (FIGS. 6A and 6B). Strikingly, the amount of Ago-2, but not Ago-1, in the YB1 immuno-precipitates increased when cells were treated with the oligonucleotide delivered by gymnosis (FIG. 6A bottom, compare Ago-1 and Ago-2, YB1 lane, with FIG. 6B bottom, Ago-1 and Ago-2, YB1 lane).

Specifically, it was determined whether the complex forms as a result of a stress signal (FIGS. 6A and 6B; YB-1; Immuno-precipitation (Reverse IP)). Immuno-precipitations of Ago1 and Ago2 showed the presence of YB-1 in the complex. This "reverse" immuno-precipitation using YB-1 antibodies show the presence of Ago1 and Ago2 in a YB-1 complex. FIG. 6A (top) shows the relative amount of Ago1, Ago2 and YB-1 in the lysates used for the immuno-precipitation experiments. FIG. 6B shows lysates yielded from cells treated with an oligonucleotide (+ASO). FIGS. 6A and 6B (bottom) show Western analysis of the immuno-precipitates that demonstrate the presence of Ago1 and Ago2 in the YB-1 complex. Furthermore, in presence of an oligonucleotide (ASO), the association of Ago2 with YB-1 increases. Immuno-precipitations with IgG were used as controls.

Figure 7:
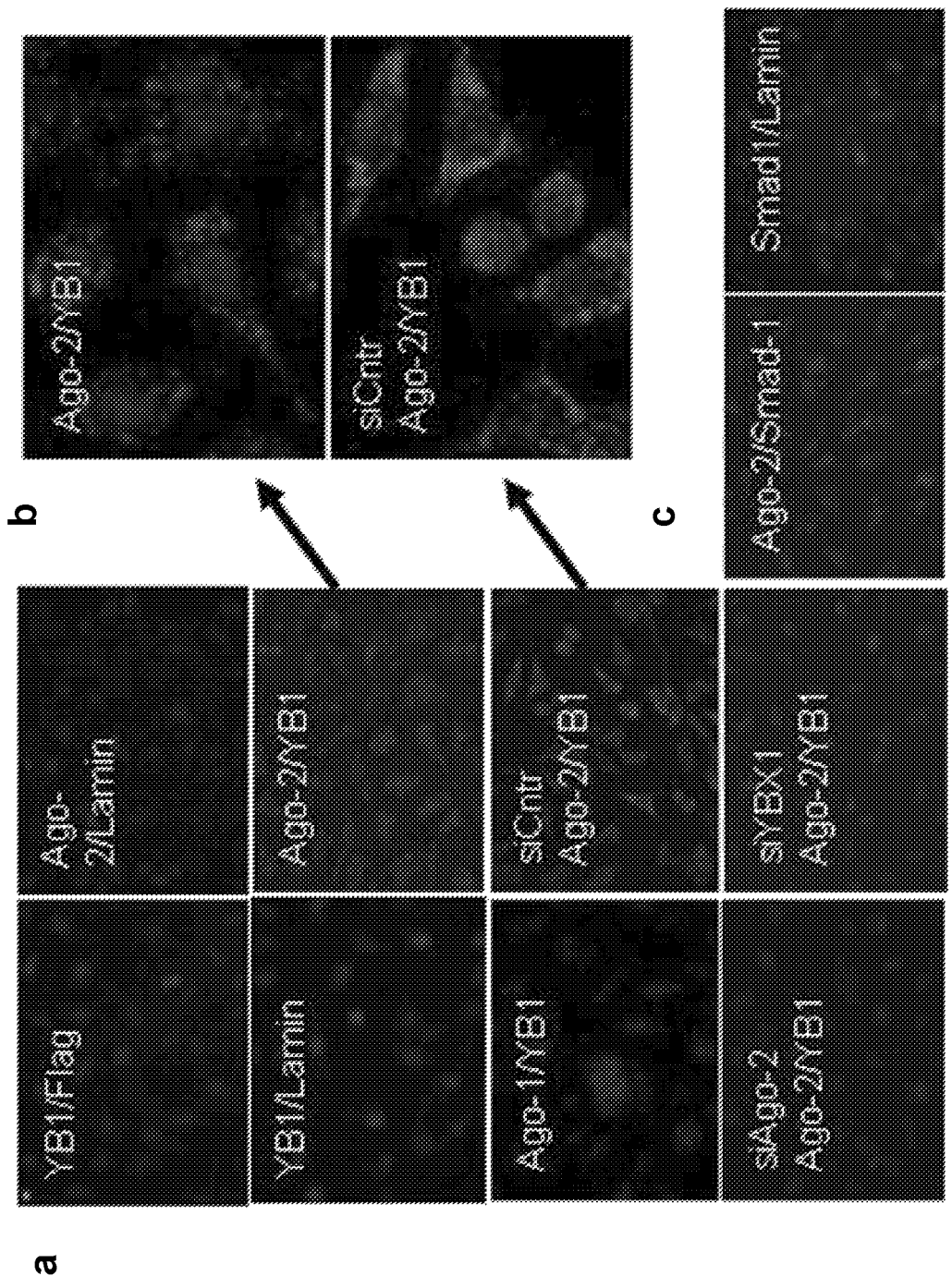
FIGS. 7a-7c demonstrate Ago-2/YB-1 and Ago-2/Smad1 complex co-localization via a PLA assay using YB1 or Smad1 and Ago-1 or Ago-2 specific primer-conjugated antibodies.

To determine whether a direct interaction between YB1 and Ago-2 occurred, a proximity ligation assay (PLA) (23, 24) was conducted using YB1 and Ago-1 or Ago-2 specific primer-conjugated antibodies (FIGS. 7a-7c). The simultaneous double recognition by the mixed probes required to obtain a fluorescence signal is highly selective and specific for protein recognition and protein-protein interaction (23, 24). The fluorescence signal in Ago2/YB-1 demonstrates the cellular co-localization of these two proteins. The Flag antibodies and the Lamin antibodies were used as controls with the YB-1 and Ago-2 antibodies to demonstrate the specificity of the detected fluorescence signal. The fluorescence signal detected in the sample treated with the Ago-2- and YB1-specific mixed probes (FIG. 7a, Ago2/YB1), but not in the controls (FIG. 7a, anti-YB1 and anti-flag antibodies (YB1/Flag), anti-Ago2 and anti-lamin antibodies (Ago2/Lamin), and anti-YB1 and anti-Lamin antibodies (YB1/Lamin)) supported a direct interaction between Ago-2 and YB1 and demonstrated intracellular co-localization in the perinuclear region and in the cell nucleus (FIGS. 7a and 7b). The signal, when the anti-Ago-1 and anti-YB1 specific mixed-probes were employed, was present but reduced (FIG. 7a, compare Ago2/YB1 to Ago1/YB1). This supports that this is a close, though perhaps not a direct interaction, but one which may be bridged by Ago-2.

A more intense fluorescent signal was detected for the Ago2/YB1 interaction in the siRNA control sample (siCntr Ago2/YB1), which underwent transfection. Following this stress signal that was triggered by lipofection, an increased interaction between these two proteins was observed, consistent with the IP results (FIGS. 6a and 6b). This Ago-2/YB1 interaction also result in an increased nuclear accumulation of this complex in nuclear speckles, as seen in FIG. 7b, which shows a magnified view of the Ago2/YB1 PLA results with or without transfection of the siRNA control.

To determine if Ago-2 also interacts with the Smad complex, a PLA assay was performed with Smad-1- and Ago-2-specific mixed probes. The fluorescent signal detected (FIG. 7c) supports that a direct or indirect interaction is occurring.

Figure 8:
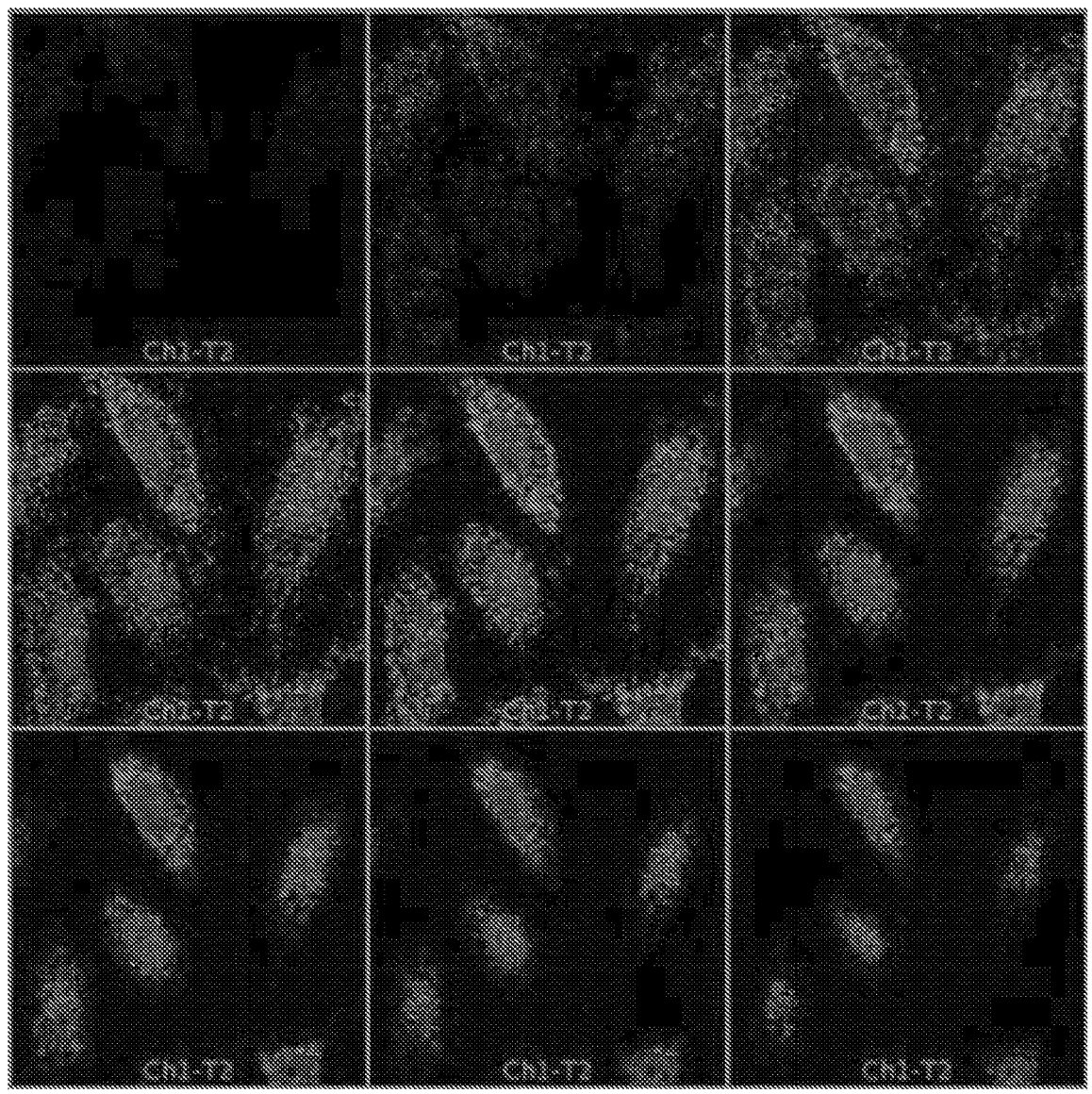
FIG. 8 shows confocal sections showing Ago2/YB-1 cellular co-localization.

Confocal sections of the cells analyzed via PLA with YB-1 and Ago2 antibodies demonstrate co-localization of these two proteins in the cytoplasm and in the nuclear compartments (FIG. 8).

Figure 9A:
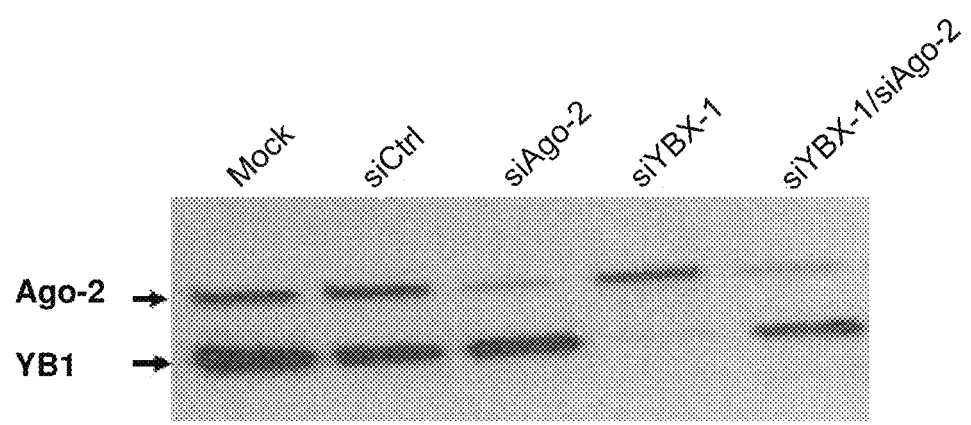
FIGS. 9A and 9B show a Western analysis (FIG. 9A) and an RNA qPCR analysis (FIG. 9B) of the cells treated with the specific Ago2 or YB-1 siRNAs or the control non-targeting siRNA (siCtrl or siCntrl).
Figure 9B:
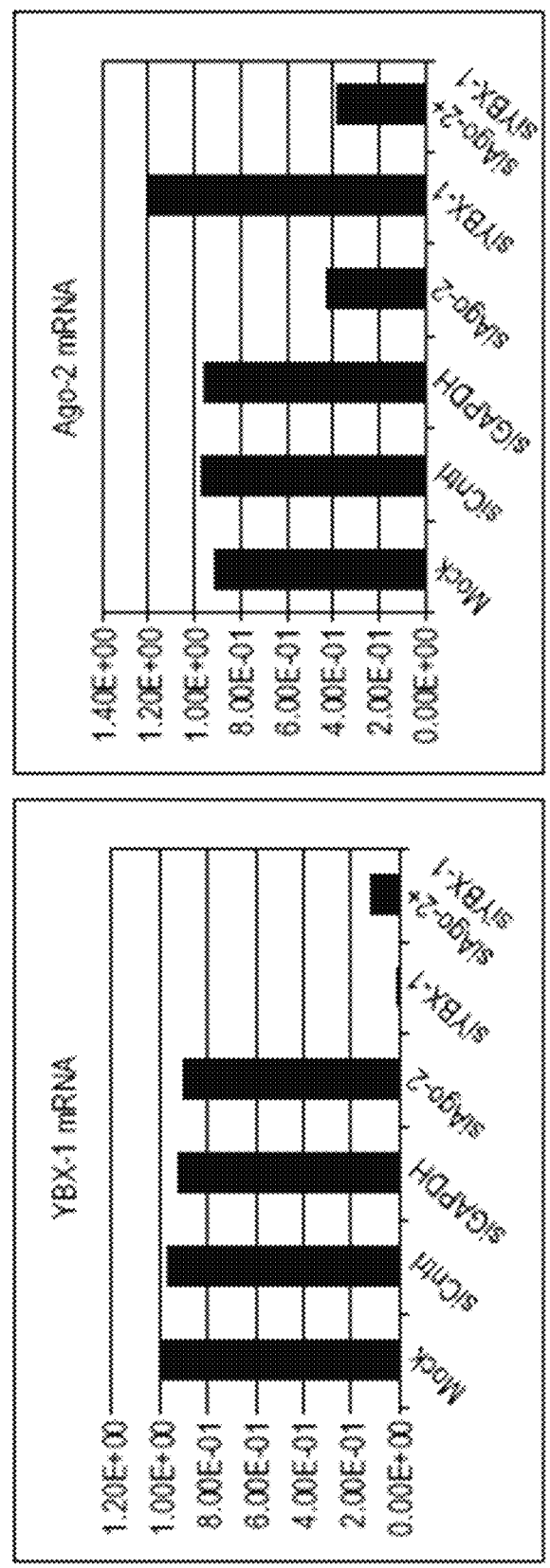

To further validate the specificity of the PLA assay and the reliability of these results, Ago-2 and/or YBX-1 (the gene producing YB1) expression was silenced with specific siRNAs (siAgo-2 and siYBX-1; FIGS. 9A and 9B). Downregulation of these genes was verified by Western (FIG. 9A) and qPCR analyses (FIG. 9B) prior to performing the PLA assay. Fluorescent signal was lost (FIG. 7a) when the expression of either (FIG. 7c) or both of these proteins (Ago-2 and YB1) was silenced (FIG. 7c; compare Ago-2/YB1 and siCntr Ago-2/YB1 with siAgo-2 Ago2/YB1, siYBX1 Ago-2/YB1 and siAgo-2/siYBX-1, Ago-2/YB1).

Figure 10:
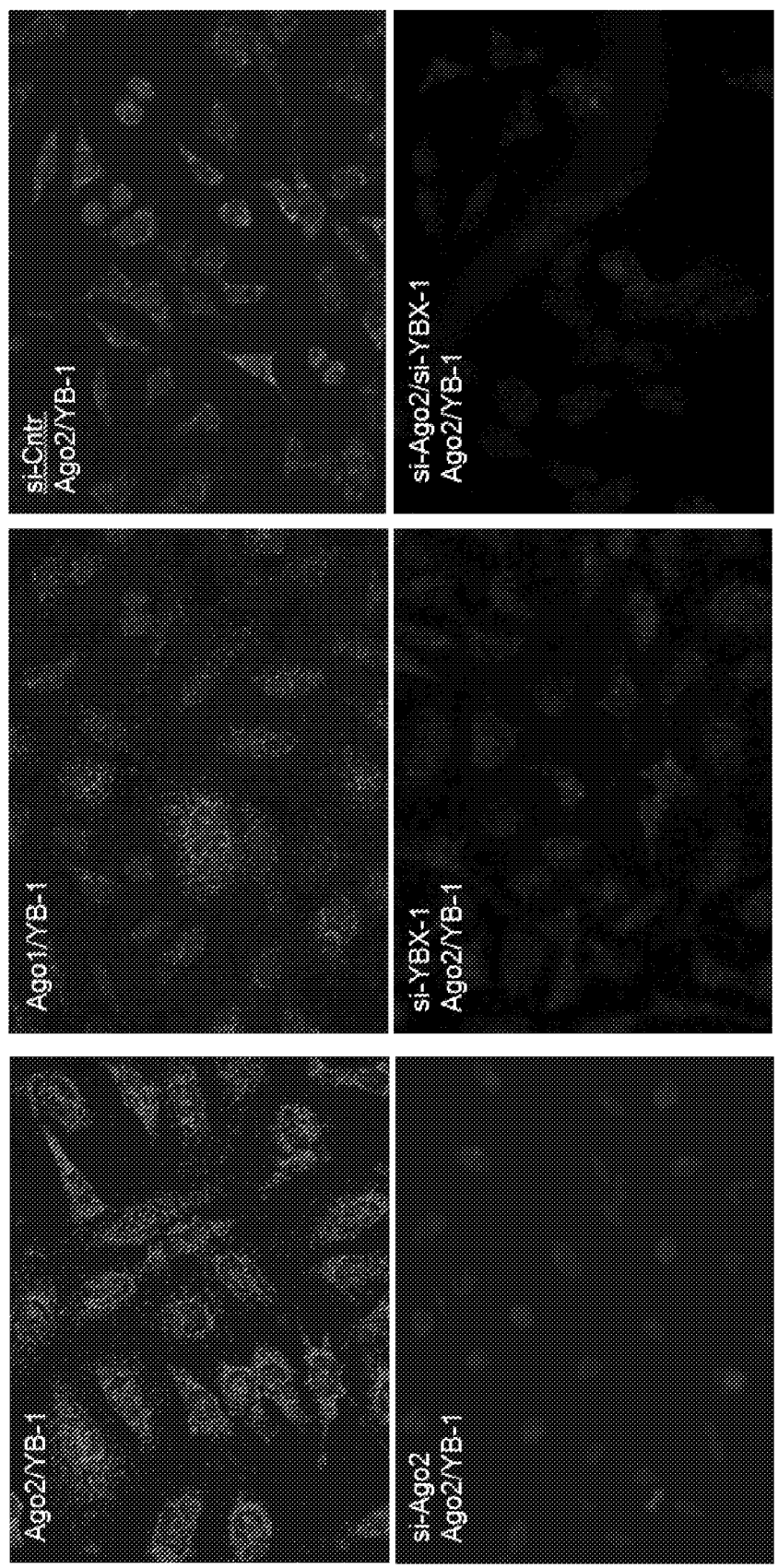
FIG. 10 shows that Ago2 is the primary argonaute interacting with YB-1.

Silencing of Ago2 or YBX-1 results in a loss of the fluorescent signal generated via PLA using specific Ago2 and YB-1 antibodies. FIG. 10 shows an additional demonstration of the specificity of the fluorescence signal and it confirms that these two proteins co-localize in the nuclear and cytoplasmic compartments. The lower signal detected by using YB-1 and Ago1 antibodies indicates that the Ago1 antibodies may not be as good as the Ago2 counterparts and/or that the Ago1 interaction with YB-1 is not direct.

Figure 11:
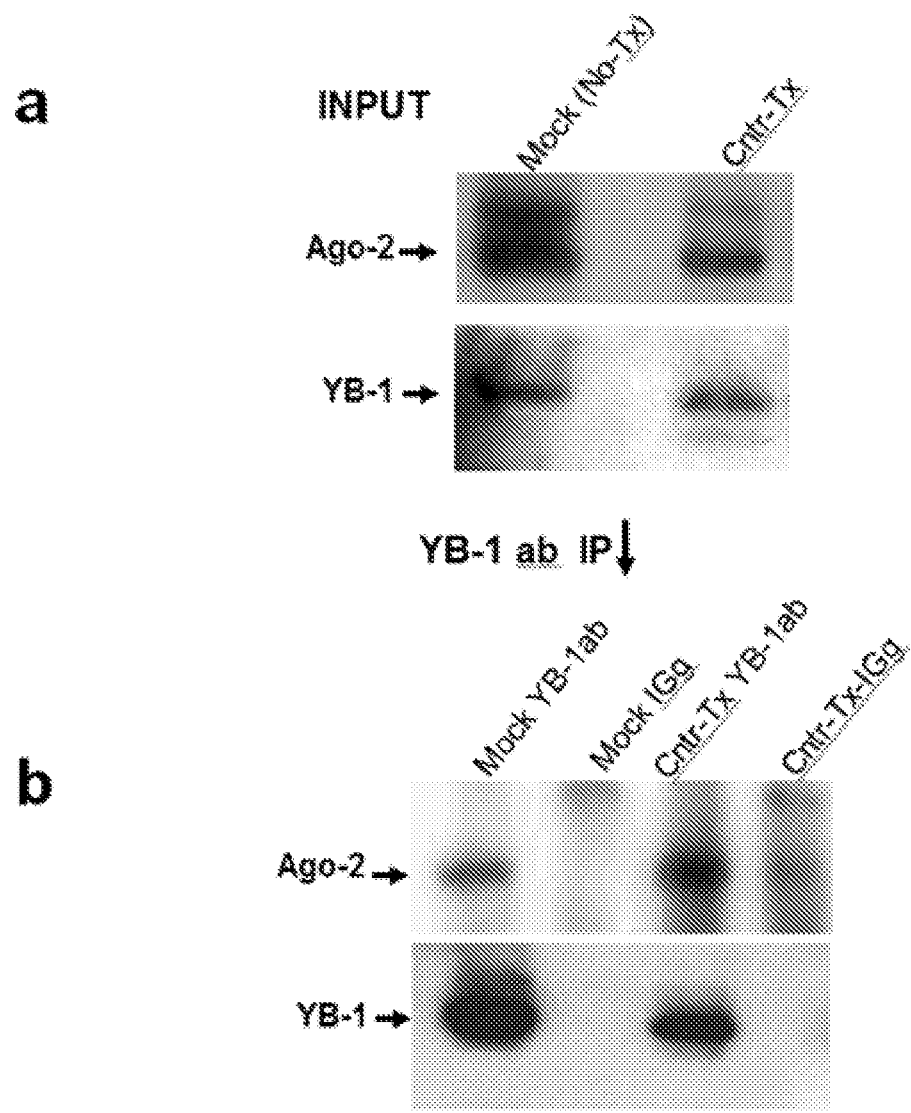
FIGS. 11a and 11b show that lipofection increased Ago2 association with YB-1.

To examine if the interaction between Ago2 and YB1 was a general response to stress or specific only to the delivery of siRNA and oligonucleotides, YB1 IPs were performed after lipofecting an empty plasmid backbone into HEK-293 cells (FIG. 11). Lipofection alone was sufficient to increase the association of Ago2 and YB1 (FIG. 11, compare the ratios between the immuno-precipitated YB1 and the amount of bound Ago2 in the Mock (Mock YB-1ab) vs. the control, transfected cells (Cntr-Tx YB-1ab)).

More specifically, to test if the intracellular delivery of the oligonucleotide is specifically required to induce the increased association of Ago2 to the YB-1 complex or if it is the result of a general stress signal (triggered by the oligo), a control vector (Cntr-Tx) was transfected and a YB-1 immuno-precipitation was performed. Similar to what was observed in presence of the oligonucleotide, ASO, the Ago2 association to YB-1 increased in the transfected (stressed) cells (See FIG. 11b, compare Mock YB-1ab and Cntr-Tx YB-1ab). Detection of YB-1 was used as control to quantify the initial amount of YB-1 in the input lysates (FIG. 11a) and the immuno-precipitated amount of YB-1 protein in the samples analyzed (FIG. 11b). Ago2 detection was stronger in the transfected cells (See FIG. 11b, compare Ago2 detection in Mock YB-1ab versus Ago2 in Cntr-Tx YB-1ab) despite less YB-1 protein was immuno-precipitated from those cells (See FIG. 11b, compare YB-1 detection in Mock YB-1 ab versus YB-1 in Cntr-Tx YB-1ab).

Figure 12:
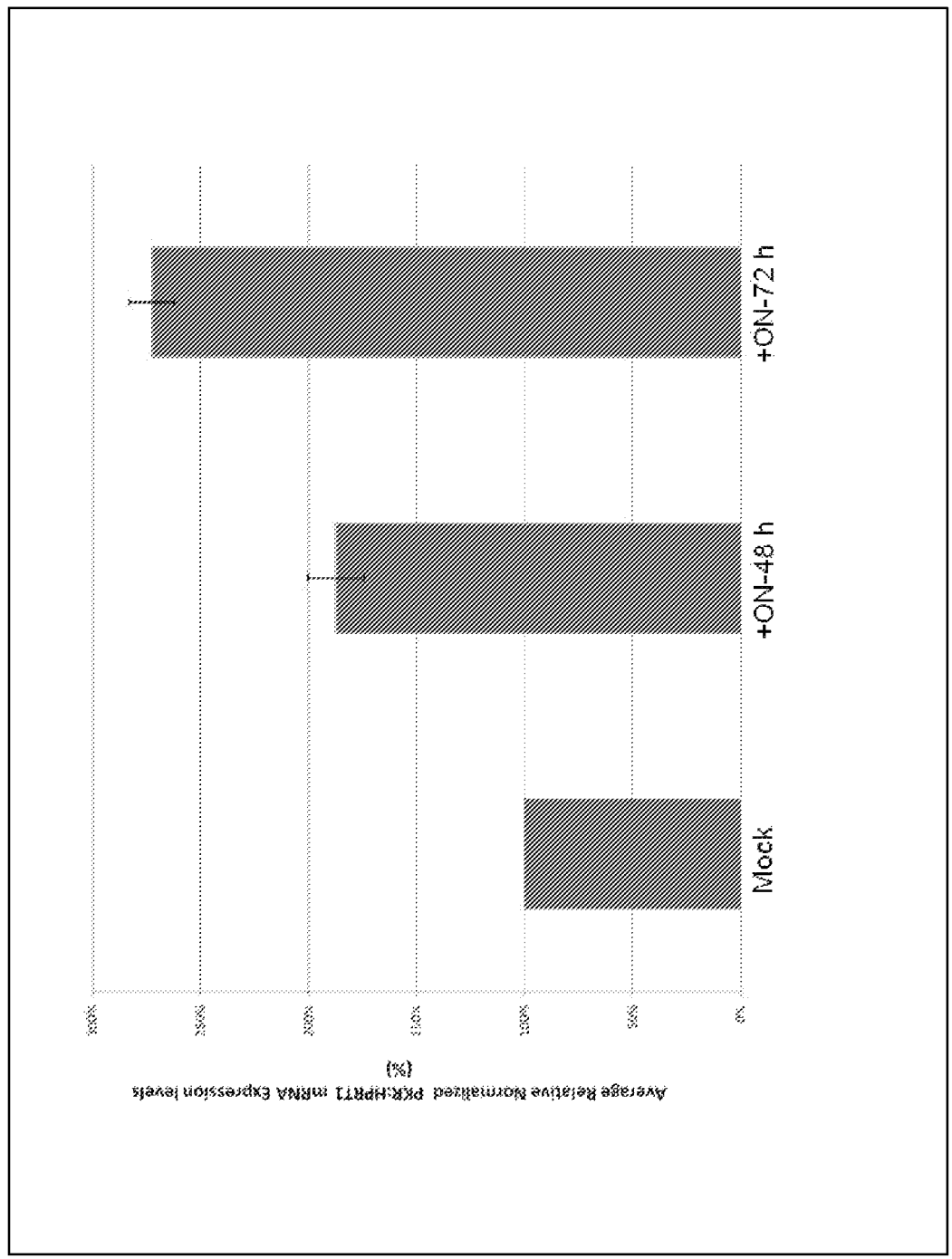
FIG. 12 shows that the delivery of oligonucleotides by gymnosis triggered an increase in PKR expression as a function of time and oligonucleotide concentration.

Then, PKR activation was examined under the experimental conditions. The delivery of oligonucleotides by gymnosis triggered an increase in PKR expression as a function of time and oligonucleotide concentration (FIG. 12).

Figure 13:
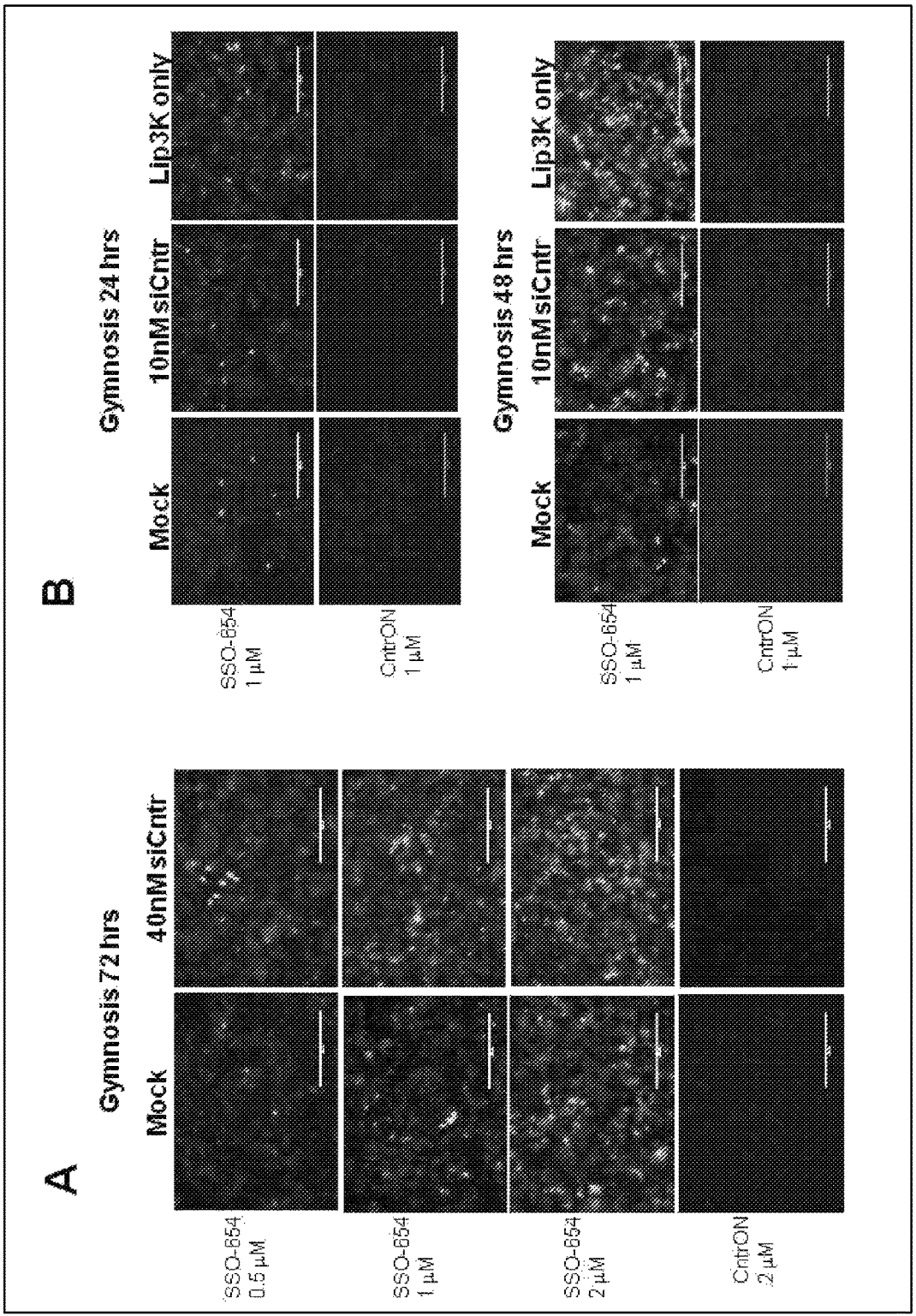
FIG. 13A shows that oligonucleotide function in the nucleus increases following transfection-induced stress.
FIG. 13B shows that a stressor siRNA molecule or uncomplexed LIPOFECTAMINE® can increase gymnotic oligonucleotide function with time.

Example 4: Cellular Stress Increases the Oligonucleotide Function in the Nucleus To establish if the increased interaction between Ago-2 and YB1 translated to augmented oligonucleotide function, a splice switching oligonucleotide (SSO-654) was delivered by gymnosis to the HeLa-EGFP-654 cell line (29), which was either untreated or previously transfected with a stressor (in this case, a non-targeting siRNA). SSO-654 was designed to induce skipping of an exon which disrupts the eGFP coding sequence expressed in these cells; therefore the potency of this splice switching ON is directly proportional to the signal of the eGFP that is produced (29). The stress induced by the siRNA-transfection resulted in more effective splicing switch activity and higher eGFP expression at three separate SSO-654 concentrations (FIG. 13A, compare SSO-654 0.5 µM, 1 µM and 2 µM in non-transfected HeLa-654 cells (Mock) and HeLa-654 cells transfected with a non-targeting siRNA (40 nM siCntr) prior to oligonucleotide delivery). The improvement in SSO-654 activity was also observable at an early time point (24 hours) following SSO-654 delivered by gymnosis, and with a lower concentration (10 nM) of the non-targeting transfected siRNA control (FIG. 13B, 10 nM siCntr) or uncomplexed LIPOFECTAMINE® only (FIG. 13B, Lip3K). The enhancement of oligonucleotide function increased with time (FIG. 13B; see Gymnosis 48 hrs).

Figure 14:
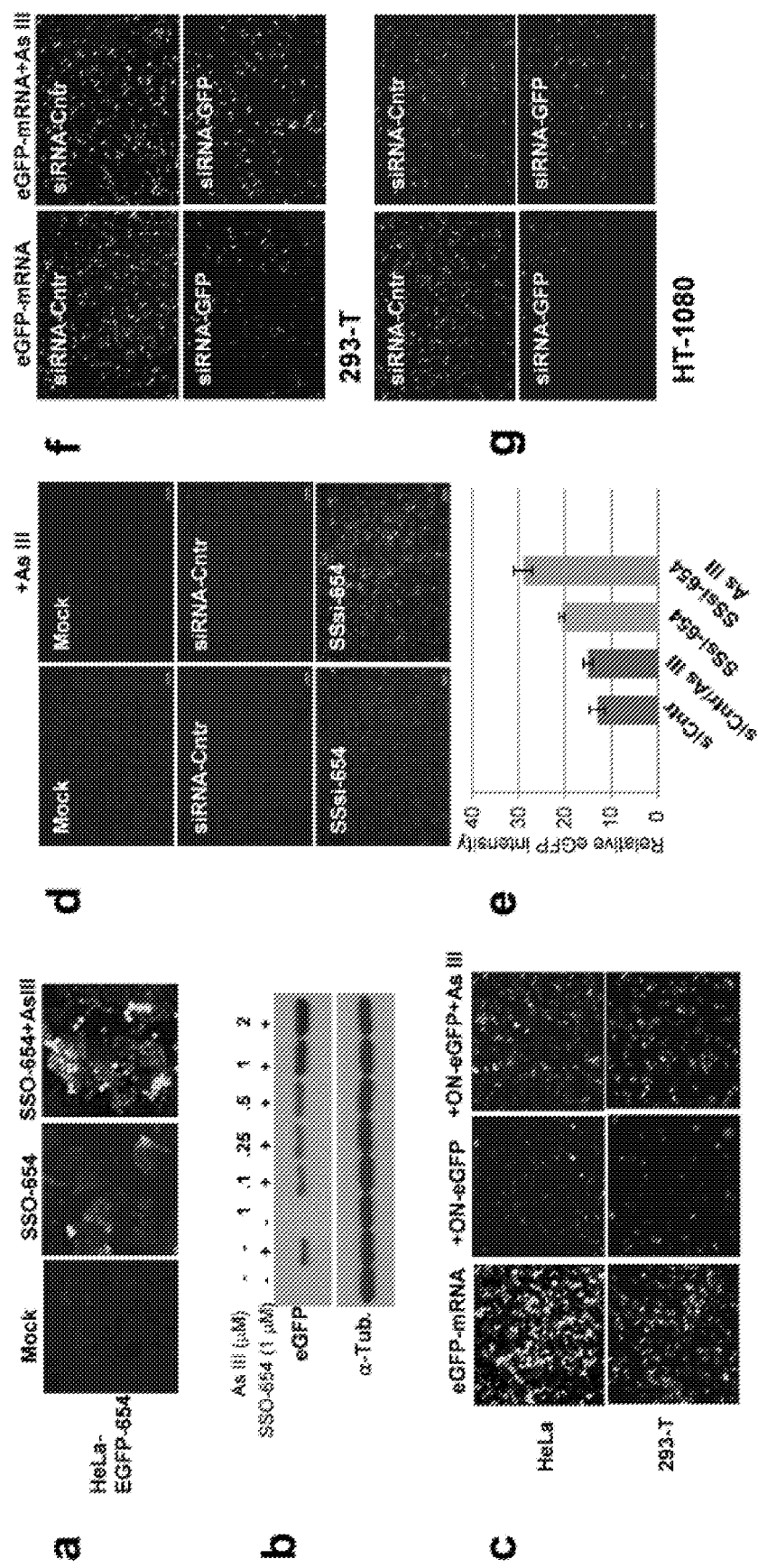
FIGS. 14a-14g show that stress-induced Arsenic III (As III) treatment increases nuclear function and concomitantly decreases the cytoplasmic function of ONs and siRNAs.

The increase in oligonucleotide function could be recapitulated with arsenic trioxide (As III or ATO), a standard cellular stressor. Although As III can cause oxidative damage (30), at the appropriate concentrations it also has therapeutic properties (31). It was found that SSO-654 potency improved, as determined by eGFP production in HeLa-EGFP-654 cells, when low concentrations (0.5-2 µM) of As III were combined with SSO-654 treatment (FIGS. 14A and 14B).

Figure 15A:
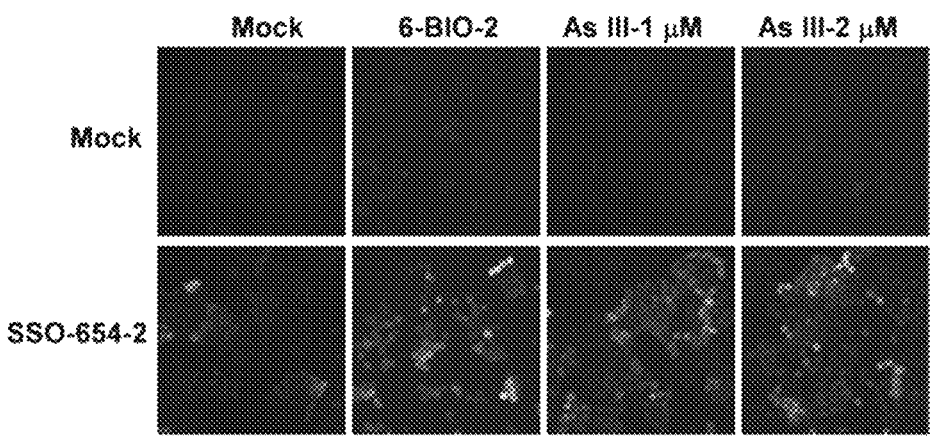
FIGS. 15a-15d show that stressors such as Arsenic trioxide (As III) enhance oligonucleotide activity and that cellular stress increases the activity of SSO-654. HeLa-EGFP-654 cells were treated with 2 uM SSO-654 (SSO-654-2) without (Mock) or with 1 or 2 μM As III prior to fluorescent microscopy. 2 μM 6BIO, which was previously shown to be an enhancer of SSO activity, was used as positive control. The fluorescence detected via microscopy (FIG. 15a) or flow-cytometric analysis (FIG. 15c) shows increased ON function by As III treatment.
Figure 15B:
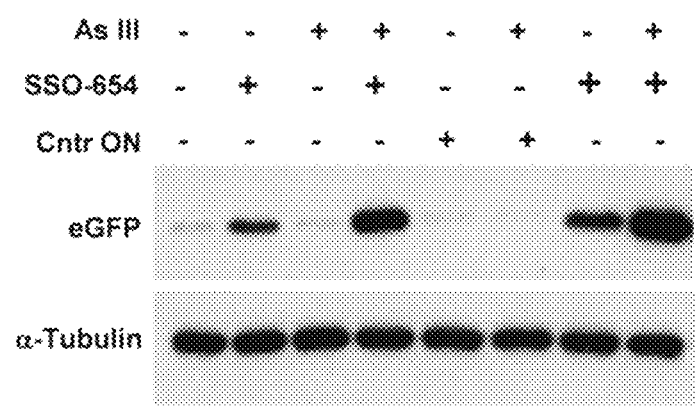
Figure 15C:
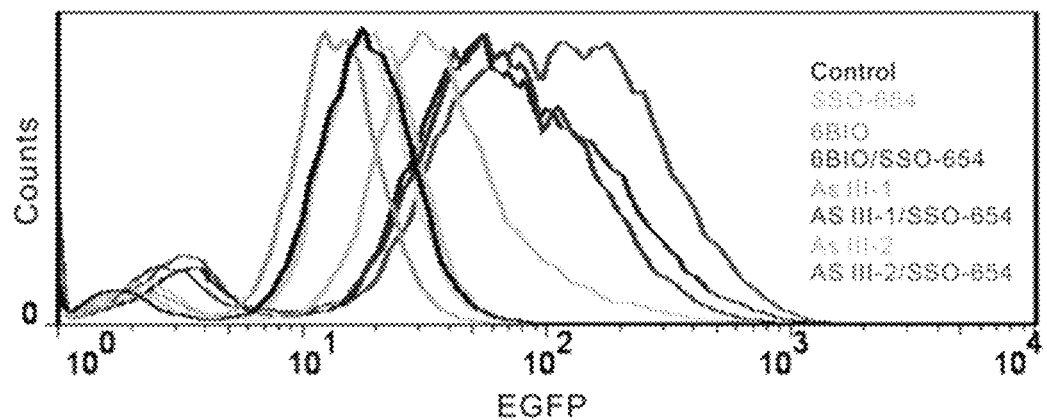
Figure 15D:
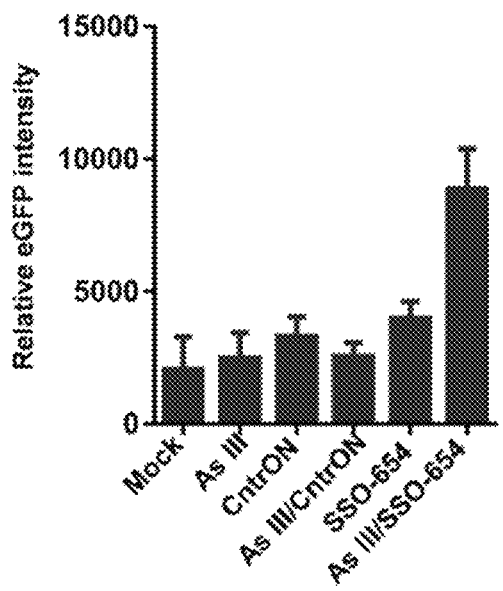

The increased production of eGFP as a function of the As III concentration (1 and 2 µM) was confirmed by flow-cytometry measurements (FIG. 15A). The eGFP protein expression was also quantified by Western analyses at two SSO-654 concentrations (FIG. 15B). Specifically, to test if the effects of transfection on oligonucleotide function could be recapitulated with the use of small molecules and compounds used in the clinic, cells were treated with the SSO-654 and small amounts of 6-BIO or arsenite (As III or ATO), both approved for clinical use. FIG. 15A shows HeLa-EGFP-654 cells that were treated with 2 µM SSO-654 in the absence or presence of 2 µM 6BIO (6BIO-2), 1 µM As III or 2 µM As III for 2 days prior to fluorescent microscopy assays. The analyses show that both compounds are able to increase the oligonucleotide splice switch function (compare cells treated with 6-BIO or As III with Mock control). The fluorescence microscopy results were confirmed with flow-cytometry assays (shown in FIG. 15C). FIG. 15B is a Western Blot analysis of eGFP expression in HeLa-EGFP-654 cells treated with the indicated oligonucleotides and As III for 2 days, and shows greatly increased eGFP protein expression when the oligonucleotide is combined with As III treatment. The eGFP intensity in HeLa-EGFP-654 cells treated with the control oligonucleotide, ASO, or SSO-654, with or without As III treatment was also measured with a microplate reader and its quantification is shown in FIG. 15D.

Figure 16A:
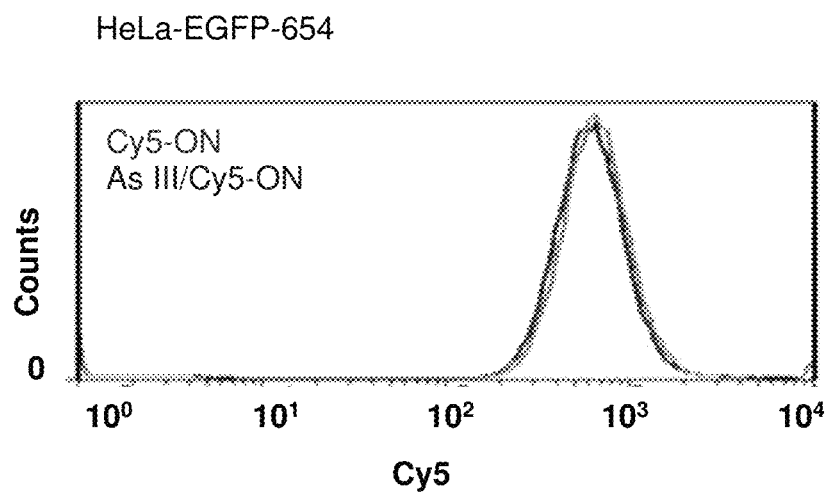
Figure 16B:
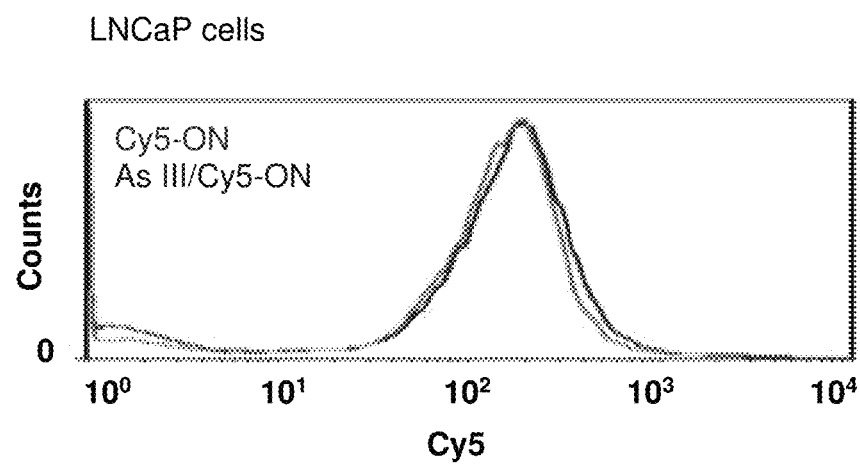
Figure 16D:
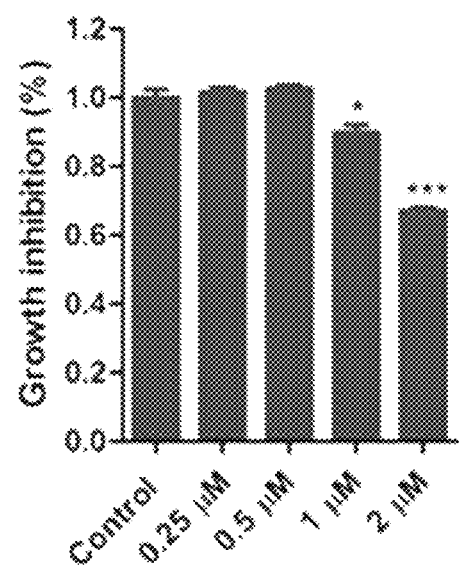

Finally, to exclude the possibility that the enhanced SSO-654 function was due to changes in oligonucleotide uptake or cell viability, the following was evaluated: (1) the efficiency of oligonucleotide delivery by gymnosis in two separate cell lines (HeLa-EGFP-654, FIG. 16A and LNCaP, FIG. 16B) in untreated cells or cells treated with As III (1 µM); and (2) the viability of HeLa-EGFP-654 cells treated with the SSO-654 alone or in combination with As III (FIGS. 16C and 16D). No significant changes in oligonucleotide uptake or cell viability were detected when cells were treated with oligonucleotides in combination with As III (FIGS. 16A-16D).

Figure 17:
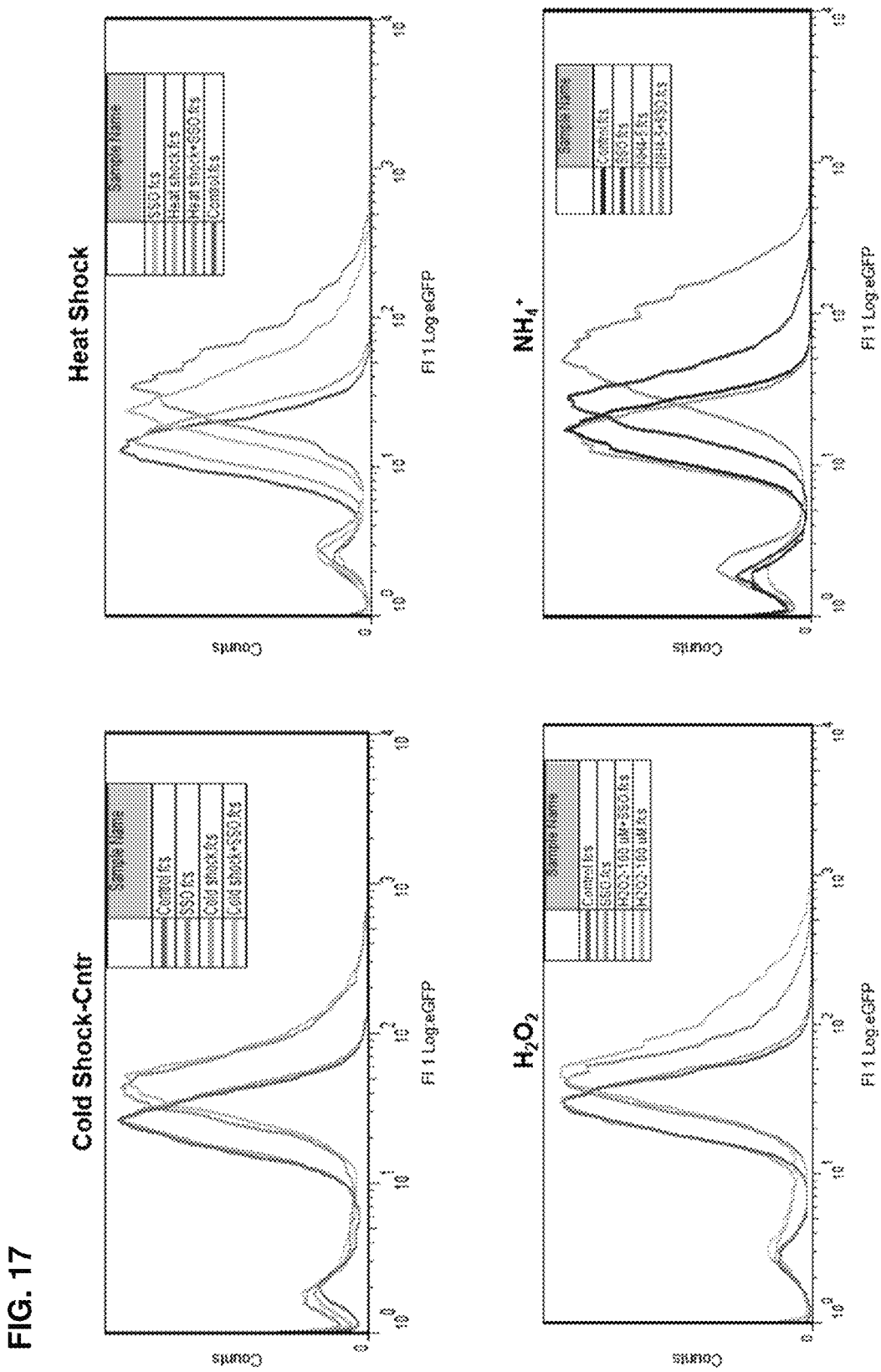
FIG. 17 shows that $H_2O_2$, Heat Shock, and $NH_4^+$ also enhance oligonucleotide activity.
Figure 18:
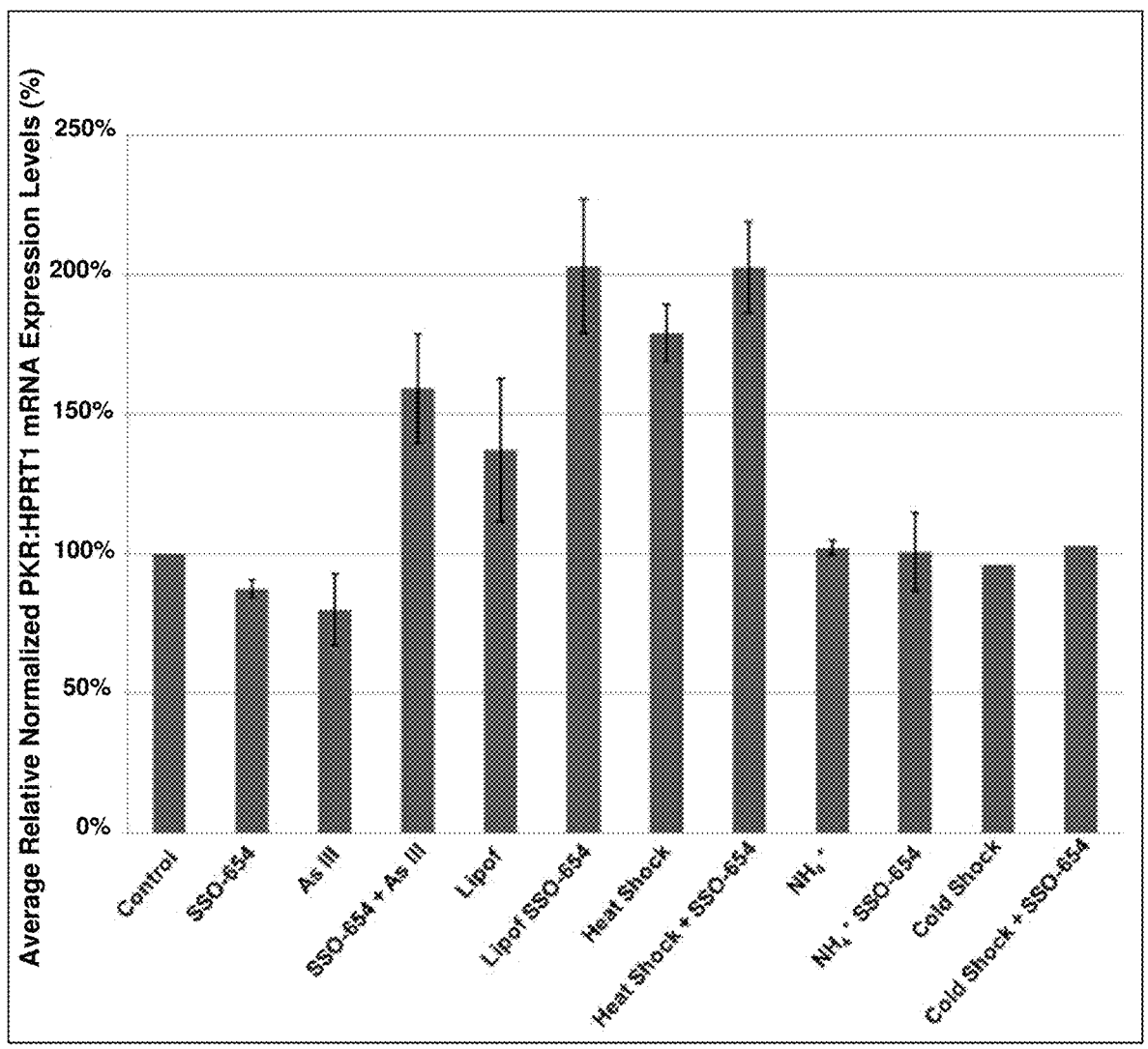
FIG. 18 shows PKR expression levels detected by qRT-PCR in treated HeLa-GFP-654 cells.

These data corroborated that the increased oligonucleotide potency is related to a general cellular stress response. Indeed, additional cell stressors, such as hydrogen peroxide ($H_2O_2$) or heat shock also increased SSO-654 function (FIG. 17), in addition to increasing PKR expression (FIG. 18). Cold shock, which does not significantly trigger cellular stress, was used as a control and did not activate PKR (FIG. 18), nor did it increase SSO-654 potency (FIG. 17). Notably, treatment with ammonium ions ($NH_4$) did not elicit a PKR response (FIG. 18), but still increased the potency of SSO-654 (FIG. 17) and phosphorothioate LNA antisense oligonucleotides.

As shown in FIG. 17, flow-cytometric analysis was used to test if other known cellular stressor such as Heat Shock (HS) and $H_2O_2$ could increase oligo function. Cold Shock does not "stress" the cells and it was used as the control for these experiments. HeLa-EGFP-654 cells were treated with 1 µM SSO in the presence of the indicated conditions for 2 days before subjected to flow cytometric assays. It was found that HS and $H_2O_2$ as well as Ammonium ($NH_4^+$), a proton sponge, were all able to increase oligonucleotide function.

To verify that the various treatments that were used to increase oligo function were working by triggering cellular stress, which in turn resulted in the formation of a nuclear translocating complex, PKR activation was monitored following the treatments. As shown in FIG. 18, real-time PCR analysis demonstrates that PKR is activated when the oligonucleotide is combined with As III, LIPOFECTAMINE® or Heat Shock treatments. The Cold Shock, which is not expected to stress the cells was used as control. NH4+ does increase SSO activity, but it does not seem to activate the stress gene response. Thus, NH4+ is likely working through a different mechanism as described below.

Figure 19A:
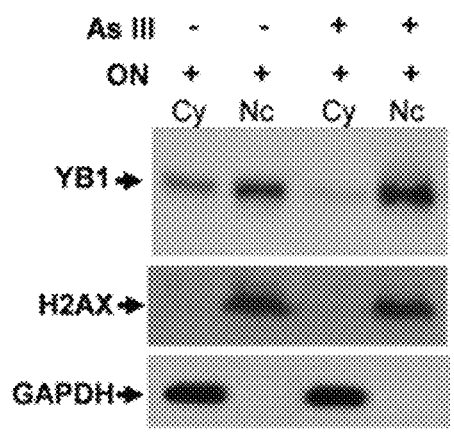
FIGS. 19a-19g show that cellular stress promotes the nuclear translocation of a YB1 complex containing miR-NAs, siRNAs and ONs. Nuclear (Nc) and Cytoplasmic (Cy) fractions of HeLa cells with (+) or without (-) As III and ON treatment, followed by Western analysis (FIG. 19a) and Northern analysis (FIGS. 19b and 19d) for the detection of YB1 (FIG. 19a), ON (FIG. 19b) or miR16 and miR29b (FIG. 19d) demonstrate that YB1, ONs and miRNAs translocated from the cytoplasm to the nucleus after As III treatment. Antibodies specific for H2AX and GAPDH were used to assess the purity of the protein fractions and $\gamma$-$^{32}$P labeled probes base-pairing to the U6 snRNA and tRNA$^{lys}$ were used for the RNA/ON fractions.
Figure 19B:
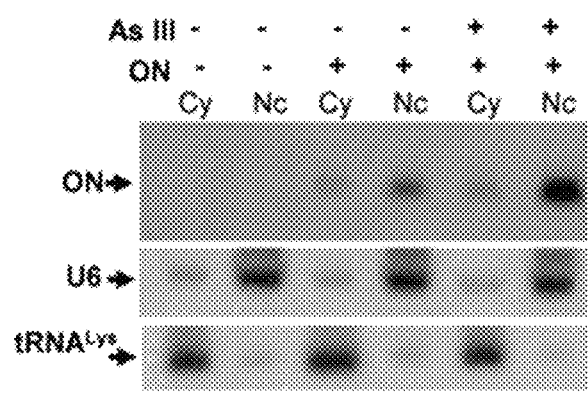

Example 5: Nuclear Translocation of YB1 Coincides with Increased RNAi and Oligonucleotide Potency The increased potency of SSO-654 was a reflection of its increased concentration in the nuclear compartment, and coincided with the nuclear translocation of YB1. Nuclear/cytoplasmic fractionations of the HeLa-654 cells treated with oligonucleotides with or without As III were performed. As III induces accumulation of YB1 in the nucleus (FIG. 19A, compare the YB1 ratio between the cytoplasmic (Cyt) and nuclear (Nc) fractions in cells treated with oligonucleotides but not As III (−) and the same fractions from lysates of As III-treated cells (+)). The nuclear translocation of YB1 after As III treatment corresponds with concomitant accumulation of oligonucleotide in the nucleus (FIG. 19B). Similar results were obtained when using other "stressors" such as LIPOFECTAMINE®. These data is consistent with the immunofluorescence analysis and shows that YB-1 and the oligo are trans locating into the nucleus after As III treatment.

Figure 19C:
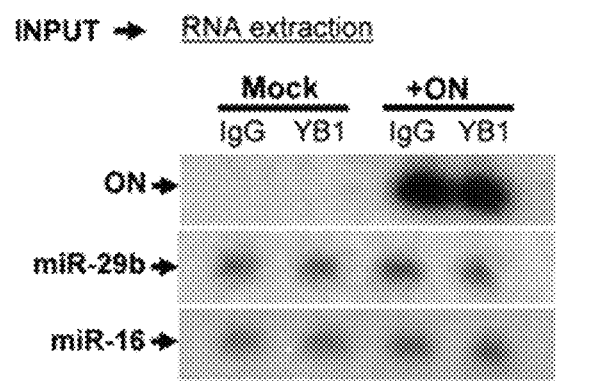
Figure 19C:
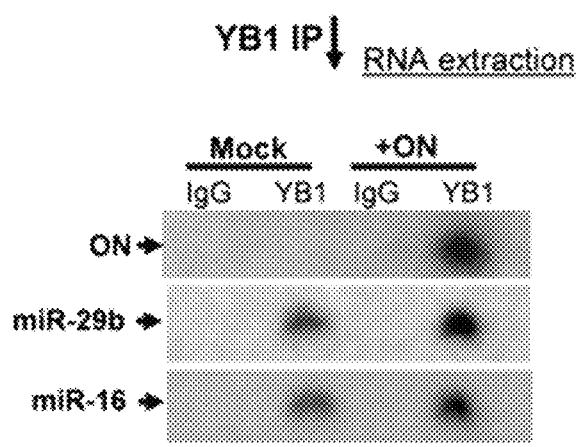

It has been shown that YB1 can bind to and regulate the biogenesis of specific miRNAs (32). As disclosed herein, the interaction of YB1 with Ago-2 increases during cellular stress. It was previously shown that oligonucleotides behave similar to siRNAs, and may hijack endogenous si/miRNA cellular pathways (4). Therefore, whether the nuclear translocation and improvement in function observed using oligonucleotides in stress condition could be recapitulated with si- and miRNAs was investigated. RNA was extracted from the original input lysates (FIG. 19C, top) and the immuno-precipitated samples (FIG. 19C, bottom) and gel analyzed. An immunoprecipitation was performed using anti-YB1 specific antibodies, the nucleic acids were extracted from the lysate precipitates of untreated cells (Mock) or cells treated with 1.5 µM oligonucleotide (+ON), and a gel analysis was performed. An increased association of three separate miRNAs (two, miR-29b and miR-16, are shown. miR-21 followed the same pattern and it is not included in the figure) with the YB1 precipitated complex was observed when cells were previously treated with the oligonucleotide (FIG. 19C, compare miR-29b and miR-16 in the Mock (YB1 lane) vs. in the +ON (YB1 lane)). These results show the presence of microRNAs and oligonucleotide in the YB-1 complex. Moreover, the association of the miRNAs with this complex increase in presence of the oligonucleotide (compare the miR29 or miR16 association with YB-1 immuno-precipitate without or with ASO: bottom right YB-1 and YB-1+ON).

Figure 19D:
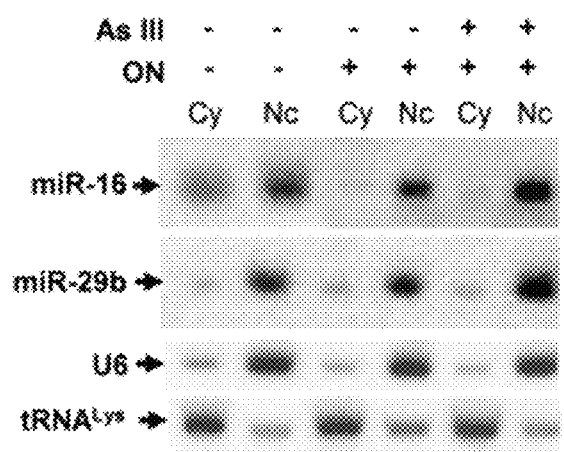

Then nuclear/cytoplasmic fractionations of untreated cells or cells treated with the oligonucleotide, or with a combination of the oligonucleotide and As III were performed. Shuttling of the miRNAs to the nucleus increased proportionally to the extent of the stress signal (FIG. 19D, compare the miRNA ratio of the cytoplasmic (Cyt) and nuclear (Nc) fractions of untreated cells (first 2 lanes) to those of cells treated with the oligonucleotide (lanes 3 and 4) and cells treated with a combination of oligonucleotide and As III (lanes 5 and 6)).

To verify that this nuclear shuttling of miRNAs translated into an increased activity in the nucleus, a splicing switching siRNA (SSsi-654) with the same sequence as SSO-654 was designed. This is a canonical siRNA and thus functions primarily in the cytoplasm; however, splice switching activity in the nucleus was detected (FIG. 19D, first column, compare siRNA-Cntr to SSsi-654 and FIG. 19E). This nuclear function can be increased by As III treatment (FIG. 19D, (+) As III and FIG. 19E), indicating that shuttled mature si/miRNAs are active in the nucleus.

Figure 19E:
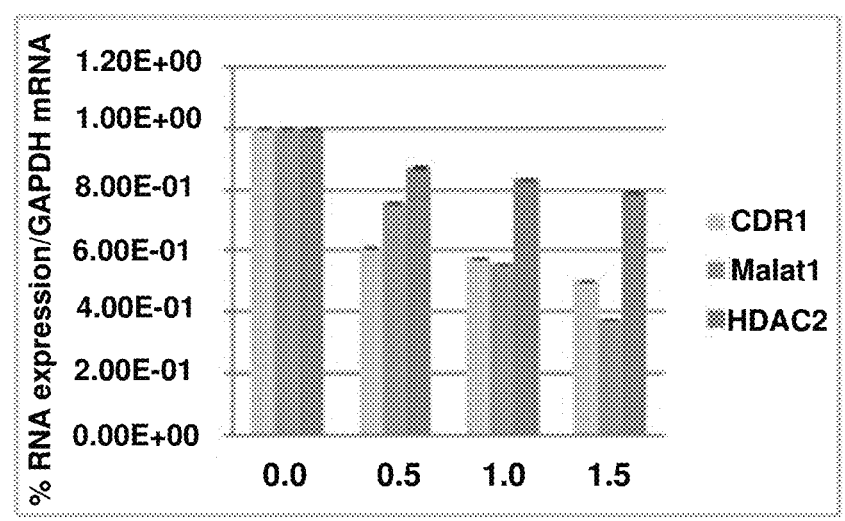
Figure 19F:
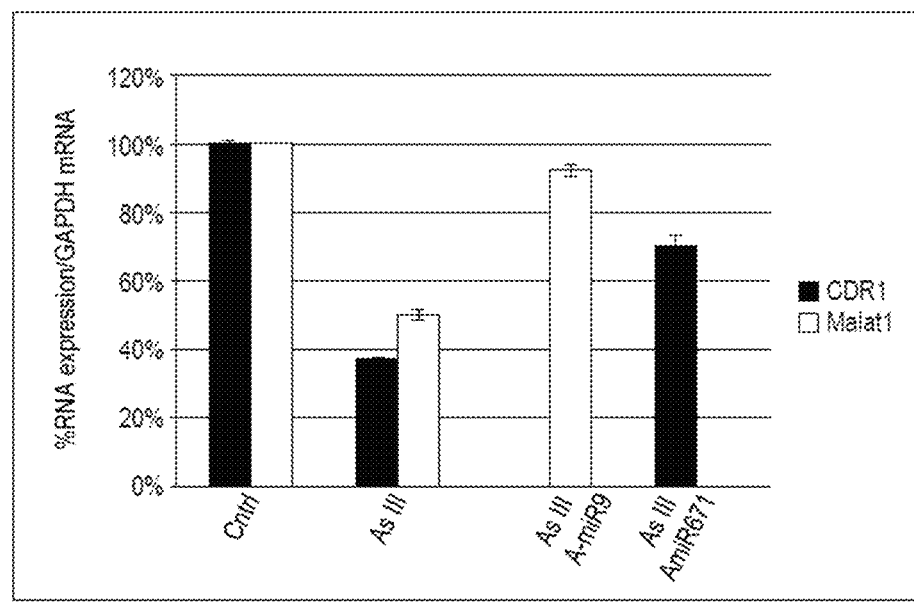
Figure 19G:
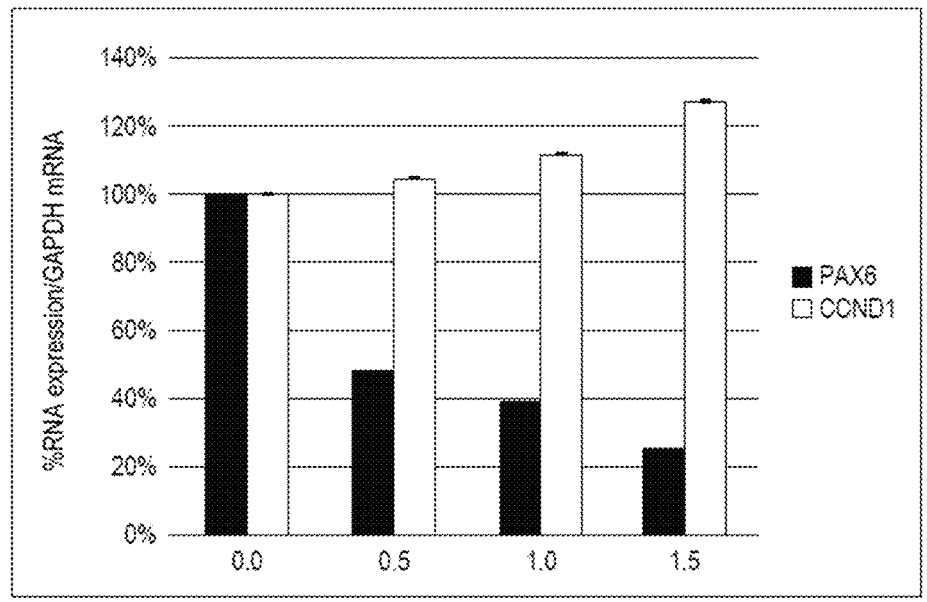

The augmentation of nuclear targeting by the nuclear-translocated siRNAs or oligonucleotides is expected to occur with a concomitant decrease of their cytoplasm is function. Cytoplasmic gene silencing was monitored using a 5' end-capped, 3'-polyadenylated eGFP mRNA (eGFP mRNA) (4). The transfected mRNA is rapidly bound by the ribosome and remains localized in the cytoplasm where it is transcribed to rapidly generate eGFP (4). Low concentrations (10 nM) of an anti-eGFP siRNA (siRNA-GFP) or a non-targeting control (siRNA-Cntr) were delivered to HEK 293-T or HT-1080 cells using LIPOFECTAMINE®3K, which minimizes cellular stress. The next day, cells were re-plated and As III was added to half of the samples. The eGFP mRNA was then delivered to the cells and fluorescence images were acquired shortly thereafter (FIGS. 19F and 19G). Increased siRNA nuclear function (FIGS. 19D and 19E) was accompanied by decreased cytoplasmic function (FIGS. 19F and 19G, compare eGFP silencing in As III-untreated cells (eGFPmRNA, siRNA-Cntr vs. siRNA-GFP, first column) to As III treated-cells, second column).

The same phenomenon could be reproduced when delivering an eGFP-targeted oligonucleotide (ON-eGFP) prior to the eGFP mRNA in HeLa cells (FIG. 14C top row, compare+ ON-eGFP to +ON-eGFP+ As III) and 293-T (FIG. 14C, bottom row) cells. As III causes nuclear translocation of the oligonucleotide thus the eGFP mRNA silencing is reduced (this is the transcribed RNA directly transfected into the cytoplasm). If the oligonucleotide translocates into the nucleus after As III treatment, its cytoplasmic function should be reduced. Therefore, a transcribed capped and polyadenylated eGFP mRNA was transfected, which is confined to the cell cytoplasm, and delivered an antisense eGFP targeting oligo. FIG. 14C shows that the oligonucleotide was able to silence the eGFP mRNA. However, treating the cells with As III resulted in some loss of oligonucleotide function (compare+ON-eGFP to +ON-eGFP+As III).

Finally, to confirm that the increased nuclear function extended to endogenous miRNAs, two separate systems that rely on miR-led target suppression in the nucleus of the CDR-1-AS and the non-coding Malat-1 RNAs were selected. CDR-1-AS (or ciRS-7) is the circular, naturally occurring antisense RNA product of the CDR-1 gene and acts as a sponge of cellular miR-7. This leads to increased expression of the miR-7 targeted transcripts (33-35). CDR-1-AS is, in turn, targeted in the nucleus by miR-671, whose binding supports Ago-2 cleavage and the subsequent destruction of the sponge (33). Reduction of CDR-1-AS results in destabilization of the CDR-1 sense strand, an mRNA localized to the cytoplasm (33). Treating cells with As III could result in increased migration of miR-671 to the nucleus, followed by the targeting of CDR-1-AS and the subsequent reduction of the CDR-1 mRNA. The second system investigated is based on miR-9 regulation of Malat1 gene expression, which has been shown to also occur in the nucleus (36). Similar to the CDR-1 mRNA, the Malat1 RNA could be suppressed by treatment of cells with As III and the resultant shuttling of miR-9 to the nucleus. As shown in FIG. 19E, both CDR-1 and Malat-1 gene expression were silenced as a function of increasing As III concentrations [0.5-1.5 µM], while the expression of HDAC-2 mRNA, which is conventionally targeted by miRNAs in the cytoplasm, did not significantly change.

Figure 20:
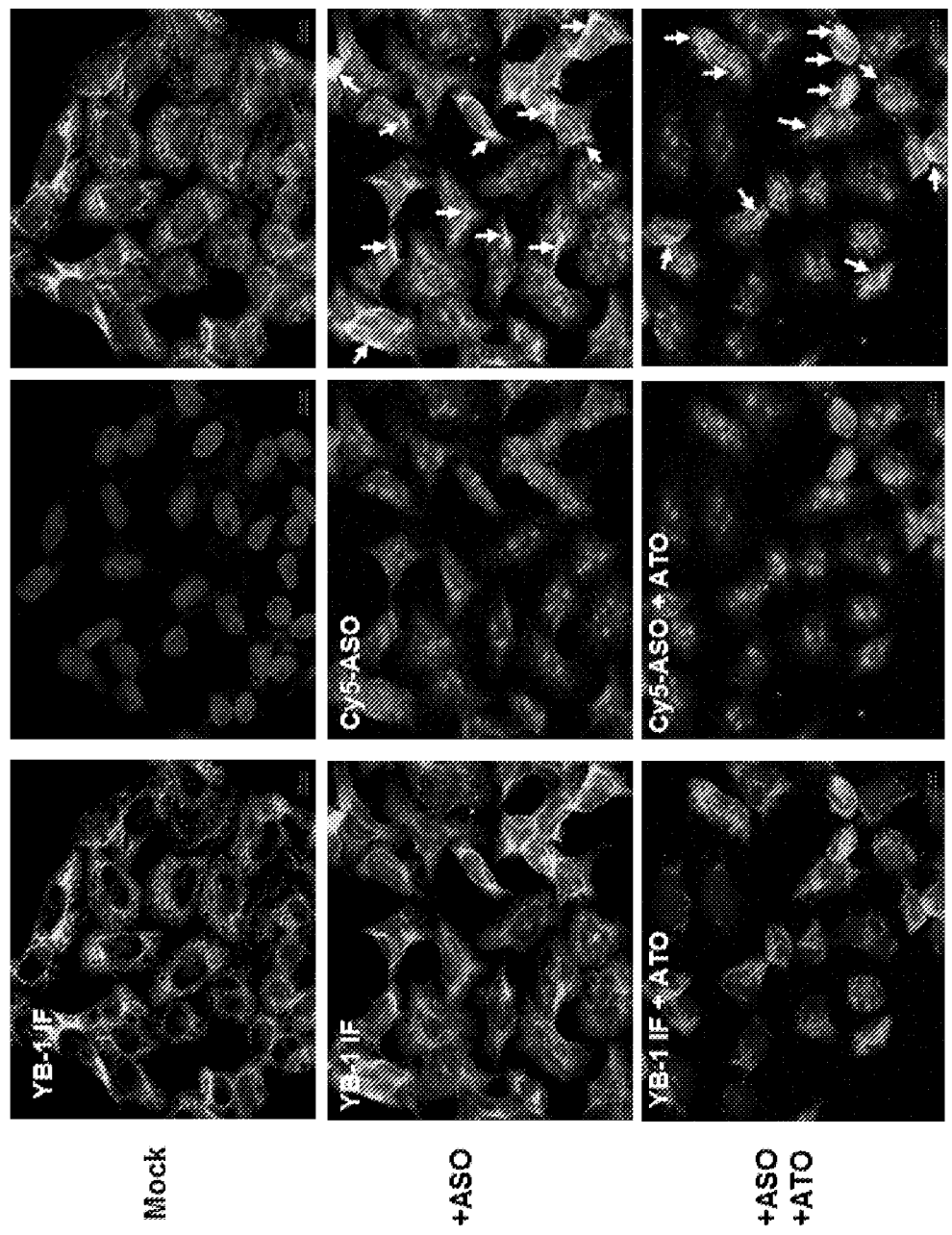
FIG. 20 shows that immuno-fluorescence demonstrates extensive perinuclear and some nuclear localization of the oligonucleotide and YB-1.

Example 6: Oligonucleotides and Ago-2 Co-Localize in Stress Granules (SG) and in the Nucleus FIG. 20 is an immunofluorescent assay of HeLa-EGFP-654 cells treated with Cy5-ASO with or without ATO for 24 hr., and the cellular localization of ASO and YB-1 with and without ATO treatment was detected. In absence of stress the Cy5-oligonucleotide (Cy5-ASO) mostly co-localizes with YBX-1 perinuclearly (FIG. 20, middle row, merged image), after ATO treatment some is visible in the nucleus (FIG. 20, bottom row, merged image). The strength of the signal may not be representative since YB-1 undergoes a proteolitic cleavage prior to its nuclear translocation. The anti-YB-1 ab may not be as effective in recognizing the cleaved protein.

The data support the occurrence of a YB1/Ago-2 interaction that shuttles siRNAs and miRNAs into the nucleus, likely as a mechanism of gene regulation in response to cellular stress. Oligonucleotides delivered by gymnosis hijack this pathway to reach the nucleus. To examine where within the cell the interaction between the oligonucleotides and this endogenous cellular pathway occurs, we delivered 5'-Cy5-oligonucleotides to cells with and without As III treatment, and an immuno-fluorescence assay was performed using anti-Ago-2 specific antibodies (FIG. 21A).

Figure 21:
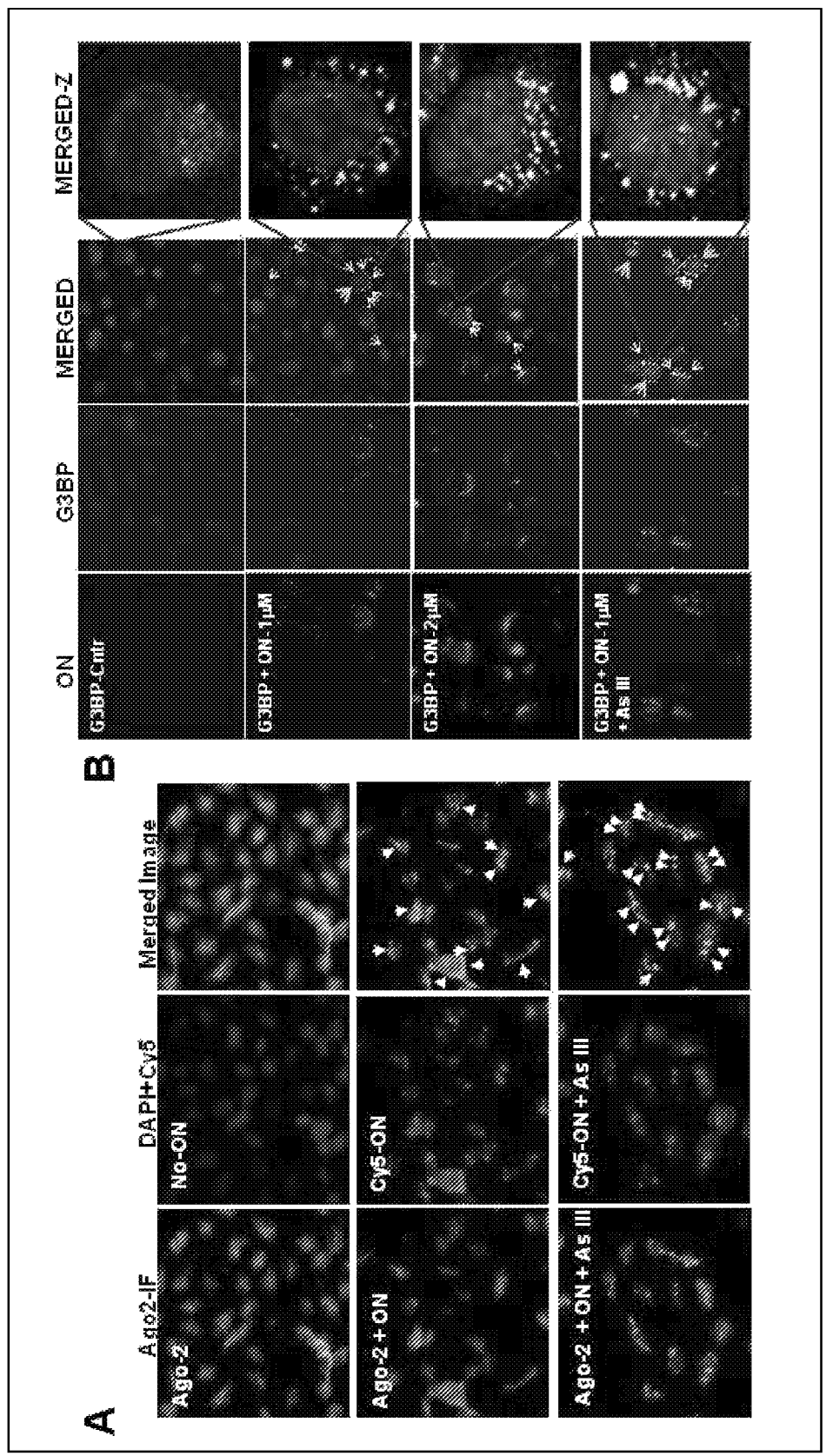
FIGS. 21A and 21B show nuclear localization of the oligonucleotide and Ago-2 following stress. ONs co-localize with Ago-2 in perinuclear stress granules and in the nucleus where they translocate as a result of As III treatment.
Figure 22:
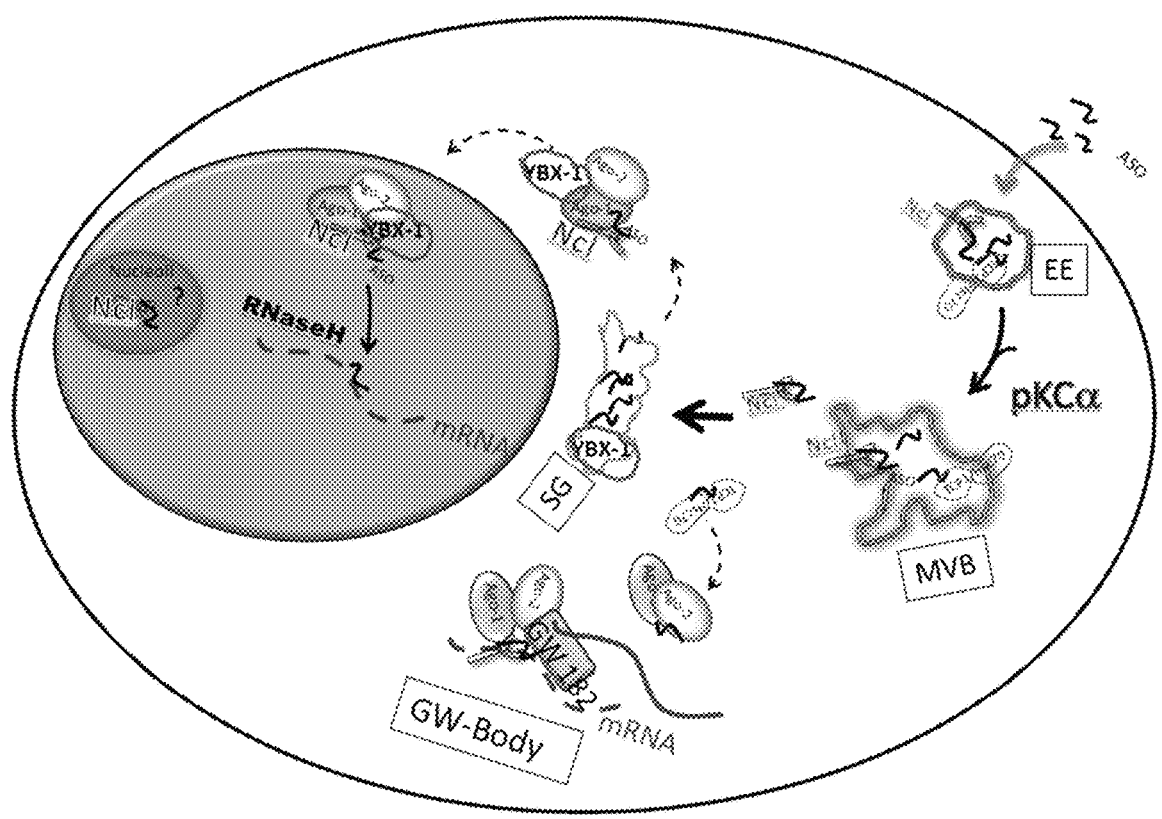
FIG. 22 is a diagram illustrating nuclear shuttling as stress response.

FIG. 21A is an immunofluorescent assay of HeLa-EGFP-654 cells treated with Cy5-oligonucleotide with or without As III (aka ATO) for 24 hr., and the cellular localization of the oligonucleotide and Ago-2 with and without As III treatment was detected. The Cy5-oligonucleotide co-localizes with Ago-2 in the perinuclear region and the nucleus, where nuclear speckles can be seen (FIG. 21A, middle row, merged image, see arrows) and this nuclear co-localization of Ago-2 with the oligonucleotide is significantly increased following As III treatment (FIG. 21A, bottom row, merged image, see arrows). Since this complex responded to cellular stress, it was speculated that the structures observed in the perinuclear region of the cells largely represented SG. YB1 and Ago-2 are known to localize with both p-bodies and SG (25, 37) and these compartments seem to physically interact and share their contents (37, 38). Substantial localization of oligonucleotides in p-bodies and in non-identified cytoplasmic structures was previously demonstrated (4).

The SG in HT1080 cells was visualized using a stress granule marker, fluorescent G3BP protein, and the 5-'Cy5-labeled oligonucleotide was delivered via gymnosis. The co-localization of the 5'-Cy5-oligonucleotide to the SG, and its shuttling to the nucleus, was enhanced by doubling the oligonucleotide concentration (from 1 µM to 2 µM; FIG. 21B, compare second and third rows) and by As III treatment (FIG. 21B, compare second and forth rows).

Example 7: Additional Proteins Bind to YB1/Ago-2 to Generate a Shuttling Stress Induced Response Complex (SIRC)

SISC includes splicing regulators, translation regulators and chromatin remodeling factors such as CTCF, FUS, Smad1 and Smad3, YB-1. These proteins can bind RNA and DNA and have some preferential affinity for specific short nucleotide sequences. These short sequences can be included in the site selection process to increase the targeting of siRNAs-, shRNAs- miRNAs- and oligonucleotides-bound SISC. The technology disclosed herein can be used to affect gene splicing or to target promoter sequences and trigger gene activation or permanent silencing.

The YB1/Ago-2 complex, in addition to nudeolin and Ago-1, can include additional proteins, some of which may be involved in gene regulation as a response to cellular stress. Based on the known interactions of proteins with oligonucleotides and/or YB1 and Ago-2, Ago-1 and Ago-2 immunoprecipitations from the lysates of untreated or oligonucleotide- and As III-treated cells were analyzed for the presence of additional proteins present in the SIRC (FIGS. 23A and 23B).

Cells may respond to stress by modulating gene expression at the transcription and/or splicing steps. The following molecules were analyzed: 1) YB-1, which is known to localize in cytoplasmic nuclear speckles (mostly stress granules) and is involved in transcription, replication and RNA processing. Its patterns of localization resembles siRNAs and oligonucleotides. 2) FUS which binds ssDNA, dsDNA, ssRNA and Sp1. The latter in turn binds to CG promoter sequences. It's involved in pre-mRNA splicing and export. It may also be implicated in mRNA/MiRNA processing, regulation of gene expression and genome integrity. 3) SMAD1, which is a very important factor for the regulation of transcription activation and repression. SMAD also interacts with CRM-1 which in turn interacts with siRNA. We have previously shown that CRM-1 shuttles the siRNAs between the nucleus and the cytoplasm. 4) CTCF, an important transcriptional repressor, which plays an important role in the epigenetic regulation.

The interaction of Ago-2 with the Smad complex was confirmed by immuno-blotting the immunoprecipitations with antibodies specific for Smad-1, 3 and 4. The binding of Smad1 and Smad 4 to Ago-2 significantly increased upon stress (FIG. 23, compare A to B (SIRC)). The nuclear protein FUS, quickly associates with cytoplasmic SG during cellular stress (39) and affects miRNA biogenesis (40). Furthermore, FUS binds to RNA and single and double stranded DNA.

Figure 24:
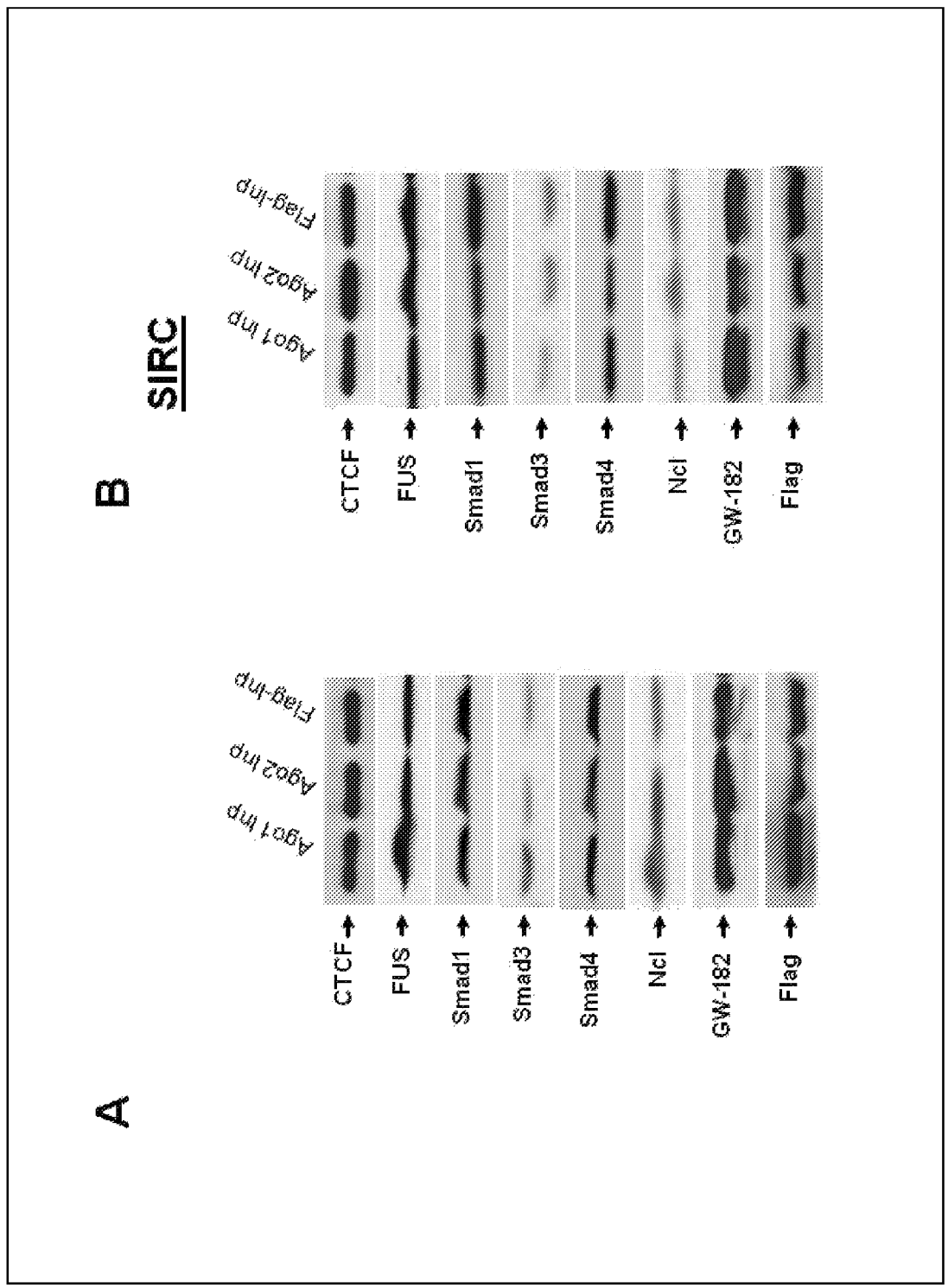
FIGS. 24A and 24B show the input controls for the experiment of FIGS. 23A-23B.

Under normal growth conditions, there is only a minimal association of FUS with the Argonaute complex (FIG. 23A). Its association with Ago-2 increases upon the induction of stress (FIG. 23, compare FUS, Ago-2 IP in A, to FUS, Ago-2 IP in B). This same shift in Ago-2 association could also be seen for (1) CTCF, a master regulator of transcription that has been shown to interact with YB1 (41) and the Smad proteins (42); (2) Ago-1; and (3) TNRC6A, a GW182 protein that localizes to p-bodies and is capable of shuttling active RNAi factors and miRNAs into the nucleus (2, 43). The association of Ago-2 with Smad-3 and nucleolin was not affected by stress (FIGS. 23A and 23B). The input controls for these experiments are shown in FIGS. 24A and 24B.

Example 8: Ammonium Ion Enhances Therapeutic SSO Function in Cells

Figure 26A:
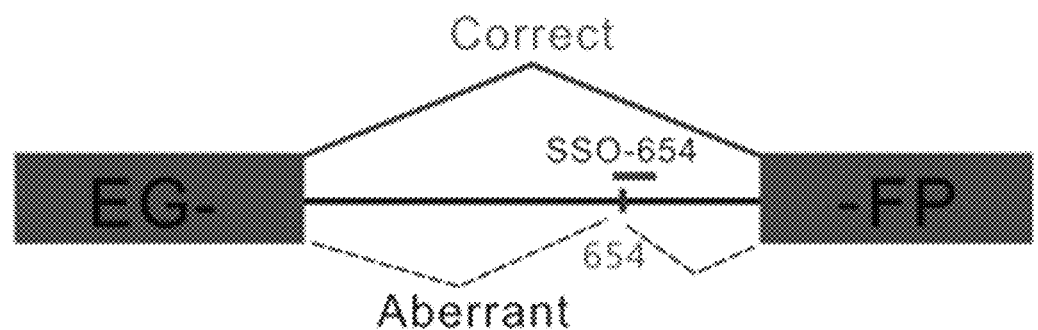
FIGS. 26a-26f demonstrate that $NH_4^+$ enhances SSO activity.

The HeLa EGFP-654 cell line (61,62), stably expresses an EGFP pre-mRNA whose coding sequence is interrupted by the insertion of an additional exon. The binding of SSO-654 to the first 3' splice site causes the skipping of this internal exon and restores the correct EGFP reading frame and EGFP protein expression (FIG. 26a). This cell model was used to see oligonucleotide efficacy could be improved. As shown in FIGS. 26b-26f, ammonium chloride ($NH_4$) significantly enhanced the function of an oligonucleotide, SSO-654.

Figure 26B:
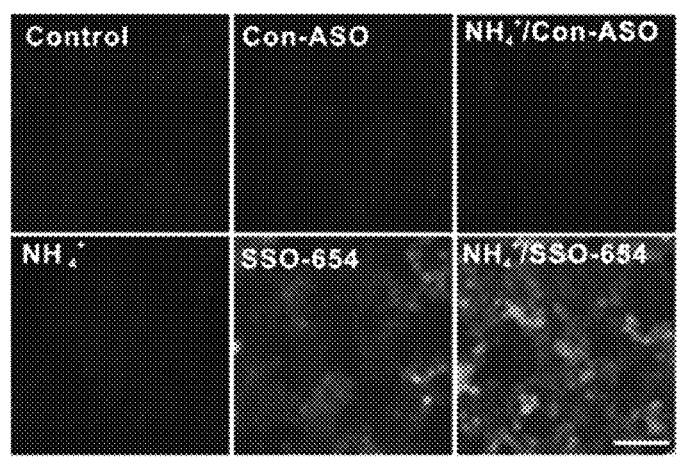
Figure 26C:
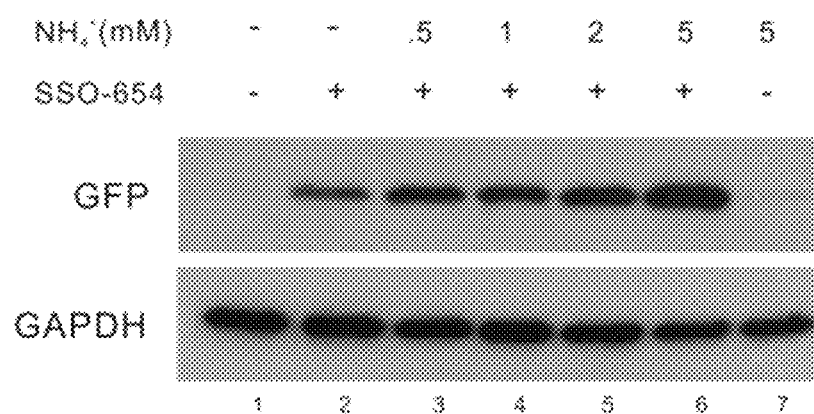
Figure 26D:
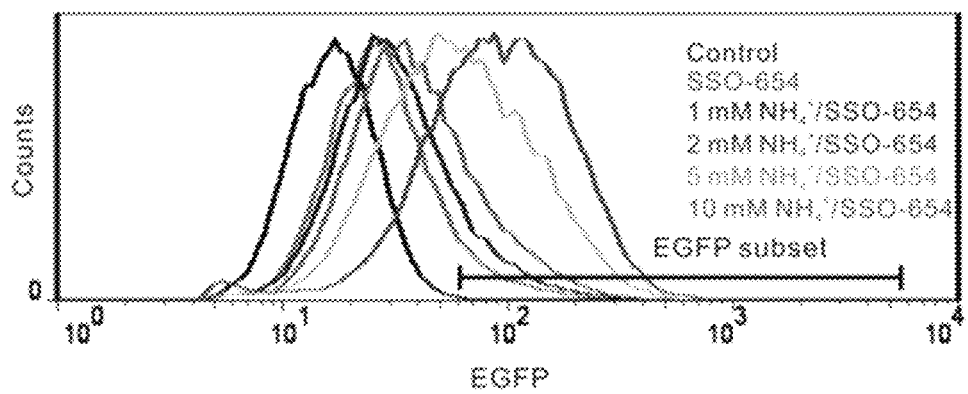

HeLa EGFP-654 cells stably express an EGFP construct whose coding sequence has been interrupted by the insertion of an aberrant intron from the human β-globin gene. A mutation at position 654 in this intron creates aberrant splice sites, preventing EGFP expression. Binding of SSO-654 to the aberrant splice site restores correct splicing and EGFP expression. In FIG. 26b the HeLa EGPF-654 cells were treated for two days with 1 µM non-targeting control oligonucleotide (Con-ASO), 1 µM SSO-654 (SSO-654), 5 mM $NH_4^+$, a combination of Con-ASO/$NH_4^+$ or SSO-654/$NH_4$. In FIG. 26c Western blot assays of SSO-654-mediated GFP protein expression were performed in HeLa EGFP-654 cells treated with 1 µM SSO-654 in the presence of $NH_4^+$ at the indicated concentrations for two days. Flow cytometry assays of SSO-654-mediated EGFP expression in HeLa EGFP-654 cells. HeLa EGFP-654 cells were treated for two days with 1 µM SSO-654 in combination with increased concentrations of $NH_4$. The flow cytometric data were analyzed using the FlowJo program (Tree Star, Inc., Ashland, Oreg.). The profiles shown in FIG. 26d are typical of three independent experiments. The non-treated HeLa EGFP-654 cells were considered EGFP-negative. The percentage of EGFP-positive HeLa EGFP-654 cells was determined by defining the non-treated control cells as EGFP-negative.

Figure 26E:
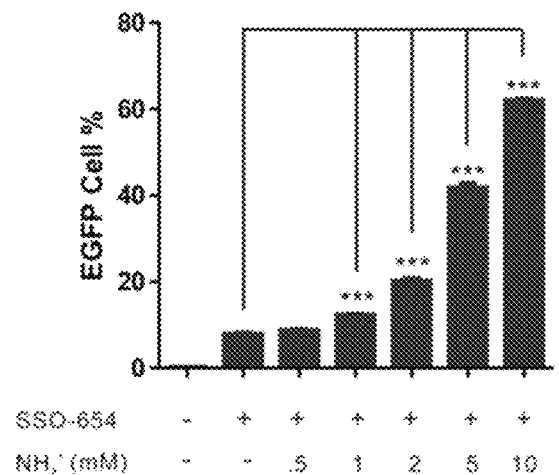
Figure 26F:
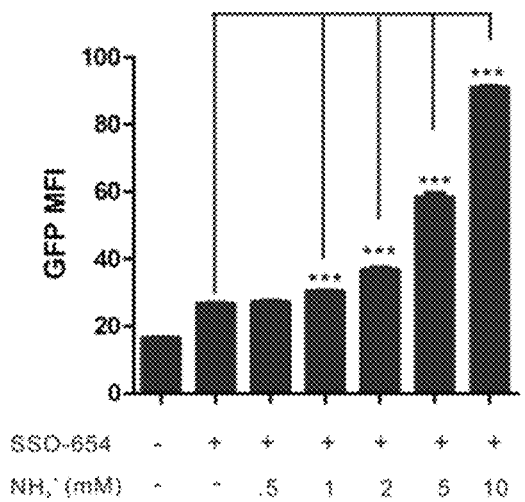

Exposure to 5 mM $NH_4^+$ for 2 days increased SSO-654 function and EGFP expression in HeLa EGFP-654 cells (FIGS. 26b-26f) a minimum of five fold compared to SSO-654 alone as demonstrated by Western analysis (FIG. 26c) and flow cytometric analysis (FIGS. 26d-26f). EGFP expression did not increase after treating the cells with a combination of $NH_4^+$ and a non-targeting control oligonucleotide (FIG. 26b, compare Con-ASO vs. $NH_4^+$ Con-ASO). At lower $NH_4^+$ concentrations such as from 0.5 mM to 2 mM, SSO-654-induced EGFP protein expression increased more than two-fold (FIG. 26c, compare lane 2 to lanes 3-5 and FIGS. 26e and 26f), while treatment with 10 mM $NH_4^+$ increased the percentage of EGFP positive cells and EGFP protein expression nearly seven-fold compared to cells treated with the SSO-654 alone (FIGS. 26d-26f).

Figure 27:
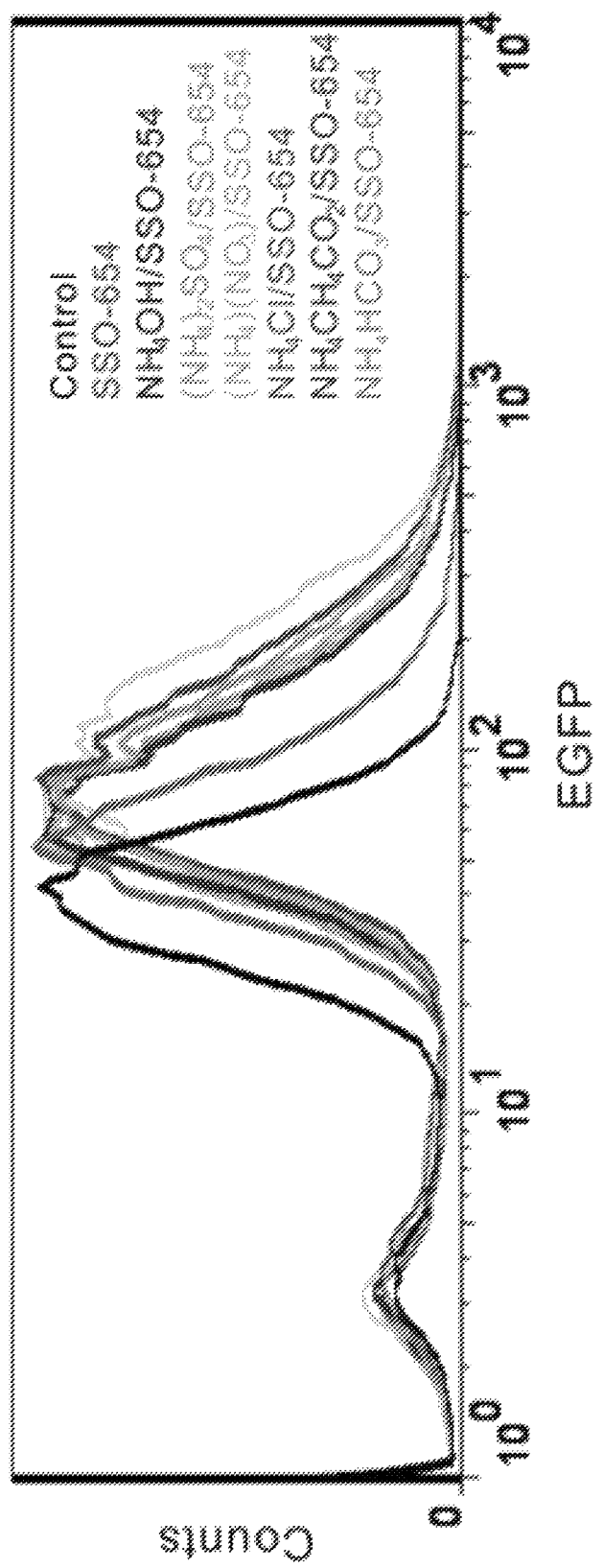
FIG. 27 shows that other ammonium compounds such as ammonium hydroxide ($NH_4OH$), ammonium sulfate ($NH_4SO_4$), ammonium nitrate ($NH_4NO_3$), ammonium acetate ($NH_4CH_4CO_2$), and ammonium bicarbonate ($NH_4HCO_3$) induce similar effects on the SSO-654-mediate EGFP expression in HeLa EGFP-654 cells. The profiles shown are typical of two independent experiments.

Consistent with these results, other ammonium-containing compounds such as ammonium acetate and ammonium bicarbonate produced comparable effects on SSO-654-mediated EGFP expression (FIG. 27). Compounds include ammonium hydroxide ($NH_4OH$), ammonium sulfate ($NH_4SO_4$), ammonium nitrate ($NH_4NO_3$), ammonium acetate ($NH_4CH_4CO_2$), and ammonium bicarbonate ($NH_4HCO_3$). HeLa EGFP-654 cells were treated with 5 mM of each indicated compound in the presence of 1 µM SSO-654 for 2 days prior to flow cytometric analysis.

Taken together, these data demonstrate that $NH_4^+$, at a range of clinically relevant concentrations, significantly up-regulated SSO-654 activity in a dose-dependent manner in HeLa EGFP-654 cells.

Figure 28:
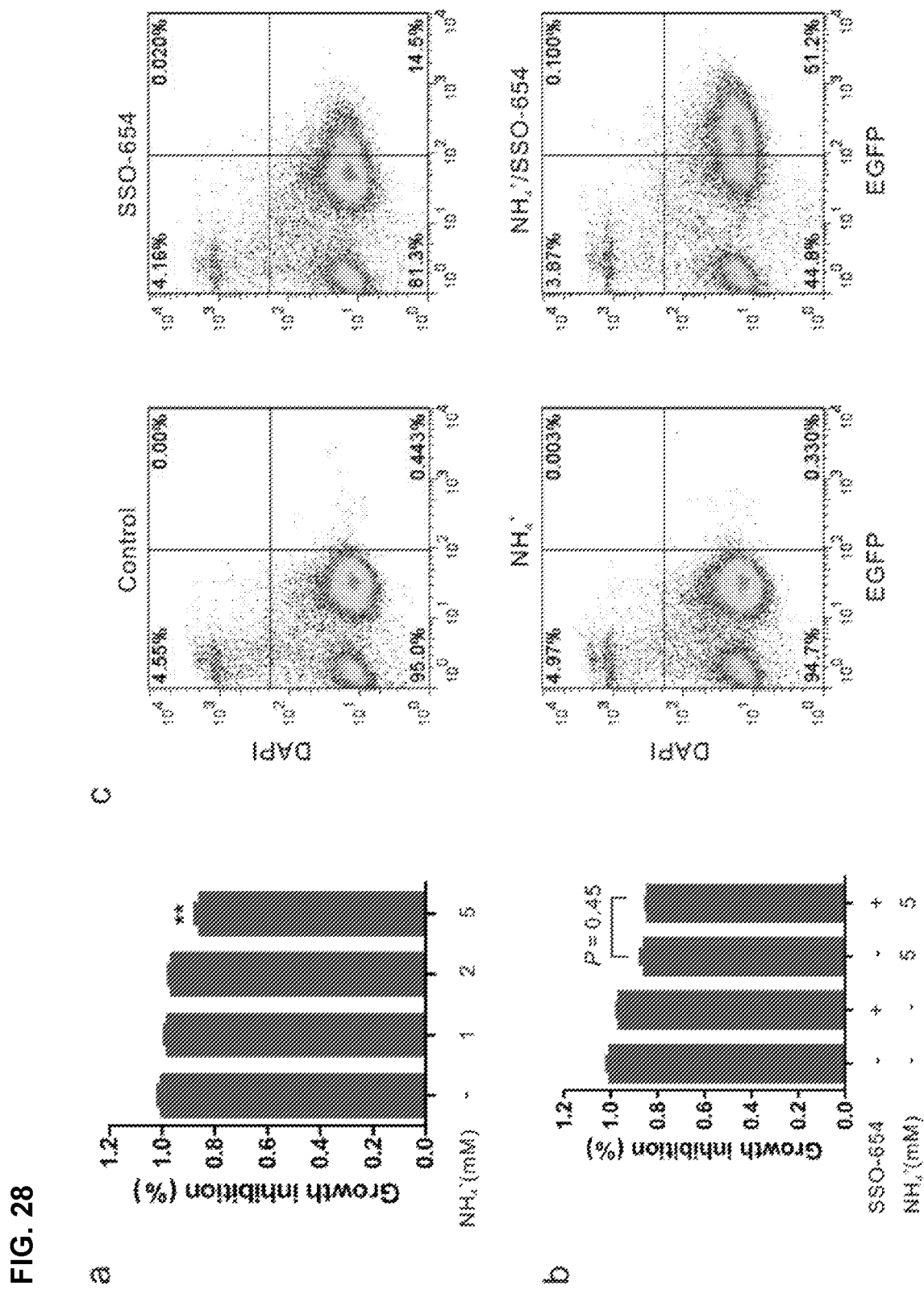
FIGS. 28a-28c show that $NH_4^+$ does not affect cell viability.

Example 9: Ammonium Ion Exposure does not Affect HeLa EGFP-654 Cell Viability $NH_4^+$ can be inhibitory to the growth of and toxic for mammalian cell cultures (71,72). Therefore, whether the exposure of $NH_4^+$ combined with an SSO oligonucleotide could affect the growth, proliferation, and viability of HeLa EGFP-654 cells was examined. In FIGS. 28a and 28b, HeLa EGFP-654 cells were treated with the indicated concentrations of $NH_4^+$, or with 1 µM SSO-654 in the presence or absence of 5 mM $NH_4^+$ for two days. Cell growth and proliferation were assayed by SRB staining. The growth and proliferation of treated cells were normalized to non-treated controls as 100%. In FIG. 28c, the viability of HeLa EGFP-654 cells treated with 1 µM SSO-654 with or without 5 mM $NH_4^+$ for 2 days. Cells were enzymatically harvested and stained with DAPI prior to flow cytometric assay. The flow cytometric data were analyzed using the FlowJo program (Tree Star, Inc., Ashland, Oreg.).

As shown in FIGS. 28a and 28b, $NH_4^+$ at the lower concentrations of 1 mM-2 mM did not affect the growth of these cells; $NH_4^+$ at 5 mM inhibited cell growth by about 15%, consistent with a previously study (71). However, the combination of oligonucleotide SSO-654 and $NH_4^+$ did not increase $NH_4^+$-mediated growth inhibition (p=0.45, FIG. 28b). In cell viability assays employing flow cytometry (FIG. 28c), treatment with $NH_4^+$ and SSO-654 increased the percentage of EGFP-positive cells by nearly four-fold (FIG. 28c, compare the lower right quadrants of SSO-654 and $NH_4^+$/SSO-654), but did not increase the percentage of dead cells, which were detected by DAPI labeling (upper left quadrants), as compared with the control treatments (FIG. 28c, Control and $NH_4^+$).

Example 10: Ammonium Ion Also Enhances ASO Activity in Cancer Cells

Figure 29:
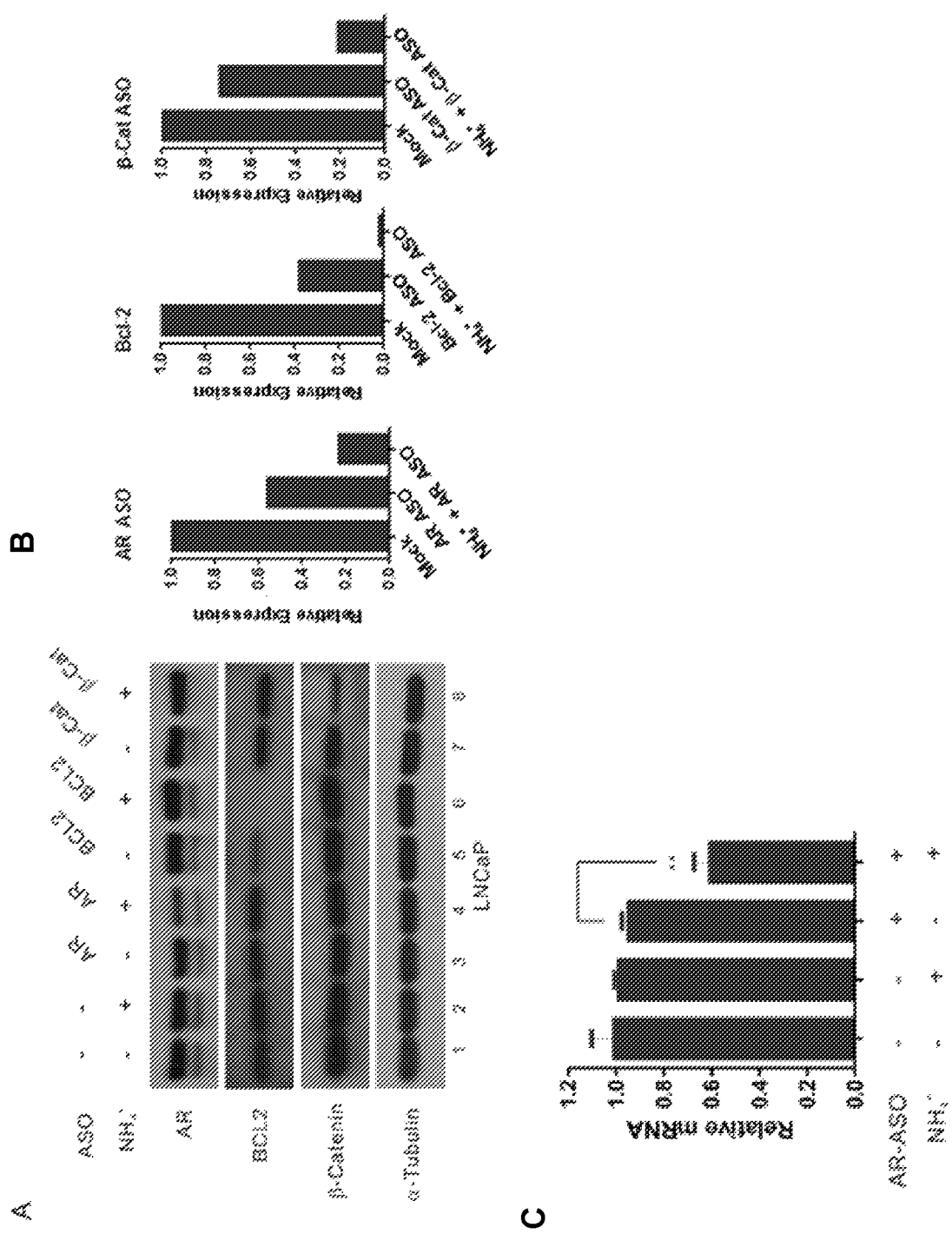
FIGS. 29A-29F show that $NH_4^+$ enhances ASO activity in cancer cells.
Figure 29:
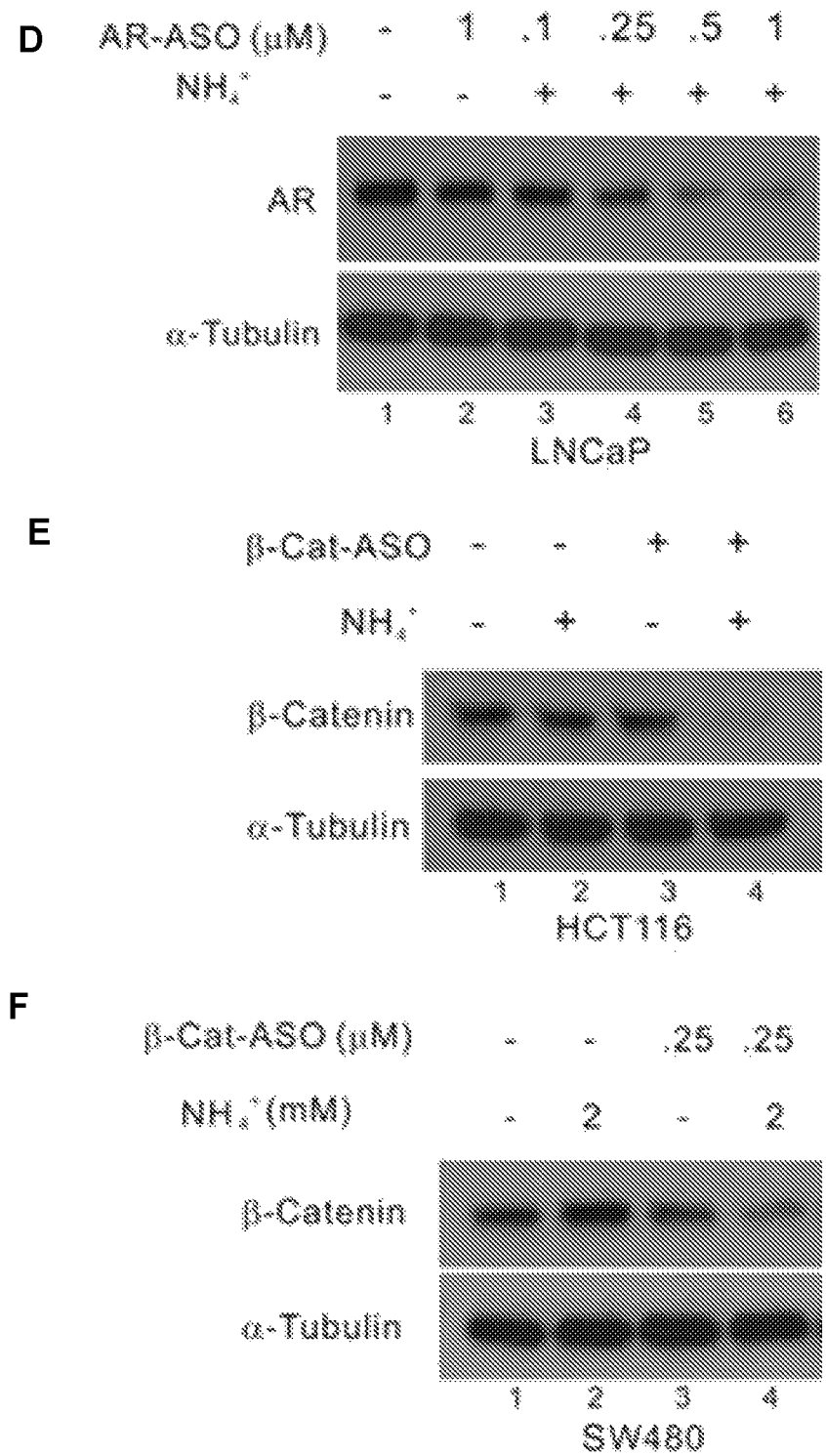

Whether $NH_4^+$ could facilitate the activity of PS LNA gapmer ASOs (ASOs) when delivered to a variety of cells by gymnosis was investigated. LNCaP prostate cancer cells were treated with an ASO targeting either the androgen receptor (AR-ASO), or BCL-2 (BCL2-ASO), or β-catenin (f3-Cat-ASO) mRNAs, with or without added $NH_4^+$. As shown in FIG. 29A, the presence of $NH_4^+$ facilitated ASO-induced gene silencing in a target-specific manner. The combination of treatment with 5 mM $NH_4^+$ and 1 µM AR-ASO for three days led to an 80% reduction in AR protein expression (FIG. 29A, lane 4), whereas treatment with the AR-ASO alone resulted in only a 40% AR reduction (FIG. 29A, lane 3). Furthermore, treatment with 1 µM BCL2-ASO and 5 mM $NH_4^+$ led to a nearly completely depletion of BCL-2 protein expression (98% BCL2-ASO and $NH_4^+$ versus 70% with the BCL2-ASO alone; FIG. 29A, lane 6 versus lane 5). Similarly, treatment with 1 µM β-Cat-ASO and 5 mM $NH_4^+$ led to a decrease of 90% in β-catenin protein expression versus a 30% diminution in cells not treated with $NH_4$ (FIG. 29A, lane 8 versus lane 7).

LNCaP cells (FIGS. 29A and 29B) were treated with indicated ASO and 5 mM $NH_4^+$ for 3 days. Protein expression was quantified with ImageJ. These data illustrate that $NH_4^+$ enhances cytoplasmic function for different targets and cell lines.

A dose response for the AR-ASO in LNCaP cells was obtained and it was demonstrated that 0.25 µM AR-ASO when combined with $NH_4^+$ induced greater AR reduction than 1 µM AR-ASO alone (FIG. 29D, lane 4 versus lane 2). This result was confirmed by qRT-PCR analysis, which demonstrated that the $NH_4$; and AR-ASO combination significantly reduced AR mRNA expression (by about 40%, p<0.01), compared with the AR-ASO alone (FIG. 29C). Furthermore, this outcome could be recapitulated in other cells lines. $NH_4^+$ increased the efficacy of the β-Cat-ASO by approximately two fold in SW480 colon cancer cell lines and nearly eliminated β-catenin gene expression in HCT116 colon cancer cells (FIGS. 29E and 29F, lane 4 versus lane 3). In no case did $NH_4^+$ alone have any effect on gene expression.

Figure 30:
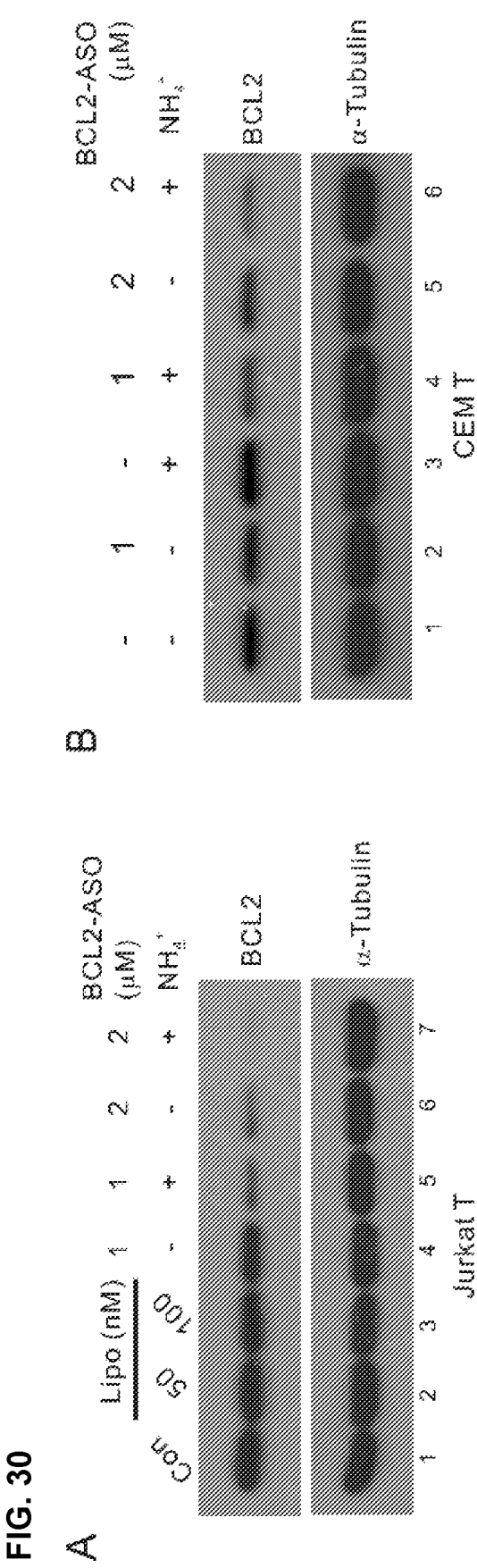
FIGS. 30A and 30B show that NH4+ enhances ASO activity in transfection-resistant T cell lines.

Example 11: Ammonium Ion Enhances ASO Activity in Transfection-Resistant Leukemia Cells Whether $NH_4$+ could promote gymnosis in non-adherent leukemia cells was examined next. These cells are often resistant to liposome-based transfection, a delivery method widely employed for the manipulation of gene expression. The experiment of Jurkat cells, a T lymphocyte cell line, confirmed that these cells were indeed resistant to gene silencing by LIPOFECTAMINE®3000-mediated-transfection of the BCL2-ASO (FIG. 30A). This resistance was found even at high ASO concentrations (50-100 nM; lane 2 and 3 in FIG. 30A). Some silencing of the BCL-2 protein expression was obtained by delivering 1 µM BCL2-ASO via gymnosis (compare lane 4 to lane 1, FIG. 30A). However, when combined with 1 µM BCL2-ASO, the presence of $NH_4+$ facilitated BCL2-ASO-mediated BCL2 silencing by 65% (compare lane 5 to lane 4 and lane 1, FIG. 30A) and nearly completely depleted BCL-2 protein expression when combined with 2 µM BCL2-ASO (compare lane 7, lane 6 and lane 1, FIG. 30A).

The effect of $NH_4^+$ on BCL2-ASO-mediated gene silencing activity in CEM T-lymphoblastoid cells was also confirmed. These cells, like Jurkat T cells, are well-studied and transfection-resistant. Nevertheless, $NH_4^+$ was still capable of augmenting the ASO silencing of BCL-2 gene expression (FIG. 30B). The combination of $NH_4^+$ with 1±M BCL2-ASO resulted in about a 50% reduction of BCL-2 protein expression (FIG. 30B, lane 4), compared with only a 5% reduction obtained using 1 µM BCL2-ASO alone (lane 2). The combination of $NH_4^+$ with 2 µM BCL2 silenced BCL-2 protein expression by roughly 75% (lane 6), versus 2 µM BCL2-ASO alone, which only yielded a 40% decrease (lane 5).

Figure 31A:
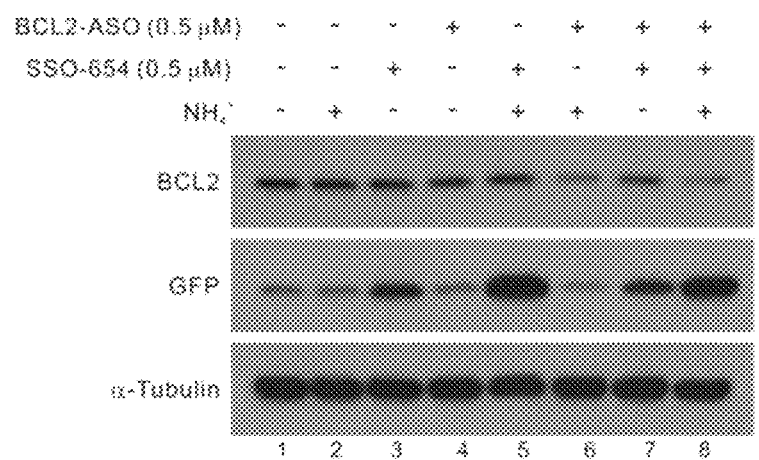
FIGS. 31a-31d show that $NH_4^+$ enhances the activity of two oligonucleotides delivered simultaneously.

Example 12: Ammonium Ion Enhances the Simultaneous Activity of an SSO and an ASO or Two ASOs Targeting Different Genes Whether $NH_4^+$ could simultaneously facilitate the silencing ability of two oligonucleotides in cells in culture was investigated. As shown in FIG. 31a, the combined treatment with $NH_4^+$ and both the SSO-654 and BCL2-ASO increased SSO-654-mediated EGFP expression (GFP, lane 8 versus lane 3), in addition to enhancing BCL2 silencing in HeLa EGFP-654 cells (BCL2, lane 8 versus lane 4). The activity of the SSO-654+BCL2-ASO+$NH_4$a was comparable to that of the SSO-654+$NH_4^+$ or the BCL2-ASO+$NH_4^+$ treatments individually (compare lane 8 to lane 5 or 6 in FIG. 31a). In FIG. 31a, cells were treated with 0.5 µM BCL2-ASO, 0.5 µM SSO-654, or a combination of 0.5 µM of both, in the presence or absence of 5 mM $NH_4^+$ for 2 days, prior to Western blotting. α-Tubulin was used as control.

Figure 31B:
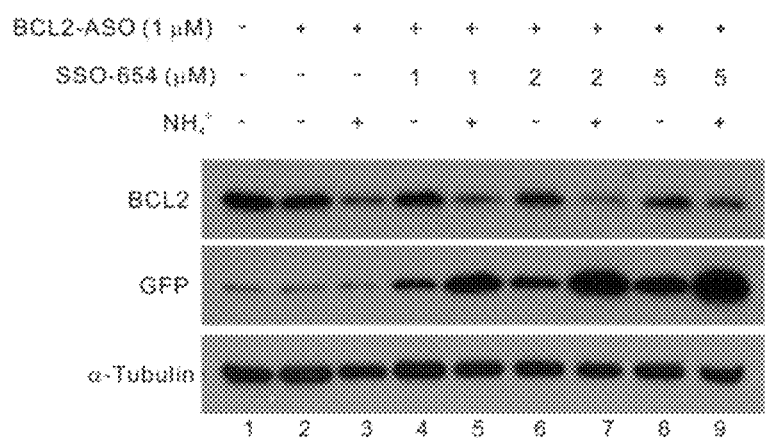
Figure 31C:
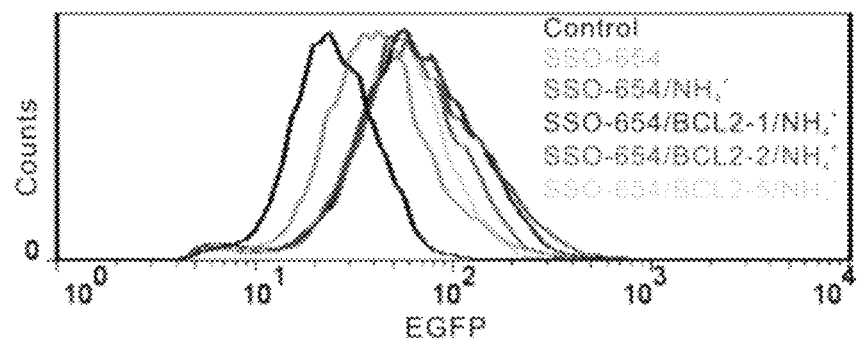
Figure 31C:
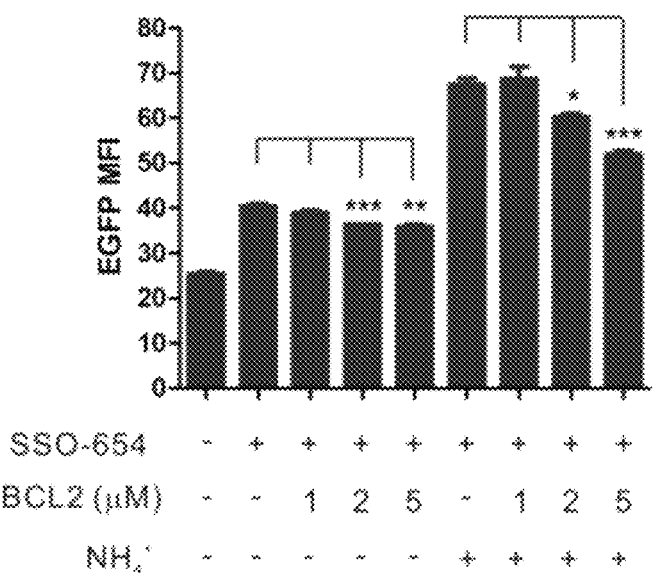
Figure 31D:
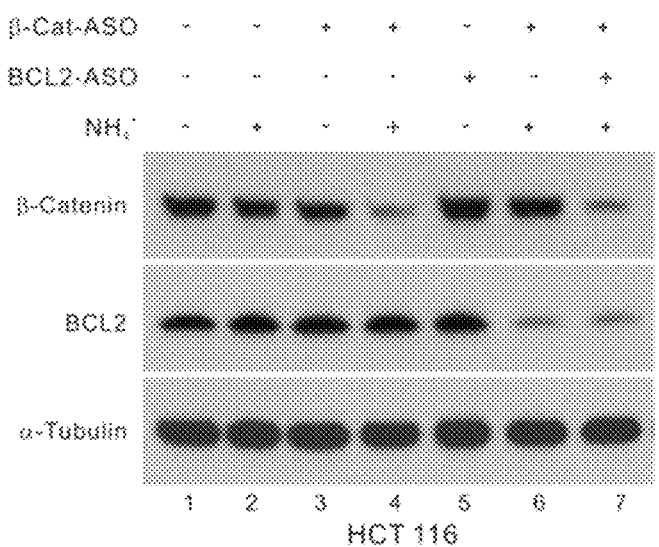
Figure 32:
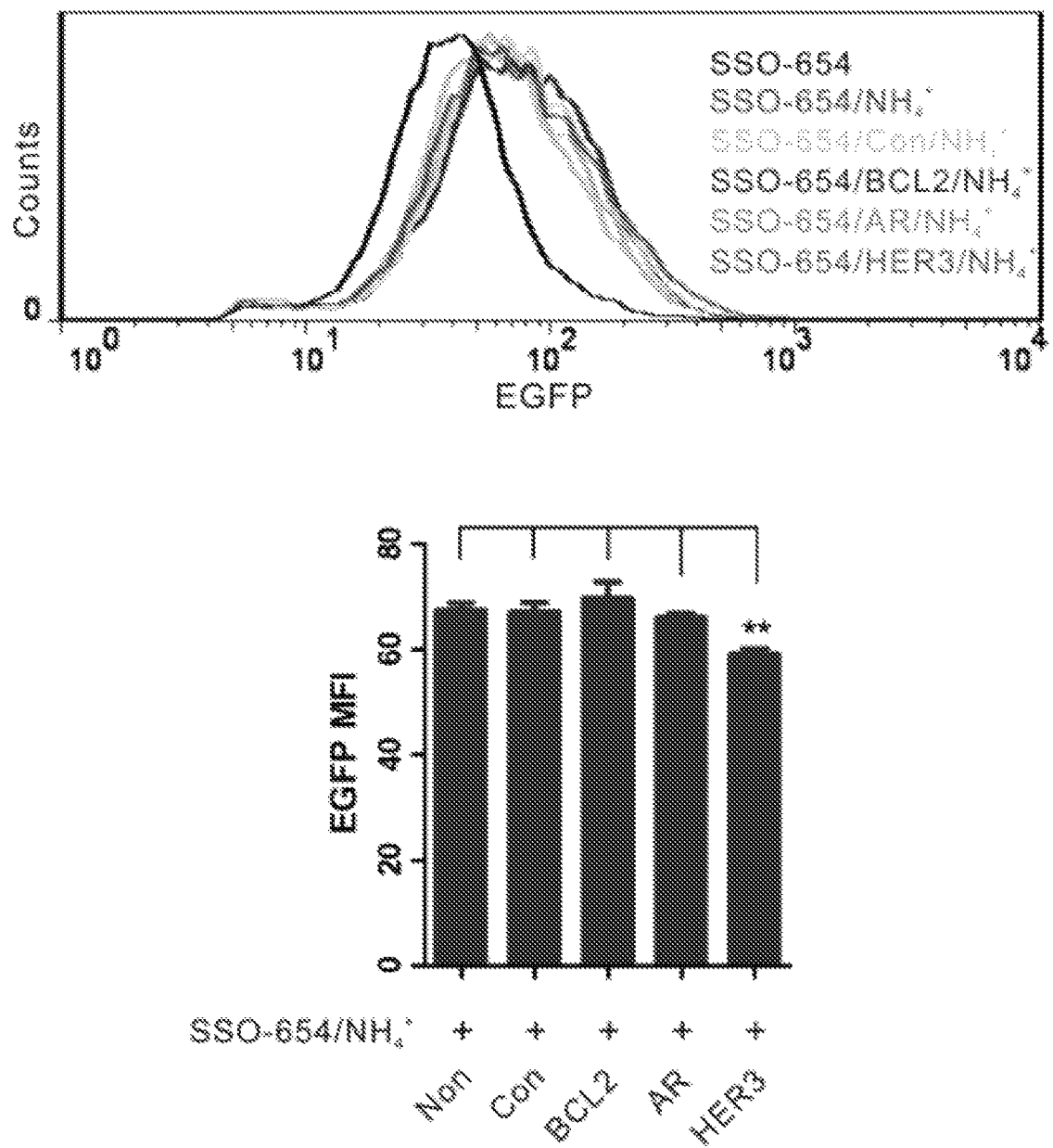
FIG. 32 shows that $NH_4^+$ enhancement on SSO-654 activity is not diminished when additional ASOs are simultaneously delivered to cells. Profiles and graph shown are typical of three independent experiments. Data are expressed as the mean±SD, n=3. **p<0.01, Students t-test.

The concentration of the SSO-654 (evaluated by Western blotting, FIG. 31b) or the BCL2-ASO (evaluated by flow cytometry, FIG. 31c) in the presence or absence of $NH_4^+$ were then titrated. In FIG. 31b, the HeLa EGFP-654 cells were treated with the indicated SSO-654 and BCL2-ASO, with or without 5 mM $NH_4$, for 2 days prior to Western blotting. α-Tubulin was used as control. As shown in FIG. 31b, high concentrations of the SSO-654 (5 µM) could minimally affect the activity of the BCL2-ASO (compare lane 9 with lane 3), while the SSO-654 at lower concentrations 1 µM-2 µM fully maintained the activity of both (compare lane 5 and 7 with lane 3 in FIG. 31b). In contrast, when the concentration of SSO-654 was kept constant at 1 µM while the concentration of the BCL-2 ASO was increased up to 5 µM the activity of the SSO-654 and the resulting increase in expression of EGFP was diminished (compare SSO-654/BCL2-2/$NH_4^+$ and SSO-654/BCL2-5/$NH_4^+$ with SSO-654/$NH_4$, FIG. 31c, top, and bar 8 and 9 with bar 6, FIG. 31c, bottom; n=3; p<0.001). At lower concentrations (up to 1 µM) the BCL2 oligonucleotide did not affect SSO-654 function (compare SSO-654/BCL2 1 µM/$NH_4^+$ with SSO-654/$NH_4^+$, FIG. 31c, top and bar 7 with bar 6, FIG. 31c, bottom). In FIG. 31c, HeLa EGFP-654 cells were treated for 2 days prior to flow cytometry. Consistently, other ASOs, including the AR-ASO, an ASO targeted to HER3 (HER3-ASO), and a non-targeting control oligonucleotide (Con-ASO) all at 1 µM, when combined with 5 mM $NH_4^+$ demonstrated only slight or no inhibition of $NH_4^+$ and SSO-654-mediated EGFP expression in HeLa EGFP-654 cells under the conditions of the experiment (FIG. 32). In FIG. 32, the cells were treated with 1 µM SSO-654/5 mM $NH_4^+$ in the presence of 1 µM non-targeting Con-ASO (Con), BCL2-ASO (BCL2), AR-ASO (AR) or HER3-ASO (HER3) for 2 days, prior to flow cytometric analysis. Finally, $NH_4^+$ also simultaneously enhanced the activity of two gapmer oligonucleotides targeting the BCL-2 or the β-catenin expression delivered to HCT-116 cells (FIG. 31d). In FIG. 31d, HCT116 cells were treated with 1 µM β-Cat-ASO and 1 µM BCL2-ASO, or a combination of both, with or without 5 mM $NH_4^+$ as indicated, for two days.

Figure 34A:
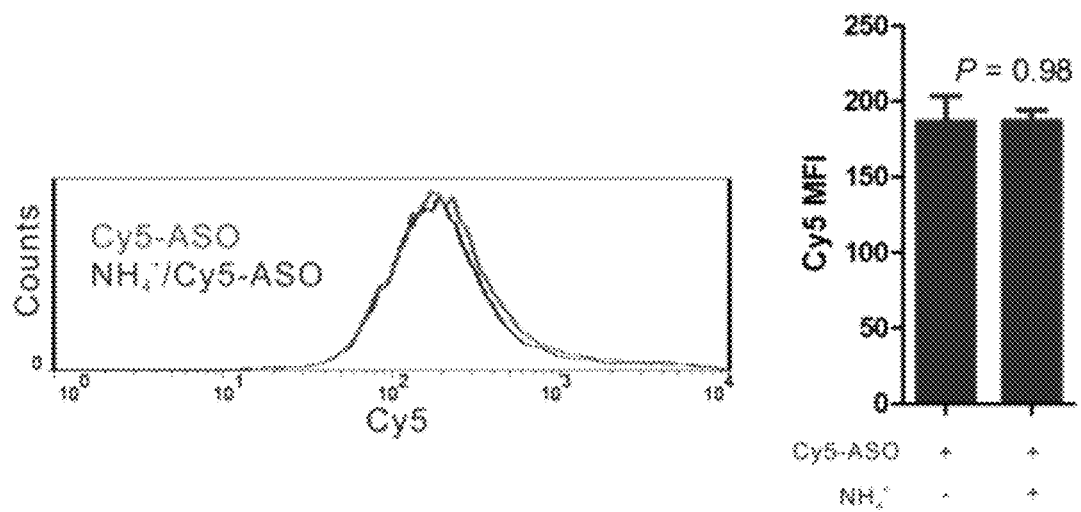
FIGS. 34a-34c show that $NH_4^+$ modules oligonucleotide activity in a similar fashion as other endosome/lysosome inhibitors.
Figure 34B:
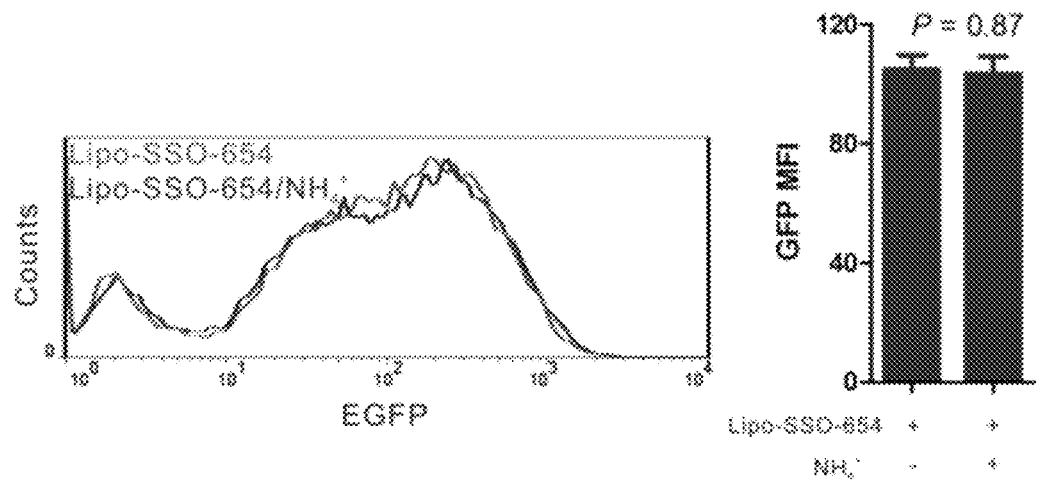
Figure 34C:
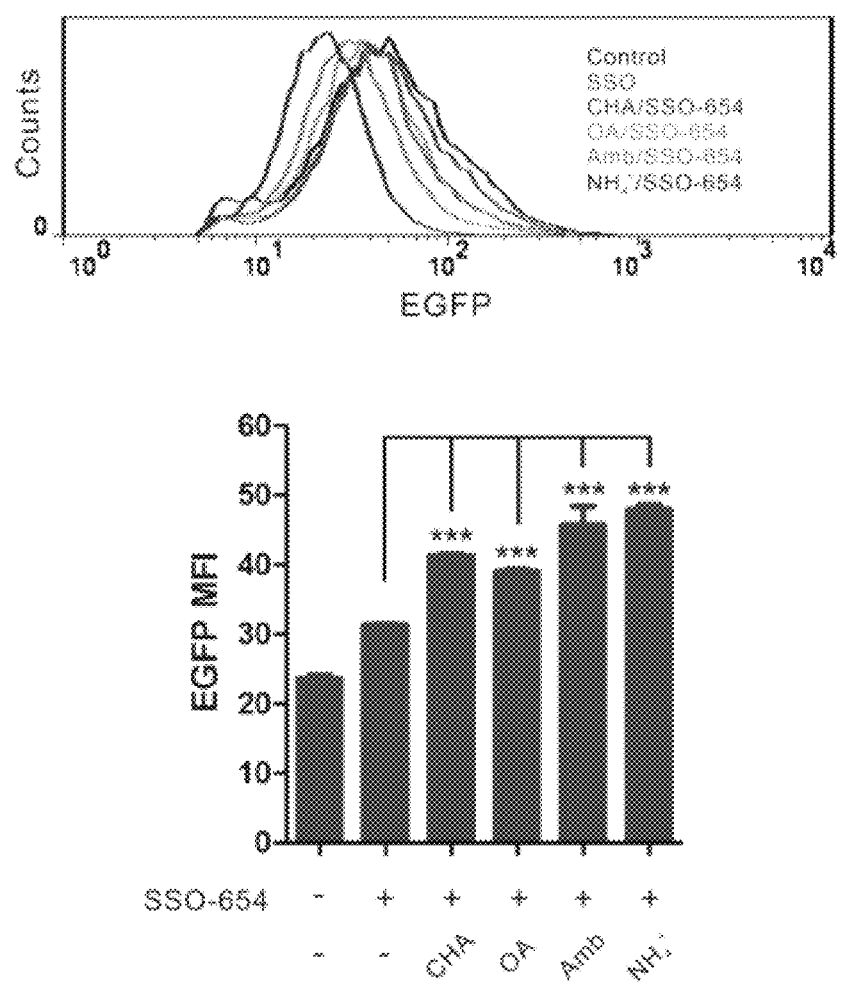
Figure 35:
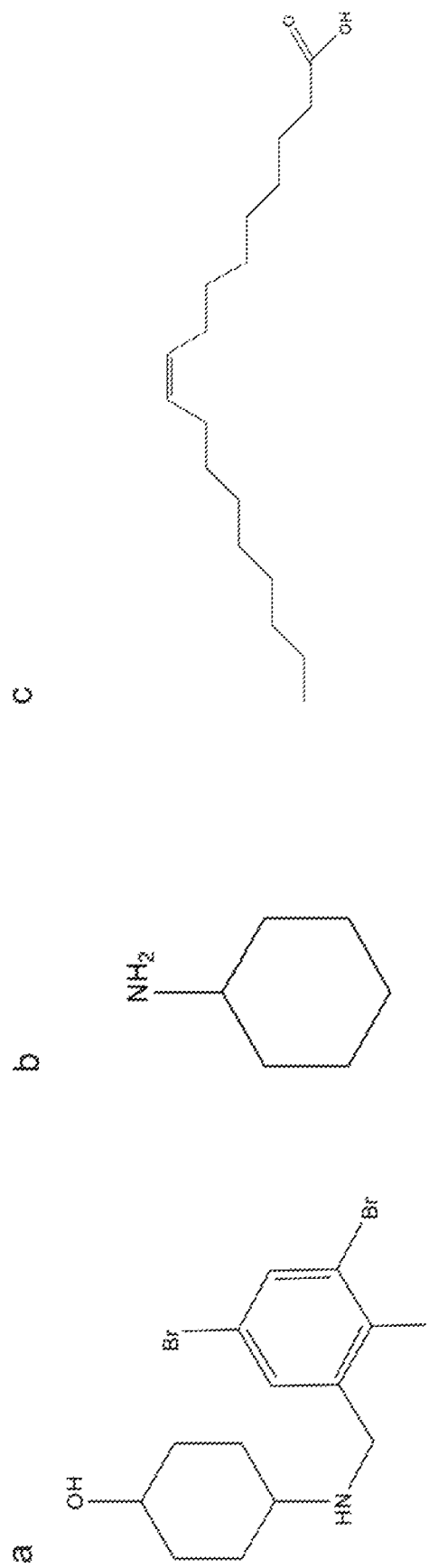
FIGS. 35a-35c show the molecular structures of Ambroxol (FIG. 35a), Cyclohexylamine (FIG. 35b), and oleic acid (FIG. 35c).
Figure 36:
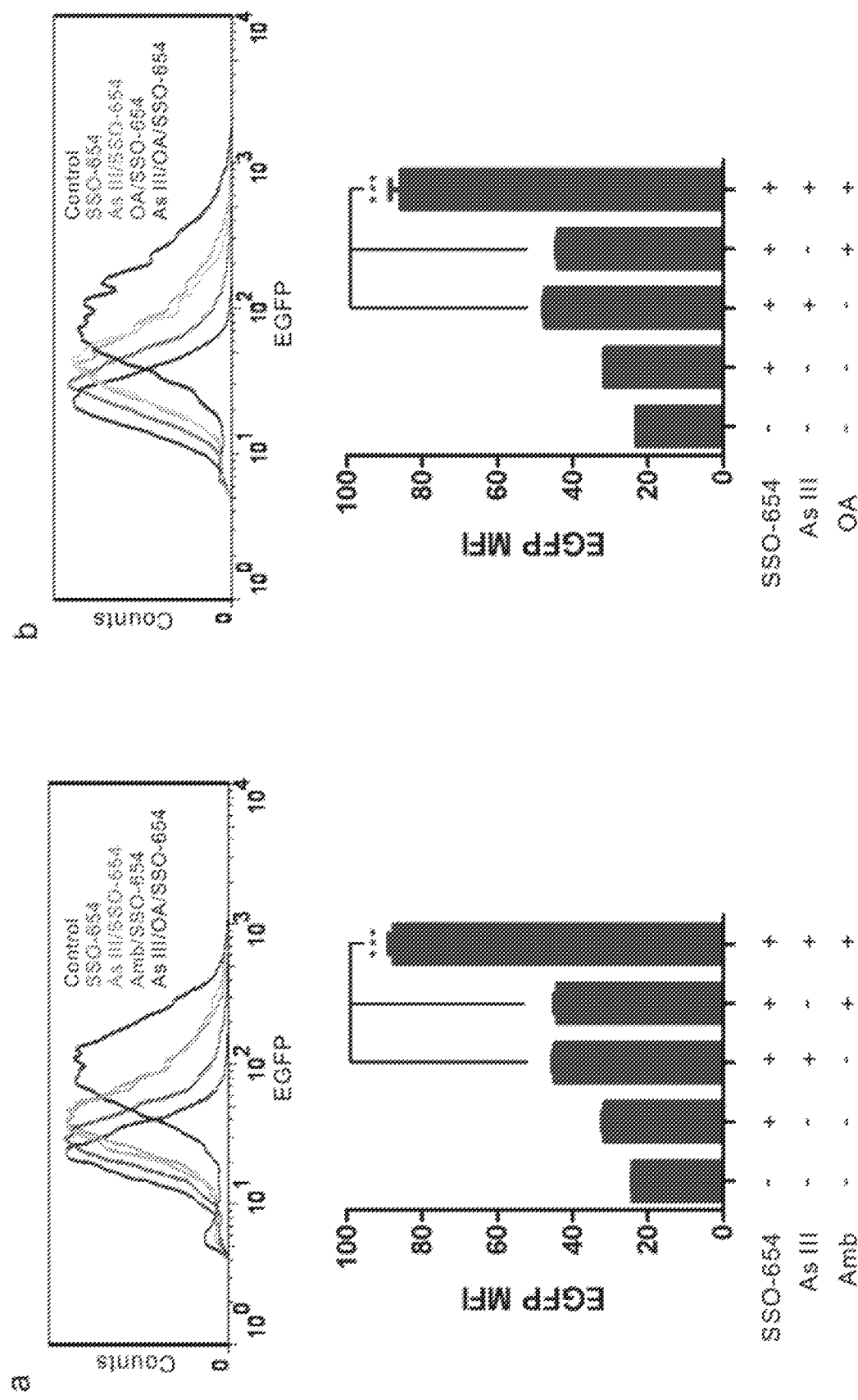
FIGS. 36a and 36b show that the activity of SSO-654 can be increased by combining As III with endosome/lysosome inhibitors.
Figure 37:
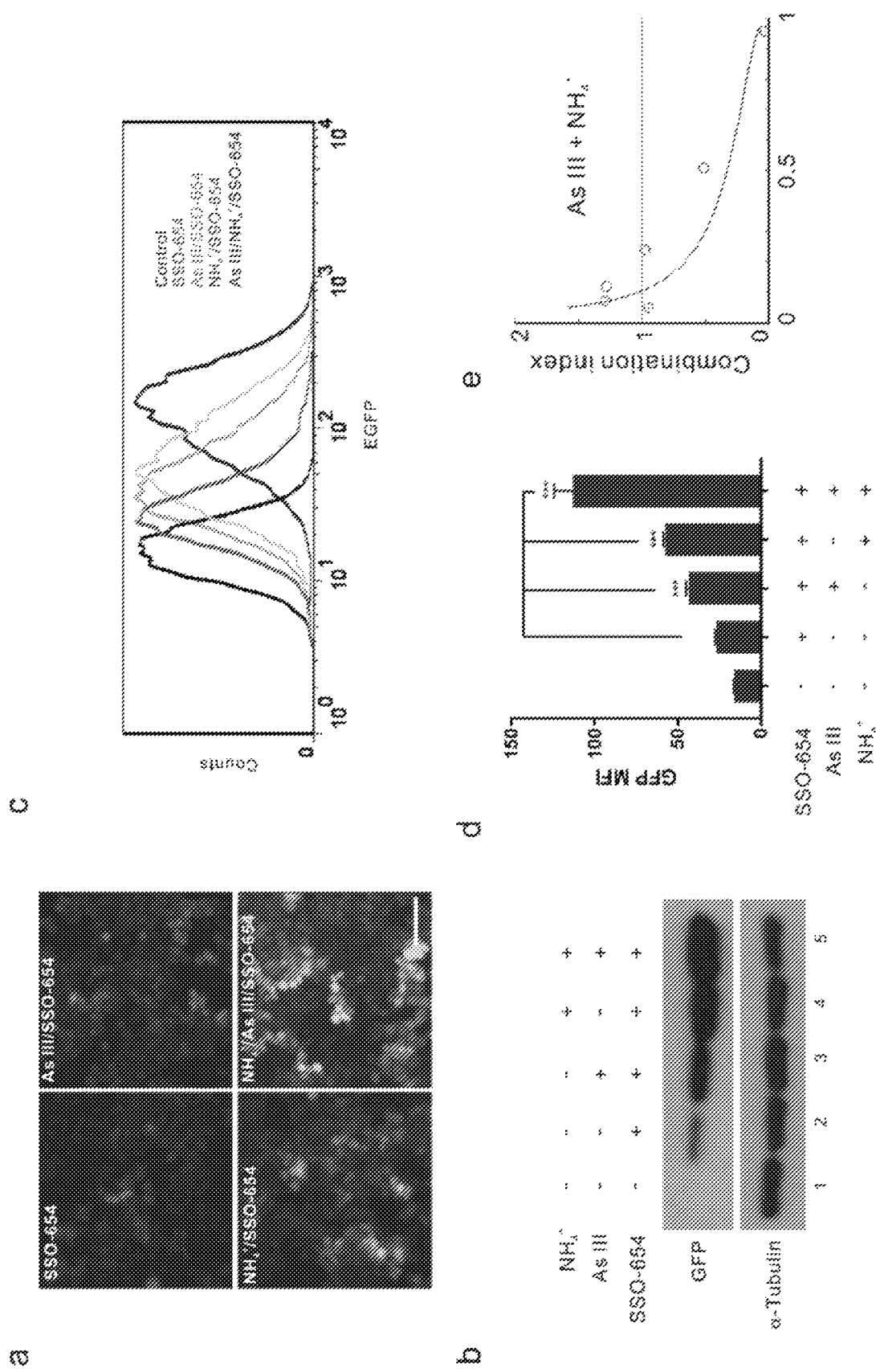
FIGS. 37a-37e show that $NH_4^+$ and As III are synergistic in facilitating SSO activity.

Example 13: Ammonium Ion Facilitates Oligonucleotides Function Possibly Through Inhibiting Endosomal Maturation To understand how $NH_4+$ facilitates ASO and SSO activity, whether it increased oligonucleotide uptake in cells was examined. In FIG. 34a, the cells were treated with 100 nM Cy5-ASO in the presence or absence of 5 mM $NH_4+$ for 12 hr, and then harvested for flow cytometry. As shown in FIG. 34a, 5 mM $NH_4+$ did not significantly affect the cellular uptake of a Cy5-labeled ASO (Cy5-ASO) in LNCaP cells (p=0.98), suggesting that the activity of $NH_4+$ occurs intracellularly. $NH_4+$ is known to inhibit endosomal maturation and lysosome fusion (73-75). These processes play a critical role in oligonucleotide delivery within the cell after PS ON uptake via adsorptive and/or fluid phase endocytosis, as it has been found that 50% internalized oligonucleotide is associated to lysosomes and other vesicular structures (76). In FIG. 34b, the cells were transfected with LIPO-FECTAMINE® 3000 and 20 nM SSO-654 in the presence or absence of 5 mM $NH_4+$; after 2 days, cells were harvested for flow cytometric evaluation of EGPF expression. Acting at the level of the endosome, $NH_4+$ did not enhance the activity of the SSO-654 when it was delivered by LIPO-FECTAMINE®3000-based transfection of HeLa EGFP-654 cells (FIG. 34b). Lipofection is thought to facilitate oligonucleotide delivery by affecting the integrity of the lipid bilayer. Thus, after cellular transfection with LIPO-FECTAMINE®, it is reasonable to postulate that release of the oligonucleotide from the endosome would be less susceptible to any alteration in the endosomal maturation and fusion steps. Three other inhibitors of endosomal maturation/fusion, Ambroxol (Amb), cyclohexylamine (CHA) and oleic acid (OA) (shown in FIG. 35), also significantly enhanced SSO-654 activity in HeLa EGFP-654 cells when delivered by gym nosis and in combination with As III (FIG. 34c and FIGS. 36a and 36b), further corroborating the notion that enhancement of oligonucleotide efficacy is occurring at the level of the endosome. In FIG. 34c, the HeLa EGFP-654 cells were treated with 1 µM SSO-654 and 5 mM $NH_4+$, or 50 µM Amb, or 500 µM CHA or 200 µM OA for 2 days prior to flow cytometry assays. It is noteworthy that the former two compounds are organic amines, but their pKas (9.1 for Ambroxol (77), 10.62 for cyclohexylamine (78)) are, like ammonia's pKa (9.26)(78), too high for any of these small molecules to act as intra-endosomal proton sponges. OA may also work by an additional mechanism: It stimulates PKCα activity, which promotes endosomal maturation and oligonucleotide function (79).

Example 14: Ammonium Ion and as III Synergistically Enhance SSO-654 Activity in HeLa EGFP-654 Cells As III and $NH_4^+$ work through different mechanisms, so the two were combined. Their function is strikingly synergistic in improving nuclear and cytoplasmic gene targeting. This was determined by the following studies. $NH_4^+$ can aid nuclear SSO function since it will increase the available concentration of functional oligonucleotide (that can shuttle into the nucleus) by increasing its endosomal release. Therefore, a further increase in oligonucleotide nuclear function can be induced by combining the As III and $NH_4^+$ treatments.

As III facilitates SSO activity as shown in FIGS. 37a-37d and FIG. 38a; (compare As III/SSO-654 with SSO-654) in a dose-dependent manner (FIG. 38a). In FIG. 38a, the HeLa EGPF-654 cells were treated for two days with 1 µM SSO-654 in the presence or absence of 1 µM As III, or otherwise indicated, prior to microscopy and Western blot assays. In FIG. 38b, HCT116 cells were treated with 1 µM β-Cat-ASO, 1 µM As III, 5 mM $NH_4$, or their combination as indicated for two days; and Jurkat T cells were treated with 1 µM BCL2-ASO, 1 µM As III, or 5 mM $NH_4$, or their combination as indicated for two days. As III. unlike $NH_4$, did not significantly increase β-catenin- or BCL2-ASO activity in HCT116 or Jurkat T cells (FIG. 38b, compare lane 6 with lane 4). These findings support the observation that As III triggers the shuttling of the oligonucleotide into the nuclear compartment. Since $NH_4^+$ seemed to enhance release of oligonucleotide into the cytoplasm, the combination of the two small molecules could further augment the activity of the SSO in the nucleus.

As shown in FIGS. 37a-37d (fluorescence microscopy, Western blotting for EGFP, and flow cytometry respectively), the combination of $NH_4$, As III and SSO-654 increased EGFP expression in HeLa EGFP-654 cells compared with either the combination of $NH_4^+$ and SSO-654, or of As III and SSO-654. By Western blotting, cells treated with $NH_4^+$+As III manifested more than a ten-fold increase in SSO-654-mediated EGFP expression than treatment with the SSO-654 alone. This is compared to a three- to five-fold upregulation of SSO-654-mediated EGFP expression by either $NH_4^+$ or As III (evaluated by Western blotting in FIG. 37b and by flow cytometry in FIGS. 37c and 37d). To investigate whether these two small molecules in combination produced a synergistic effect on SSO activity, a dose-response study was performed as shown in Table 2 below.

Quantitative analysis was performed by flow cytometry, which allowed the production of a combination index (CI) plot using the Chou-Talalay method (70), in which the line parallel to the x-axis (CI=1, FIG. 37e) represents the divide between additivity (CI=1) and antagonism (CI>1) for the two drugs being analyzed in combination. A CI<1 demonstrates drug synergism, which increases as CI decreases. The two most relevant points in the experiment, performed at fractional activity (Fa), =0.5 and 1.0, fall well below CI=1 (FIG. 37e; note that the lower ammonium+As III concentrations produced essentially only basal SSO-654 activity). Therefore, the combination of $NH_4^+$ and As III was synergistic with respect to the facilitation of SSO-654 function in HeLa EGFP-654 cells.

In addition to mRNA gene targeting, the single or combined use of As III and $NH_4^+$ or other stressors can be employed to improve targeting of other sequences and molecules including, but not limited to, ncRNA, piRNA, miRNA, viral RNA and DNA promoter sequences.

Further, in presence of ASO (which causes a stress signal) there is a higher concentration of miRNAs and oligonucleotide in the YBX-1 complex. The YB-1 was immunoprecipitated using cellular lysates harvested from untreated cells or cells treated with a gymnotic delivered oligonucleotide. The association of miRNAs with YB-1 appears to increase when the oligonucleotide is present (FIG. 39a, compare lane 4 to lane 2). A cellular nuclear cytoplasmic fractionation followed by Northern analysis showed that, similarly to the YB-1 and oligo cellular localization, the concentration of miRNAs increase in the nucleus when cellular stress is induced by the presence of the oligonucleotide and the ATO treatment (FIG. 39b, compare lanes 1 and 2 to lanes 4 and 5 and lanes 5 and 6).

All publications and patent documents cited herein are incorporated by reference.

REFERENCES

1. R. Kole, A. R. Krainer, S. Altman, RNA therapeutics: beyond RNA interference and antisense oligonucleotides. *Nature reviews. Drug discovery* 11, 125 (Jan. 20, 2012).

TABLE 2

| EGFP MFI increases from treatments, mean ± SD ||||||
| $NH_4^+$ || As III || $NH_4^+$/As III ||
| Conc. (mM) | MFI increase | Conc. (µM) | MFI increase | Conc. (mM/µM) | MFI increases |
| --- | --- | --- | --- | --- | --- |
| 0.3 | 0.43 ± 0.23 | 0.06 | 3.23 ± 0.35 | 0.3/0.06 | 3.13 ± 0.25 |
| 0.63 | 1.03 ± 0.38 | 0.125 | 4.17 ± 0.38 | 0.63/0.125 | 4.60 ± 0.35 |
| 1.25 | 3.20 ± 1.21 | 0.25 | 6.40 ± 0.20 | 1.25/0.25 | 8.07 ± 1.27 |
| 2.5 | 6 ± 1.11 | 0.5 | 9.77 ± 0.31 | 2.5/0.5 | 15.37 ± 0.50 |
| 5 | 11.47 ± 0.21 | 1 | 17.63 ± 0.90 | 5/1 | 32.93 ± 2.53 |
| 10 | 21.73 ± 1.51 | 2 | 28.10 ± 0.82 | 10/2 | 62.00 ± 4.76 |

HeLa EGFP-654 cells were treated with 1 µM SSO-654 in the presence of $NH_4$, As III, or both at fixed molar ratios for two days, prior to flow cytometry. Flow data from three independent experiments were analyzed with the FlowJo program (Tree Star, Inc., Ashland, Oreg.) to obtain EGFP MFI values. The MFI from the cells treated with 1 µM SSO-654 alone were used as the background control to calculate the MFI increase after drug treatment. A combination index (CI) plot was generated and CI values were obtained according to the method of Chou and Talalay (70).

2. K. T. Gagnon, L. Li, Y. Chu, B. A. Janowski, D. R. Corey, RNAi factors are present and active in human cell nuclei. *Cell reports* 6, 211 (Jan. 16, 2014).

3. C. Catalanotto, C. Cogoni, G. Zardo, MicroRNA in Control of Gene Expression: An Overview of Nuclear Functions. *International journal of molecular sciences* 17, (Oct. 13, 2016).

4. D. Castanotto et al., A cytoplasmic pathway for gapmer antisense oligonucleotide-mediated gene silencing in mammalian cells. *Nucleic acids research* 43, 9350 (Oct. 30, 2015).
5. D. A. Weidner, B. C. Valdez, D. Henning, S. Greenberg, H. Busch, Phosphorothioate Oligonucleotides Bind in a Non Sequence-Specific Manner to the Nucleolar Protein C23/Nucleolin. *Febs Lett* 366, 146 (Jun. 12, 1995).
6. X. H. Liang, W. Shen, H. Sun, T. P. Prakash, S. T. Crooke, TCP1 complex proteins interact with phosphorothioate oligonucleotides and can co-localize in oligonucleotide-induced nuclear bodies in mammalian cells. *Nucleic acids research* 42, 7819 (Aug. 1, 2014).
7. N. K. Christensen et al., A novel class of oligonucleotide analogues containing 2'-O,3'-C-linked [3.2.0]bicycloarabinonucleoside monomers: Synthesis, thermal affinity studies, and molecular modeling. *J Am Chem Soc* 120, 5458 (Jun. 10, 1998).
8. C. Wahlestedt et al., Potent and nontoxic antisense oligonucleotides containing locked nucleic acids. *P Natl Acad Sci USA* 97, 5633 (May 9, 2000).
9. M. Gama-Carvalho, M. Carmo-Fonseca, The rules and roles of nucleocytoplasmic shuttling proteins. *Febs Lett* 498, 157 (Jun. 8, 2001).
10. M. Muller-McNicoll et al., SR proteins are NXF1 adaptors that link alternative RNA processing to mRNA export. *Genes & development* 30, 553 (Mar. 1, 2016).
11. B. Jiang et al., Nucleolin/C23 mediates the antiapoptotic effect of heat shock protein 70 during oxidative stress. *The FEBS journal* 277, 642 (February, 2010).
12. T. Tanaka, S. Ohashi, S. Kobayashi, Roles of YB-1 under arsenite-induced stress: translational activation of HSP70 mRNA and control of the number of stress granules. *Biochimica et biophysica acta* 1840, 985 (March, 2014).
13. A. V. Sorokin et al., Proteasome-mediated cleavage of the Y-box-binding protein 1 is linked to DNA-damage stress response. *The EMBO journal* 24, 3602 (Oct. 19, 2005).
14. K. Matsumoto, A. P. Wolffe, Gene regulation by Y-box proteins: coupling control of transcription and translation. *Trends in cell biology* 8, 318 (August, 1998).
15. P. L. Graumann, M. A. Marahiel, A superfamily of proteins that contain the cold-shock domain. *Trends in biochemical sciences* 23, 286 (August, 1998).
16. J. R. Buchan, R. Parker, Eukaryotic stress granules: the ins and outs of translation. *Molecular cell* 36, 932 (Dec. 25, 2009).
17. K. M. Bartoli, J. Jakovljevic, J. L. Woolford, Jr., W. S. Saunders, Kinesin molecular motor Eg5 functions during polypeptide synthesis. *Molecular biology of the cell* 22, 3420 (September, 2011).
18. A. N. Sasikumar, W. B. Perez, T. G. Kinzy, The many roles of the eukaryotic elongation factor 1 complex. *Wiley interdisciplinary reviews. RNA* 3, 543 (July-August, 2012).
19. B. F. Pickering, D. H. Yu, M. W. Van Dyke, Nucleolin Protein Interacts with Microprocessor Complex to Affect Biogenesis of MicroRNAs 15a and 16. *J Biol Chem* 286, 44095 (Dec. 23, 2011).
20. D. Schmitter et al., Effects of Dicer and Argonaute down-regulation on mRNA levels in human HEK293 cells. *Nucleic acids research* 34, 4801 (2006).
21. P. J. Bates, J. B. Kahlon, S. D. Thomas, J. O. Trent, D. M. Miller, Antiproliferative activity of G-rich oligonucleotides correlates with protein binding. *J Biol Chem* 274, 26369 (Sep. 10, 1999).
22. E. M. Reyes-Reyes, Y. Teng, P. J. Bates, A new paradigm for aptamer therapeutic AS1411 action: uptake by macropinocytosis and its stimulation by a nucleolin-dependent mechanism. *Cancer research* 70, 8617 (Nov. 1, 2010).
23. S. Fredriksson et al., Protein detection using proximity-dependent DNA ligation assays. *Nature biotechnology* 20, 473 (May, 2002).
24. K. J. Leuchowius, I. Weibrecht, O. Soderberg, In situ proximity ligation assay for microscopy and flow cytometry. *Current protocols in cytometry* Chapter 9, Unit 9 36 (April, 2011).
25. I. A. Eliseeva, E. R. Kim, S. G. Guryanov, L. P. Ovchinnikov, D. N. Lyabin, Y-box-binding protein 1 (YB-1) and its functions. *Biochemistry. Biokhimiia* 76, 1402 (December, 2011).
26. A. Emde, E. Hornstein, miRNAs at the interface of cellular stress and disease. *The EMBO journal* 33, 1428 (Jul. 1, 2014).
27. K. Higashi et al., Interferon-gamma interferes with transforming growth factor-beta signaling through direct interaction of YB-1 with Smad3. *J Biol Chem* 278, 43470 (Oct. 31, 2003).
28. B. Schmierer, C. S. Hill, TGFbeta-SMAD signal transduction: molecular specificity and functional flexibility. *Nature reviews. Molecular cell biology* 8, 970 (December, 2007).
29. P. Sazani et al., Nuclear antisense effects of neutral, anionic and cationic oligonucleotide analogs. *Nucleic acids research* 29, 3965 (Oct. 1, 2001).
30. R. C. Lantz, A. M. Hays, Role of oxidative stress in arsenic-induced toxicity. *Drug Metab Rev* 38, 791 (2006).
31. X. Thomas, J. Troncy, Arsenic: a beneficial therapeutic poison—a historical overview. *Adler Museum bulletin* 35, 3 (June, 2009).
32. C. Blenkiron, D. G. Hurley, S. Fitzgerald, C. G. Print, A. Lasham, Links between the oncoprotein YB-1 and small non-coding RNAs in breast cancer. *PloS one* 8, e80171 (2013).
33. T. B. Hansen et al., miRNA-dependent gene silencing involving Ago2-mediated cleavage of a circular antisense RNA. *Embo Journal* 30, 4414 (Nov. 2, 2011).
34. T. B. Hansen et al., Natural RNA circles function as efficient microRNA sponges. *Nature* 495, 384 (Mar. 21, 2013).
35. S. Memczak et al., Circular RNAs are a large class of animal RNAs with regulatory potency. *Nature* 495, 333 (Mar. 21, 2013).
36. E. Leucci et al., microRNA-9 targets the long non-coding RNA MALAT1 for degradation in the nucleus. *Scientific reports* 3, 2535 (2013).
37. N. Kedersha et al., Stress granules and processing bodies are dynamically linked sites of mRNP remodeling. *The Journal of cell biology* 169, 871 (Jun. 20, 2005).
38. A. Wilczynska, C. Aigueperse, M. Kress, F. Dautry, D. Weil, The translational regulator CPEB1 provides a link between dcp1 bodies and stress granules. *Journal of cell science* 118, 981 (Mar. 1, 2005).
39. D. Dormann et al., ALS-associated fused in sarcoma (FUS) mutations disrupt Transportin-mediated nuclear import. *The EMBO journal* 29, 2841 (Aug. 18, 2010).
40. M. Morlando et al., FUS stimulates microRNA biogenesis by facilitating co-transcriptional Drosha recruitment. *The EMBO journal* 31, 4502 (Dec. 12, 2012).
41. I. V. Chernukhin et al., Physical and functional interaction between two pluripotent proteins, the Y-box DNA/

RNA-binding factor, YB-1, and the multivalent zinc finger factor, CTCF. *J Biol Chem* 278, 29915 (Sep. 22, 2000).
42. R. Bergstrom et al., Transforming Growth Factor beta Promotes Complexes between Smad Proteins and the CCCTC-binding Factor on the H19 Imprinting Control Region Chromatin. *J Biol Chem* 288, 19727 (Jun. 25, 2010).
43. K. Nishi, A. Nishi, T. Nagasawa, K. Ui-Tei, Human TNRC6A is an Argonaute-navigator protein for microRNA-mediated gene silencing in the nucleus. *Rna* 19, 17 (January, 2013).
44. D. Castanotto, R. Lingeman, A. D. Riggs, J. J. Rossi, CRM1 mediates nuclear-cytoplasmic shuttling of mature microRNAs. *Proc Natl Acad Sci USA* 106, 21655 (Dec. 22, 2009).
45. A. K. Leung, P. A. Sharp, MicroRNA functions in stress responses. *Molecular cell* 40, 205 (Oct. 22, 2010).
46. A. Detzer, C. Engel, W. Wunsche, G. Sczakiel, Cell stress is related to re-localization of Argonaute 2 and to decreased RNA interference in human cells. *Nucleic acids research* 39, 2727 (April, 2011).
47. Z. Xiao, N. Watson, C. Rodriguez, H. F. Lodish, Nucleo-cytoplasmic shuttling of Smad1 conferred by its nuclear localization and nuclear export signals. *J Biol Chem* 276, 39404 (Oct. 19, 2001).
48. U. Upadhyay et al., Ablation of RNA interference and retrotransposons accompany acquisition and evolution of transposases to heterochromatin protein CENPB. *Molecular biology of the cell* 28, 1132 (Apr. 15, 2017).
49. S. J. Chen et al., From an old remedy to a magic bullet: molecular mechanisms underlying the therapeutic effects of arsenic in fighting leukemia. *Blood* 117, 6425 (Jun. 16, 2011).
50. Stein, C. A. and Castanotto, D. (2017) FDA-Approved Oligonucleotide Therapies in 2017. *Molecular therapy: the journal of the American Society of Gene Therapy.*
51. Mendell, J. R., Goemans, N., Lowes, L. P., Alfano, L. N., Berry, K., Shao, J., Kaye, E. M., Mercuri, E., Eteplirsen Study, G. and Telethon Foundation, D. M. D. I. N. (2016) Longitudinal effect of eteplirsen versus historical control on ambulation in Duchenne muscular dystrophy. *Annals of neurology,* 79, 257-271.
52. Disterer, P., Kryczka, A., Liu, Y., Badi, Y. E., Wong, J. J., Owen, J. S. and Khoo, B. (2014) Development of therapeutic splice-switching oligonucleotides. *Human gene therapy,* 26, 587-598.
53. http:/us.gsk.com/en-us/media/press-releases/2014/prosensa-regains-rights-to-drisapersen-from-qsk-and-retains-rihts-to-all-other-programmes-for-the-treatment-of-duchenne-muscular-dystrophy-dmd/.
54. Hache, M., Swoboda, K. J., Sethna, N., Farrow-Gillespie, A., Khandji, A., Xia, S. and Bishop, K. M. (2016) Intrathecal Injections in Children With Spinal Muscular Atrophy: Nusinersen Clinical Trial Experience. *Journal of child neurology,* 31, 899-906.
55. Burdick, A. D., Sciabola, S., Mantena, S. R., Hollingshead, B. D., Stanton, R., Wameke, J. A., Zeng, M., Martsen, E., Medvedev, A., Makarov, S. S. et al. (2014) Sequence motifs associated with hepatotoxicity of locked nucleic acid-modified antisense oligonucleotides. *Nucleic acids research,* 42, 4882-4891.
56. Straarup, E. M., Fisker, N., Hedtjam, M., Lindholm, M. W., Rosenbohm, C., Aarup, V., Hansen, H. F., Orum, H., Hansen, J. B. and Koch, T. (2010) Short locked nucleic acid antisense oligonucleotides potently reduce apolipoprotein B mRNA and serum cholesterol in mice and non-human primates. *Nucleic acids research,* 38, 7100-7111.
57. Christensen, N. K., Petersen, M., Nielsen, P., Jacobsen, J. P., Olsen, C. E. and Wengel, J. (1998) A novel class of oligonucleotide analogues containing 2'-O,3'-C-linked [3.2.0]bicydoarabinonucleoside monomers: Synthesis, thermal affinity studies, and molecular modeling. *J Am Chem Soc,* 120, 5458-5463.
58. Wahlestedt, C., Salmi, P., Good, L., Kela, J., Johnsson, T., Hokfelt, T., Broberger, C., Porreca, F., Lai, J., Ren, K. et al. (2000) Potent and nontoxic antisense oligonucleotides containing locked nucleic acids. *Proceedings of the National Academy of Sciences of the United States of America,* 97, 5633-5638.
59. Kurreck, J. (2003) Antisense technologies. Improvement through novel chemical modifications. *European journal of biochemistry,* 270, 1628-1644.
60. Roberts, J., Palma, E., Sazani, P., Orum, H., Cho, M. and Kole, R. (2006) Efficient and persistent splice switching by systemically delivered LNA oligonucleotides in mice. *Molecular therapy: the journal of the American Society of Gene Therapy,* 14, 471-475.
61. Sazani, P., Gemignani, F., Kang, S. H., Maier, M. A., Manoharan, M., Persmark, M., Bortner, D. and Kole, R. (2002) Systemically delivered antisense oligomers upregulate gene expression in mouse tissues. *Nature biotechnology,* 20, 1228-1233.
62. Sazani, P., Kang, S. H., Maier, M. A., Wei, C., Dillman, J., Summerton, J., Manoharan, M. and Kole, R. (2001) Nuclear antisense effects of neutral, anionic and cationic oligonucleotide analogs. *Nucleic acids research,* 29, 3965-3974.
63. Stein, C. A., Hansen, J. B., Lai, J., Wu, S., Voskresenskiy, A., Hog, A., Worm, J., Hedtjam, M., Souleimanian, N., Miller, P. et al. (2010) Efficient gene silencing by delivery of locked nucleic acid antisense oligonucleotides, unassisted by transfection reagents. *Nucleic acids research,* 38, e3.
64. Soifer, H. S., Koch, T., Lai, J., Hansen, B., Hoeg, A., Oerum, H. and Stein, C. A. (2012) Silencing of gene expression by gymnotic delivery of antisense oligonucleotides. *Methods in molecular biology,* 815, 333-346.
65. Souleimanian, N., Deleavey, G. F., Soifer, H., Wang, S., Tiemann, K., Damha, M. J. and Stein, C. A. (2012) Antisense 2'-Deoxy, 2'-Fluoroarabino Nucleic Acid (2'F-ANA) Oligonucleotides: In Vitro Gymnotic Silencers of Gene Expression Whose Potency Is Enhanced by Fatty Acids. *Molecular therapy. Nucleic acids,* 1, e43.
66. Juliano, R. L. and Carver, K. (2015) Cellular uptake and intracellular trafficking of oligonucleotides. *Advanced drug delivery reviews,* 87, 35-45.
67. Ming, X., Carver, K., Fisher, M., Noel, R., Cintrat, J. C., Gillet, D., Barbier, J., Cao, C., Bauman, J. and Juliano, R. L. (2013) The small molecule Retro-1 enhances the pharmacological actions of antisense and splice switching oligonucleotides. *Nucleic acids research,* 41, 3673-3687.
68. Yang, B., Ming, X., Cao, C., Laing, B., Yuan, A., Porter, M. A., Hull-Ryde, E. A., Maddry, J., Suto, M., Janzen, W. P. et al. (2015) High-throughput screening identifies small molecules that enhance the pharmacological effects of oligonucleotides. *Nucleic acids research,* 43, 1987-1996.
69. Kendall, G. C., Mokhonova, E. I., Moran, M., Sejbuk, N. E., Wang, D. W., Silva, O., Wang, R. T., Martinez, L., Lu, Q. L., Damoiseaux, R. et al. (2012) Dantrolene enhances antisense-mediated exon skipping in human and mouse models of Duchenne muscular dystrophy. *Science translational medicine*, 4, 164ra160.
70. Chou, T. C. and Talalay, P. (1984) Quantitative analysis of dose-effect relationships: the combined effects of multiple drugs or enzyme inhibitors. *Advances in enzyme regulation*, 22, 27-55.
71. Schneider, M., Marison, I. W. and von Stockar, U. (1996) The importance of ammonia in mammalian cell culture. *Journal of biotechnology*, 46, 161-185.
72. Hansen, H. A. and Emborg, C. (1994) Influence of ammonium on growth, metabolism, and productivity of a continuous suspension Chinese hamster ovary cell culture. *Biotechnology progress*, 10, 121-124.
73. Huotari, J. and Helenius, A. (2011) Endosome maturation. *The EMBO journal*, 30, 3481-3500.
74. van Weert, A. W., Dunn, K. W., Geuze, H. J., Maxfield, F. R. and Stoorvogel, W. (1995) Transport from late endosomes to lysosomes, but not sorting of integral membrane proteins in endosomes, depends on the vacuolar proton pump. The *Journal of cell biology*, 130, 821-834.
75. Weisz, O. A. (2003) Acidification and protein traffic. *International review of cytology*, 226, 259-319.
76. Yakubov, L. A., Deeva, E. A., Zarytova, V. F., Ivanova, E. M., Ryte, A. S., Yurchenko, L. V. and Vlassov, V. V. (1989) Mechanism of oligonucleotide uptake by cells: involvement of specific receptors? *Proceedings of the National Academy of Sciences of the United States of America*, 86, 6454-6458.
77. https://www.drugbank.ca/drugs/DB06742.
78. www.csun.edu/~hcchm003/321/Ka.pdf.
79. Castanotto, D., Lin, M., Kowolik, C., Koch, T., Hansen, B. R., Oerum, H. and Stein, C. A. (2016) Protein Kinase C-alpha is a Critical Protein for Antisense Oligonucleotide-mediated Silencing in Mammalian Cells. *Molecular therapy: the journal of the American Society of Gene Therapy*, 24, 1117-1125.
80. Dean, R. T., Jessup, W. and Roberts, C. R. (1984) Effects of exogenous amines on mammalian cells, with particular reference to membrane flow. *The Biochemical journal*, 217, 27-40.
81. Castanotto, D., Lin, M., Kowolik, C., Wang, L., Ren, X. Q., Soifer, H. S., Koch, T., Hansen, B. R., Oerum, H., Armstrong, B. et al. (2015) A cytoplasmic pathway for gapmer antisense oligonucieotide-mediated gene silencing in mammalian cells. *Nucleic acids research*, 43, 9350-9361.
82. Siomi, H. and Siomi, M. C. (2009) RISC hitches onto endosome trafficking. *Nature cell biology*, 11, 1049-1051.
83. Koller, E., Vincent, T. M., Chappell, A., De, S., Manoharan, M. and Bennett, C. F. (2011) Mechanisms of single-stranded phosphorothioate modified antisense oligonucleotide accumulation in hepatocytes. *Nucleic acids research*, 39, 4795-4807.
84. Schindler, J. F. and Devries, U. (1990) Effects of Ammonia, Chloroquine, and Monensin on the Vacuolar Apparatus of an Absorptive Epithelium. *Cell Tissue Res*, 269, 283-292.
85. Misinzo, G., Delputte, P. L. and Nauwynck, H. J. (2008) Inhibition of endosome-lysosome system acidification enhances porcine circovirus 2 infection of porcine epithelial cells. *Journal of virology*, 82, 1128-1135.
86. Juliano, R., Alam, M. R., Dixit, V. and Kang, H. (2008) Mechanisms and strategies for effective delivery of antisense and siRNA oligonucleotides. *Nucleic acids research*, 36, 4158-4171.
87. Zhang, X. W., Yan, X. J., Zhou, Z. R., Yang, F. F., Wu, Z. Y., Sun, H. B., Liang, W. X., Song, A. X., Lallemand-Breitenbach, V., Jeanne, M. et al. (2010) Arsenic trioxide controls the fate of the PML-RARalpha oncoprotein by directly binding PML. *Science*, 328, 240-243.
88. Jeanne, M., Lallemand-Breitenbach, V., Ferhi, O., Koken, M., Le Bras, M., Duffort, S., Peres, L., Berthier, C., Soilihi, H., Raught, B. et al. (2010) PML/RARA oxidation and arsenic binding initiate the antileukemia response of As2O3. *Cancer cell*, 18, 88-98.
89. Chen, S. J., Zhou, G. B., Zhang, X. W., Mao, J. H., de The, H. and Chen, Z. (2011) From an old remedy to a magic bullet: molecular mechanisms underlying the therapeutic effects of arsenic in fighting leukemia. *Blood*, 117, 6425-6437.
90. Hu, J., Liu, Y. F., Wu, C. F., Xu, F., Shen, Z. X., Zhu, Y. M., Li, J. M., Tang, W., Zhao, W. L., Wu, W. et al. (2009) Long-term efficacy and safety of all-trans retinoic acid/arsenic trioxide-based therapy in newly diagnosed acute promyelocytic leukemia. *Proceedings of the National Academy of Sciences of the United States of America*, 106, 3342-3347.

The invention claimed is:

1. A method of enhancing gene targeting comprising:
    administering an oligonucleotide to a cell, wherein the oligonucleotide binds a target molecule in the cell selected from (i) a mutant β-globin, (ii) BCL-2, (iii) β-catenin, or (iv) androgen receptor; and
    administering (A) a stressor and (B) a proton sponge molecule to the cell, wherein the stressor induces a cellular stress response;
    wherein co-administration of (A) and (B) with the oligonucleotide enhances the function of the oligonucleotide;
    wherein the stressor comprises arsenic trioxide, $H_2O_2$, or heat shock; and
    wherein the proton sponge molecule comprises inorganic ammonium or an inorganic ammonium salt.

2. The method of claim 1, wherein the oligonucleotide comprises an antisense oligonucleotide (ASO), a splicing switch oligonucleotide (SSO), siRNA, miRNA, or shRNA.

3. The method of claim 1, wherein the cell is a cultured cell or part of a tissue or organ.

4. The method of claim 1, wherein the target molecule comprises a nucleotide sequence.

5. The method of claim 4, wherein the nucleotide sequence is found in the cell nucleus or the cell nucleolus, or in the cell cytoplasm.

6. The method of claim 5, wherein the nucleotide sequence comprises an mRNA, ncRNA, piRNA, miRNA, viral RNA, or a promoter sequence.

7. The method of claim 1, wherein the oligonucleotide, the stressor, or the proton sponge molecule is administered as a liquid, solid, vapor or any other formulation, or is administered orally, via injection, absorption, or inhalation.

8. The method of claim 1, wherein the oligonucleotide, (A), and (B) are part of a composition.

9. The method of claim 1, wherein the cell is a cancer cell.

10. The method of claim 2, wherein the oligonucleotide is an antisense oligonucleotide (ASO) having a sequence comprising SEQ ID NO:1, SEQ ID NO:3, SEQ ID NO:4, SEQ ID NO:5, or SEQ ID NO:6.

11. The method of claim 10, further comprising administering a second oligonucleotide to a cell, wherein the second oligonucleotide binds a second target molecule in the cell.

12. The method of claim 11, wherein the second oligonucleotide is a second antisense oligonucleotide (ASO) that binds a target molecule selected from (i) a mutant β-globin, (ii) BCL-2, (iii) β-catenin, or (iv) androgen receptor; and binds a different target molecule than the first ASO.

13. The method of claim 12, wherein the second ASO has a sequence comprising SEQ ID NO:1, SEQ ID NO:3, SEQ ID NO:4, SEQ ID NO:5, or SEQ ID NO:6.

* * * * *

SEQUENCE LISTING

<160> NUMBER OF SEQ ID NOS: 6

<210> SEQ ID NO 1
<211> LENGTH: 16
<212> TYPE: DNA
<213> ORGANISM: Artificial Sequence
<220> FEATURE:
<223> OTHER INFORMATION: SSO-654 oligonucleotide

<400> SEQUENCE: 1
gctattacct taaccc         16

<210> SEQ ID NO 2
<211> LENGTH: 18
<212> TYPE: DNA
<213> ORGANISM: Artificial Sequence
<220> FEATURE:
<223> OTHER INFORMATION: SPC 3046 oligonucleotide
<220> FEATURE:
<221> NAME/KEY: misc_feature

```
<222> LOCATION: (1)..(1)
<223> OTHER INFORMATION: 5-mehtylcytosine
<220> FEATURE:
<221> NAME/KEY: misc_feature
<222> LOCATION: (4)..(4)
<223> OTHER INFORMATION: 5-mehtylcytosine

<400> SEQUENCE: 2
ncgncagatt ataaacct                                                 18

<210> SEQ ID NO 3
<211> LENGTH: 19
<212> TYPE: DNA
<213> ORGANISM: Artificial Sequence
<220> FEATURE:
<223> OTHER INFORMATION: SPC2996 oligonucleotide
<220> FEATURE:
<221> NAME/KEY: misc_feature
<222> LOCATION: (1)..(1)
<223> OTHER INFORMATION: 5-methylcytosine
<220> FEATURE:
<221> NAME/KEY: misc_feature
<222> LOCATION: (15)..(15)
<223> OTHER INFORMATION: 5-methylcytosine
<220> FEATURE:
<221> NAME/KEY: misc_feature
<222> LOCATION: (17)..(17)
<223> OTHER INFORMATION: 5-methylcytosine

<400> SEQUENCE: 3
nctcccagcg tgcgncnca                                                19

<210> SEQ ID NO 4
<211> LENGTH: 19
<212> TYPE: DNA
<213> ORGANISM: Artificial Sequence
<220> FEATURE:
<223> OTHER INFORMATION: Cy5-ASO oligonucleotide
<220> FEATURE:
<221> NAME/KEY: misc_feature
<222> LOCATION: (1)..(1)
<223> OTHER INFORMATION: 5-methylcytosine
<220> FEATURE:
<221> NAME/KEY: misc_feature
<222> LOCATION: (15)..(15)
<223> OTHER INFORMATION: 5-methylcytosine
<220> FEATURE:
<221> NAME/KEY: misc_feature
<222> LOCATION: (17)..(17)
<223> OTHER INFORMATION: 5-methylcytosine

<400> SEQUENCE: 4
nctcccagcg tgcgncnca                                                19

<210> SEQ ID NO 5
<211> LENGTH: 16
<212> TYPE: DNA
<213> ORGANISM: Artificial Sequence
<220> FEATURE:
<223> OTHER INFORMATION: beta-Cat-ASO oligonucleotide

<400> SEQUENCE: 5
ccatcttgtg atccat                                                   16

<210> SEQ ID NO 6
<211> LENGTH: 16
<212> TYPE: DNA
```

```
<213> ORGANISM: Artificial Sequence
<220> FEATURE:
<223> OTHER INFORMATION: AR-ASO (EZN-4176) oligonucleotide

<400> SEQUENCE: 6
accaagtttc ttcagc                                                      16
```